United States Patent
Kaino et al.

(10) Patent No.: US 9,162,988 B2
(45) Date of Patent: *Oct. 20, 2015

(54) THERAPEUTIC OR PROPHYLACTIC AGENT FOR ALLERGIC DERMATITIS

(71) Applicant: Toray Industries, Inc., Tokyo (JP)

(72) Inventors: Mie Kaino, Kanagawa (JP); Hiroyuki Meguro, Kanagawa (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,783

(22) Filed: Dec. 12, 2012

(65) Prior Publication Data

US 2013/0150390 A1  Jun. 13, 2013

Related U.S. Application Data

(63) Continuation of application No. 12/304,964, filed as application No. PCT/JP2007/062017 on Jun. 14, 2007, now abandoned.

(51) Int. Cl.

| | |
|---|---|
| A01N 43/00 | (2006.01) |
| A61K 31/33 | (2006.01) |
| A01N 43/54 | (2006.01) |
| A61K 31/505 | (2006.01) |
| C07D 239/42 | (2006.01) |
| A61K 31/335 | (2006.01) |
| A61K 31/351 | (2006.01) |
| A61K 31/506 | (2006.01) |
| C07D 239/34 | (2006.01) |
| C07D 239/52 | (2006.01) |
| C07D 239/60 | (2006.01) |
| C07D 309/06 | (2006.01) |
| C07D 309/10 | (2006.01) |
| C07D 313/04 | (2006.01) |
| C07D 401/12 | (2006.01) |
| C07D 405/12 | (2006.01) |

(Continued)

(52) U.S. Cl.
CPC ............ *C07D 239/42* (2013.01); *A61K 31/335* (2013.01); *A61K 31/351* (2013.01); *A61K 31/505* (2013.01); *A61K 31/506* (2013.01); *C07D 239/34* (2013.01); *C07D 239/47* (2013.01); *C07D 239/52* (2013.01); *C07D 239/60* (2013.01); *C07D 309/06* (2013.01); *C07D 309/10* (2013.01); *C07D 313/04* (2013.01); *C07D 401/12* (2013.01); *C07D 405/12* (2013.01); *C07D 417/12* (2013.01)

(58) Field of Classification Search
CPC . A61K 31/335; A61K 31/505; A61K 31/506; A61K 31/351; C07D 239/49; C07D 239/34; C07D 239/42; C07D 239/52; C07D 239/60; C07D 309/06; C07D 309/10; C07D 313/04

USPC .......................................... 514/275, 256, 460
See application file for complete search history.

(56) References Cited

U.S. PATENT DOCUMENTS

| | | |
|---|---|---|
| 2002/0013298 A1 | 1/2002 | Hunter |
| 2003/0130320 A1 | 7/2003 | Suzuki et al. |
| 2004/0235848 A1 | 11/2004 | Okuzumi et al. |

(Continued)

FOREIGN PATENT DOCUMENTS

| | | |
|---|---|---|
| EP | 1840121 | 10/2007 |
| JP | 2003-321358 | 11/2003 |

(Continued)

OTHER PUBLICATIONS

Baeumer W et al: AWD 12-281, "A highly selective phosphodiesterase 4 inhibitor, is effective in the prevention and treatment of inflammatory reactions in a model of allergic dermatitis" Journal of Pharmacy and Pharmacology, Royal Pharmaceutical society of Great Britain, GB, vol. 55, No. 8, Aug. 1, 2003, pp. 1107-1114, XP009019412 ISSN: 0022-3573.

(Continued)

*Primary Examiner* — Uma Ramachandran
(74) *Attorney, Agent, or Firm* — Pillsbury Winthrop Shaw Pittman LLP

(57) ABSTRACT

A therapeutic or prophylactic agent for allergic dermatitis is disclosed. The therapeutic or prophylactic agent comprises as an effective ingredient a glycine derivative having a specific structure or a pharmaceutically acceptable salt thereof, for example, the below-described compound [(E)-2-(2,6-dichlorobenzamido)-5-[4-(isopropyl-pyrimidin-2-ylamino)phenyl]pent-4-enoic acid]. The therapeutic or prophylactic agent for allergic dermatitis according to the present invention has high therapeutic or prophylactic effect.

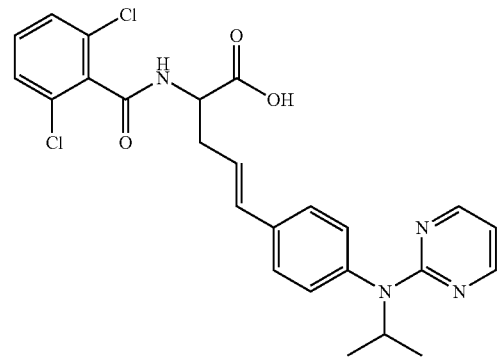

4 Claims, No Drawings

(51) Int. Cl.
*C07D 417/12* (2006.01)
*C07D 239/47* (2006.01)

(56) References Cited

U.S. PATENT DOCUMENTS

2004/0236147 A1 11/2004 Chiba et al.
2006/0123501 A1 6/2006 Korneluk et al.

FOREIGN PATENT DOCUMENTS

| WO | 01/70670 | 9/2001 |
| WO | 03/010135 | 2/2003 |
| WO | 03/053926 | 7/2003 |
| WO | 2006/068213 | 6/2006 |

OTHER PUBLICATIONS

Supplemental European Search Report in related application EP 07 74 5274 mailed Nov. 25, 2009.

Hanifin JM, Chan S, "Biochemical and immunologic mechanisms in atopic dermatitis: new targets for emerging therapies", J Am Acad Dermatol, Jul. 1999, 41(1):72-7.

Ardizzone S, Ianchi Porro G, "Inflammatory bowel disease: new insights into pathogenesis and treatment", J Intern Med. Dec. 2002, 252(6):475-96.

Ohmatsu, et al., Journal of Allergy Clinical Immunology, Dec. 2010, vol. 126, pp. 1267-1276.

Ludviksson, et al., Journal of Immunology, 1999, vol. 162, pp. 4975-4982.

Honda, Tetsuya, et al., "Update of Immune Events in the Murine Contact Hypersensitivity Model: Toward the Understanding of Allergic Contact Dermatitis", Journal of Investigative Dermatology, 2013, vol. 133, pp. 303-315.

Wittig, Bianca, et al., "Cutting Edge: Curative Treatment of an Experimentally Induced Coitis by a CD44 Variant V7-Specific Antibody", The Journal of Immunology, 1998, vol. 161, pp. 1069-1073.

Wittig, B, et al. "Functional Activity of Murine CD44 Variant Isoforms in Allergic and Delayed Type Hypersensitivity", Immunology Letters, 1997, vol. 57, pp. 217-223.

THERAPEUTIC OR PROPHYLACTIC AGENT FOR ALLERGIC DERMATITIS

CROSS REFERENCE TO RELATED APPLICATIONS

This Application is a Continuation of U.S. application Ser. No. 12/304,964, filed on Dec. 15, 2008, which is a U.S. National Phase of PCT/JP2007/062017, filed Jun. 14, 2007, which claims the benefit of Japanese Application No.: 2006-164520, filed Jun. 14, 2006, the contents of which are incorporated herein in their entirety by reference.

TECHNICAL FIELD

The present invention relates to a therapeutic or prophylactic agent for allergic dermatitis comprising as an effective ingredient a glycine derivative or a pharmaceutically acceptable salt thereof.

BACKGROUND ART

Allergic dermatitis is a recurrent eczematous lesion with chronic strong itching. Eruption is likely to occur on face, neck, flexural area such as elbow or knee, and in some cases eruption is exacerbated to spread systemically. Due to the environment with increased various allergens, the change in dietary life and the like, the number of patients suffering from allergic dermatitis is increasing and their symptoms tend to be more serious.

Therapy for allergic dermatitis is performed mainly by means of pharmacotherapy, and corticosteroids, immunosuppressants, antihistamines and the like are used. Although these agents can alleviate the symptoms or calm the inflammation, the effect is merely temporary. Moreover, it is known that corticosteroids and immunosuppressants may cause an infectious disease or serious side effects.

Thus, the therapeutic agents for allergic dermatitis now existing are not fully satisfactory with respect to effects thereof or reduction of side effects.

On the other hand, Patent Literature 1 discloses a use of the compounds represented by the below-described Formula:

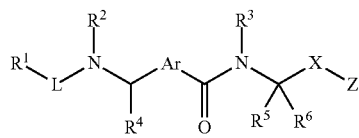

(wherein Ar represents substituted phenylene or the like, L represents —S(O)$_2$— or the like, X represents a bond or the like, Z represents COOH or the like, R$^2$, R$^3$ and R$^4$ represent hydrogen or the like, R$^5$ represents —C$_{2-10}$ alkenyl-aryl-NR-dRe-heteroaryl- (Rd, Re represent hydrogen or C$_{1-10}$ alkyl) or the like, R$^6$ represents hydrogen or the like), which may be considered to be structurally similar to the compounds contained as an effective ingredient in the present invention, for the therapy of asthma, allergic rhinitis, multiple sclerosis, arteriosclerosis, and inflammatory bowel disease. However, the compounds whose use mentioned above is disclosed in the publication are structurally different from the compounds in the present invention in that the disclosed compounds are characterized in that Ar in the Formula is substituted with aminoalkyl structure (R$^1$LN(R$^2$)CHR$^4$—: R$^1$ represents substituted aryl or the like). Moreover, the therapeutic or prophylactic effect on allergic dermatitis according to the present invention is not disclosed at all. Furthermore, practical data which demonstrate the therapeutic effect on asthma, allergic rhinitis, multiple sclerosis, arteriosclerosis, and inflammatory bowel disease are not described, therefore the publication fails to fully disclose that the compounds really have the effect mentioned therein.

In claims of Patent Literatures 2 and 3, use of the compounds represented by the Formula:

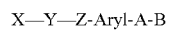

(wherein X represents a 6-membered aromatic ring comprising two nitrogen atoms or the like, Y represents —C$_{0-6}$ alkylene-NC$_{1-10}$ alkyl-C$_{0-6}$ alkylene- or the like, Z represents a bond or the like, Aryl represents a 6-membered aromatic ring, A represents —(CH$_2$)C═C(CH$_2$)$_n$— (wherein n=0-6) or the like, B represents —CH (substituted aryl-carbonylamino) CO$_2$H or the like), which includes the compounds in the present invention, as a bone resorption inhibitor and platelet aggregation inhibitor is described. However, the compounds in the present invention are not definitively described in the publications. The use disclosed therein is also totally different from that of the present invention. The therapeutic or prophylactic effect on allergic dermatitis according to the present invention is not suggested at all.

Patent Literature 4, which was published after the priority date of the present application, discloses a compound contained as an effective ingredient in the present invention and use thereof for therapy of inflammatory bowel disease. However, the therapeutic or prophylactic effect on allergic dermatitis according to the present invention is not disclosed at all.

Patent Literature 1: WO 99/26923

Patent Literature 2: WO 95/32710

Patent Literature 3: WO 94/12181

Patent Literature 4: WO 2006/068213

DISCLOSURE OF THE INVENTION

Problems which the Invention Tries to Solve

In view of the fact that development of a compound useful as a pharmaceutical for therapy or prophylaxis of allergic dermatitis is strongly demanded, an object of the present invention is to provide a therapeutic or prophylactic agent for allergic dermatitis comprising as an effective ingredient a low molecular compound or a pharmaceutically acceptable salt thereof which is useful as a pharmaceutical.

Means for Solving the Problem

The present inventors intensively studied to discover that the glycine derivatives represented by Formula (I) and pharmaceutically acceptable salts thereof have high oral absorbability and excellent in vivo stability, and are effective for the therapy or prophylaxis of allergic dermatitis, to complete the present invention.

That is, the present invention provides a therapeutic or prophylactic agent for allergic dermatitis comprising as an effective ingredient a compound of the Formula (I):

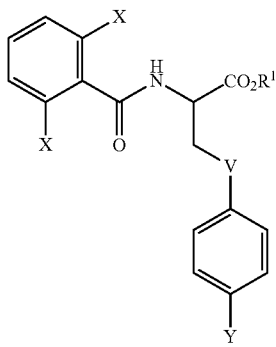

(I)

[wherein
$R^1$ represents hydrogen or $C_1$-$C_5$ alkyl;
Xs independently represent fluoro, chloro, bromo, iodo or $C_1$-$C_3$ alkyl;
V represents —CH=CH— or —C≡C—;
Y represents Formula (II) or Formula (III):

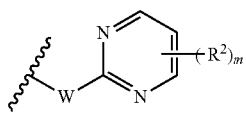

(II)

(III)

(wherein
$R^2$ represents $C_1$-$C_5$ alkyl or $C_1$-$C_3$ alkoxy;
$R^3$ represents hydrogen or $C_1$-$C_5$ alkyl;
m represents an integer of 0 to 3;
n represents 0 or 1;
p represents an integer of 0 to 2;
W represents —O— or —N($R^4$)—
(wherein
$R^4$ represents hydrogen, $C_1$-$C_5$ alkyl, $C_3$-$C_6$ alkenyl, phenyl, benzyl, benzyl substituted with one or two $R^5$s, tetrahydropyranyl, —($CH_2$)$_q$—O—$CH_3$, pyridylmethyl, —($CH_2$)$_q$—CN, $C_4$-$C_7$ cycloalkylmethyl or thiazol-4-ylmethyl;
$R^5$ represents hydroxy or $C_1$-$C_3$ alkoxy; and
q represents an integer of 1 to 3))]
or a pharmaceutically acceptable salt thereof. The present invention also provides a use of the compound of the Formula (I) or the pharmaceutically acceptable salt thereof according to the present invention described above for the production of a therapeutic or prophylactic agent for allergic dermatitis. The present invention further provides a therapeutic or prophylactic method for allergic dermatitis, comprising administering to a patient an effective amount of the compound of the Formula (I) or the pharmaceutically acceptable salt thereof according to the present invention described above.

Effects of the Invention

The therapeutic or prophylactic agents for allergic dermatitis according to the present invention have excellent oral absorbability and in vivo stability, and therefore exhibit high therapeutic or prophylactic effects.

BEST MODE FOR CARRYING OUT THE INVENTION

The term "alkyl" means a straight or branched hydrocarbon chain. Examples of alkyl include methyl, ethyl, propyl, isopropyl, butyl and isobutyl.

The term "alkoxy" means an oxygen atom having an alkyl substituent. Examples of alkoxy include methoxy, ethoxy, propoxy, isopropoxy and butoxy.

The term "alkenyl" means a straight or branched hydrocarbon chain having one or more carbon-carbon double bond. Examples of alkenyl include vinyl, allyl, isopropenyl, butenyl and pentenyl.

The term "cycloalkyl" means a monocyclic saturated hydrocarbon ring. Examples of cycloalkyl include cyclopropyl, cyclobutyl, cyclopentyl and cyclohexyl.

The term "cycloalkylmethyl" means a methyl group having a cycloalkyl group. Examples of cycloalkylmethyl include cyclopropylmethyl, cyclobutylmethyl, cyclopentylmethyl and cyclohexylmethyl.

As for the compounds represented by the above-described Formula (I), preferred modes are as follows:

As the "X", fluoro, chloro or methyl is preferred, and chloro or methyl is especially preferred.

As the "V", —CH=CH— is preferred, and trans form —CH=CH— is especially preferred.

As the "$R^1$", hydrogen, methyl or tert-butyl is preferred, and hydrogen is especially preferred.

In the "Y" structures represented by the above-described Formula (II) or (III):

As the "W", —N($R^4$)— is preferred.

As the "$R^2$" when it exists, methyl, ethyl or methoxy is preferred, and methyl is especially preferred.

As the "$R^3$", hydrogen or $C_1$-$C_3$ alkyl (e.g., methyl, ethyl or propyl) is preferred, and methyl is especially preferred.

As the "$R^4$", $C_1$-$C_3$ alkyl (e.g., methyl, ethyl, propyl or isopropyl), cyanoethyl, tetrahydropyranyl or phenyl is preferred, and methyl or isopropyl is especially preferred.

As the "m", an integer of 0 to 2 is preferred, and 0 is especially preferred.

As the "n", 0 is preferred.

As the "p", 1 or 2 is preferred, and 1 is especially preferred.

The wavy line in Formulae (II) and (III) represents the moiety in the compound, to which the group represented by Formula (II) or (III) is bound.

Especially, (1) the compounds represented by Formula (I), wherein
V is —CH=CH—;
when Y is represented by Formula (II), m is 0;
when Y is represented by Formula (III), p is 1;
and pharmaceutically acceptable salts thereof are preferred. Among these, (2) the compounds represented by Formula (I), wherein
$R^1$ is hydrogen;
when Y is represented by Formula (II), W is —N($R^4$)— and $R^4$ is $C_1$-$C_3$ alkyl, cyanoethyl, tetrahydropyranyl or phenyl;
when Y is represented by Formula (III), n is 0 and $R^3$ is $C_1$-$C_3$ alkyl;
and pharmaceutically acceptable salts thereof are more preferred. Among these, (3) the compounds represented by Formula (I), wherein
Xs are independently chloro or methyl;
V is trans form —CH=CH—;

when Y is represented by Formula (II), W is —N(R⁴)— and R⁴ is methyl or isopropyl;

when Y is represented by Formula (III), R³ is methyl, and pharmaceutically acceptable salts thereof are more preferred.

Examples of the pharmaceutically acceptable salts of the compounds represented by Formula (I) include, for acidic group(s) such as carboxylic group in the formula, ammonium salt; salts of alkaline metals such as sodium and potassium; salts of alkaline earth metals such as calcium and magnesium; aluminum salt; zinc salt; salts of organic amines or the like such as triethylamine, ethanolamine, morpholine, piperidine and dicyclohexylamine; and salts of basic amino acids such as arginine and lysine. In cases where a basic group(s) exist(s) in the formula, examples of the pharmaceutically acceptable salts of the compounds include, for the basic group(s), salts of inorganic acids such as hydrochloric acid, sulfuric acid, nitric acid, hydrobromic acid and phosphoric acid; salts of organic carboxylic acids such as acetic acid, lactic acid, citric acid, maleic acid, benzoic acid, oxalic acid, glutaric acid, malic acid, tartaric acid, fumaric acid, mandelic acid and succinic acid; and salts of organic sulfonic acids such as methanesulfonic acid, p-toluenesulfonic acid and camphor sulfonic acid.

The structure represented by Formula (I) includes optical isomers represented by Formula (IV) and (V) based on the asymmetric carbon atom, the present invention includes these isomers and mixtures thereof. Further, in the structure represented by Formula (I), in cases where Y has an asymmetric carbon atom, the present invention include the isomers based on the asymmetric carbon atom and mixtures thereof.

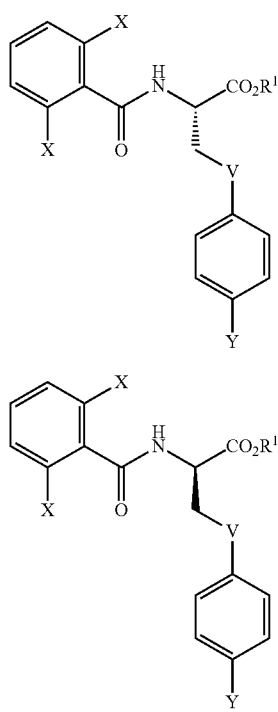

Among the ingredients of the therapeutic or prophylactic agents for allergic dermatitis according to the present invention, preferred ingredients include compounds represented by Formula (Ia) or (Ib). Specific examples of the compounds represented by Formula (Ia) or (Ib) are shown in Tables 1 to 5.

TABLE 1

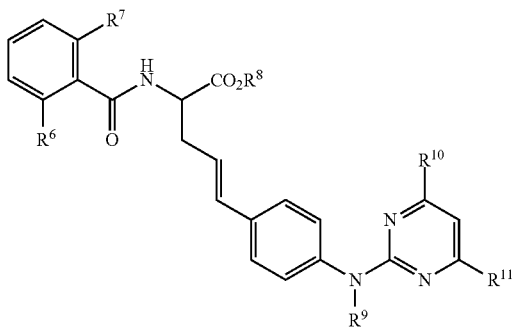

(Ia)

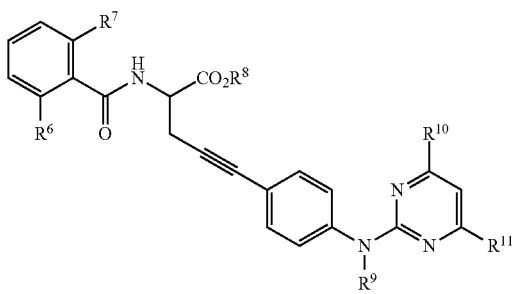

(Ib)

| $R^6$ | $R^7$ | $R^8$ | $R^9$ | $R^{10}$ | $R^{11}$ |
| --- | --- | --- | --- | --- | --- |
| —Cl | —Cl | —H | —Me | —H | —H |
| —Cl | —Me | —H | —Me | —H | —H |
| —Me | —Me | —H | —Me | —H | —H |
| —Cl | —Cl | —H | —Me | —H | —Me |
| —Cl | —Me | —H | —Me | —H | —Me |
| —Me | —Me | —H | —Me | —H | —Me |
| —Cl | —Cl | —H | —Me | —Me | —Me |
| —Cl | —Me | —H | —Me | —Me | —Me |
| —Me | —Me | —H | —Me | —Me | —Me |
| —Cl | —Cl | —H | —Et | —H | —H |
| —Cl | —Me | —H | —Et | —H | —H |
| —Me | —Me | —H | —Et | —H | —H |
| —Cl | —Cl | —H | —Et | —H | —Me |
| —Cl | —Me | —H | —Et | —H | —Me |
| —Me | —Me | —H | —Et | —H | —Me |
| —Cl | —Cl | —H | —Et | —Me | —Me |
| —Cl | —Me | —H | —Et | —Me | —Me |
| —Me | —Me | —H | —Et | —Me | —Me |
| —Cl | —Cl | —H | —$^n$Pr | —H | —H |
| —Cl | —Me | —H | —$^n$Pr | —H | —H |
| —Me | —Me | —H | —$^n$Pr | —H | —H |
| —Cl | —Cl | —H | —$^n$Pr | —H | —Me |
| —Cl | —Me | —H | —$^n$Pr | —H | —Me |
| —Me | —Me | —H | —$^n$Pr | —H | —Me |
| —Cl | —Cl | —H | —$^n$Pr | —Me | —Me |
| —Cl | —Me | —H | —$^n$Pr | —Me | —Me |
| —Me | —Me | —H | —$^n$Pr | —Me | —Me |
| —Cl | —Cl | —H | —$^i$Pr | —H | —H |
| —Cl | —Me | —H | —$^i$Pr | —H | —H |
| —Me | —Me | —H | —$^i$Pr | —H | —H |
| —Cl | —Cl | —H | —$^i$Pr | —H | —Me |
| —Cl | —Me | —H | —$^i$Pr | —H | —Me |
| —Me | —Me | —H | —$^i$Pr | —H | —Me |
| —Cl | —Cl | —H | —$^i$Pr | —Me | —Me |
| —Cl | —Me | —H | —$^i$Pr | —Me | —Me |
| —Me | —Me | —H | —$^i$Pr | —Me | —Me |

TABLE 2

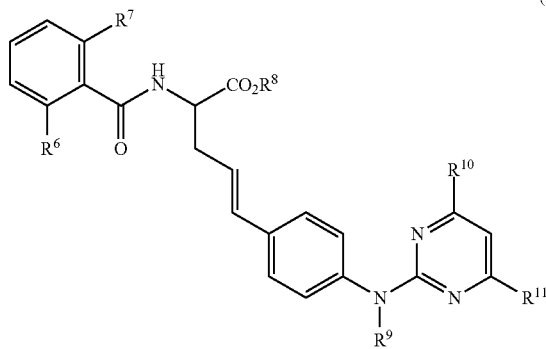
(Ia)

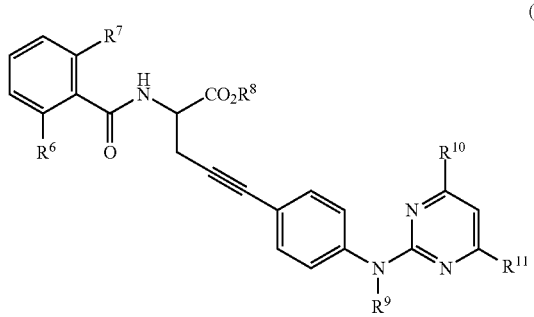
(Ib)

| $R^6$ | $R^7$ | $R^8$ | $R^9$ | $R^{10}$ | $R^{11}$ |
|---|---|---|---|---|---|
| —Cl | —Cl | —H | —(CH$_2$)$_2$CN | —H | —H |
| —Cl | —Me | —H | —(CH$_2$)$_2$CN | —H | —H |
| —Me | —Me | —H | —(CH$_2$)$_2$CN | —H | —H |
| —Cl | —Cl | —H | —(CH$_2$)$_2$CN | —H | —Me |
| —Cl | —Me | —H | —(CH$_2$)$_2$CN | —H | —Me |
| —Me | —Me | —H | —(CH$_2$)$_2$CN | —H | —Me |
| —Cl | —Cl | —H | —(CH$_2$)$_2$CN | —Me | —Me |
| —Cl | —Me | —H | —(CH$_2$)$_2$CN | —Me | —Me |
| —Me | —Me | —H | —(CH$_2$)$_2$CN | —Me | —Me |
| —Cl | —Cl | —H | 4-tetrahydropyranyl | —H | —H |
| —Cl | —Me | —H | 4-tetrahydropyranyl | —H | —H |
| —Me | —Me | —H | 4-tetrahydropyranyl | —H | —H |
| —Cl | —Cl | —H | 4-tetrahydropyranyl | —H | —Me |
| —Cl | —Me | —H | 4-tetrahydropyranyl | —H | —Me |
| —Me | —Me | —H | 4-tetrahydropyranyl | —H | —Me |
| —Cl | —Cl | —H | 4-tetrahydropyranyl | —Me | —Me |
| —Cl | —Me | —H | 4-tetrahydropyranyl | —Me | —Me |
| —Me | —Me | —H | 4-tetrahydropyranyl | —Me | —Me |
| —Cl | —Cl | —Me | —Me | —H | —H |
| —Cl | —Me | —Me | —Me | —H | —H |
| —Me | —Me | —Me | —Me | —H | —H |
| —Cl | —Cl | —Me | —Me | —H | —Me |
| —Cl | —Me | —Me | —Me | —H | —Me |
| —Me | —Me | —Me | —Me | —H | —Me |
| —Cl | —Cl | —Me | —Me | —Me | —Me |
| —Cl | —Me | —Me | —Me | —Me | —Me |
| —Me | —Me | —Me | —Me | —Me | —Me |
| —Cl | —Cl | —Me | —Et | —H | —H |
| —Cl | —Me | —Me | —Et | —H | —H |
| —Me | —Me | —Me | —Et | —H | —H |
| —Cl | —Cl | —Me | —Et | —H | —Me |
| —Cl | —Me | —Me | —Et | —H | —Me |
| —Me | —Me | —Me | —Et | —H | —Me |
| —Cl | —Cl | —Me | —Et | —Me | —Me |
| —Cl | —Me | —Me | —Et | —Me | —Me |
| —Me | —Me | —Me | —Et | —Me | —Me |

TABLE 3

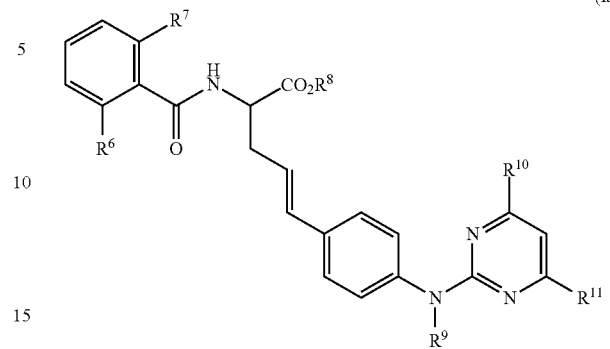
(Ia)

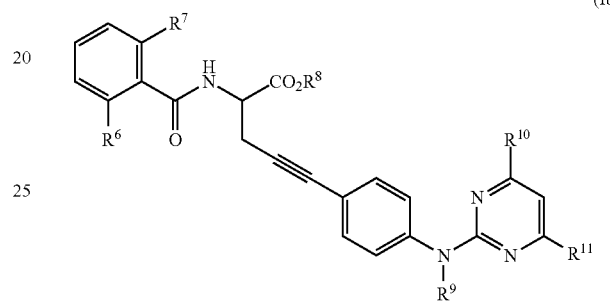
(Ib)

| $R^6$ | $R^7$ | $R^8$ | $R^9$ | $R^{10}$ | $R^{11}$ |
|---|---|---|---|---|---|
| —Cl | —Cl | —Me | —$^n$Pr | —H | —H |
| —Cl | —Me | —Me | —$^n$Pr | —H | —H |
| —Me | —Me | —Me | —$^n$Pr | —H | —H |
| —Cl | —Cl | —Me | —$^n$Pr | —H | —Me |
| —Cl | —Me | —Me | —$^n$Pr | —H | —Me |
| —Me | —Me | —Me | —$^n$Pr | —H | —Me |
| —Cl | —Cl | —Me | —$^n$Pr | —Me | —Me |
| —Cl | —Me | —Me | —$^n$Pr | —Me | —Me |
| —Me | —Me | —Me | —$^n$Pr | —Me | —Me |
| —Cl | —Cl | —Me | —$^i$Pr | —H | —H |
| —Cl | —Me | —Me | —$^i$Pr | —H | —H |
| —Me | —Me | —Me | —$^i$Pr | —H | —H |
| —Cl | —Cl | —Me | —$^i$Pr | —H | —Me |
| —Cl | —Me | —Me | —$^i$Pr | —H | —Me |
| —Me | —Me | —Me | —$^i$Pr | —H | —Me |
| —Cl | —Cl | —Me | —$^i$Pr | —Me | —Me |
| —Cl | —Me | —Me | —$^i$Pr | —Me | —Me |
| —Me | —Me | —Me | —$^i$Pr | —Me | —Me |
| —Cl | —Cl | —Me | —(CH$_2$)$_2$CN | —H | —H |
| —Cl | —Me | —Me | —(CH$_2$)$_2$CN | —H | —H |
| —Me | —Me | —Me | —(CH$_2$)$_2$CN | —H | —H |
| —Cl | —Cl | —Me | —(CH$_2$)$_2$CN | —H | —Me |
| —Cl | —Me | —Me | —(CH$_2$)$_2$CN | —H | —Me |
| —Me | —Me | —Me | —(CH$_2$)$_2$CN | —H | —Me |
| —Cl | —Cl | —Me | —(CH$_2$)$_2$CN | —Me | —Me |
| —Cl | —Me | —Me | —(CH$_2$)$_2$CN | —Me | —Me |
| —Me | —Me | —Me | —(CH$_2$)$_2$CN | —Me | —Me |
| —Cl | —Cl | —Me | 4-tetrahydropyranyl | —H | —H |
| —Cl | —Me | —Me | 4-tetrahydropyranyl | —H | —H |
| —Me | —Me | —Me | 4-tetrahydropyranyl | —H | —H |
| —Cl | —Cl | —Me | 4-tetrahydropyranyl | —H | —Me |
| —Cl | —Me | —Me | 4-tetrahydropyranyl | —H | —Me |
| —Me | —Me | —Me | 4-tetrahydropyranyl | —H | —Me |
| —Cl | —Cl | —Me | 4-tetrahydropyranyl | —Me | —Me |
| —Cl | —Me | —Me | 4-tetrahydropyranyl | —Me | —Me |
| —Me | —Me | —Me | 4-tetrahydropyranyl | —Me | —Me |

TABLE 4

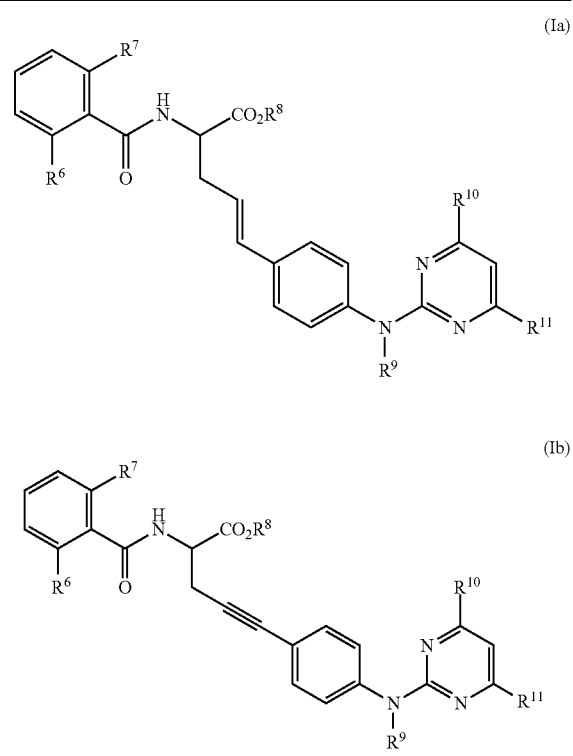

| R⁶ | R⁷ | R⁸ | R⁹ | R¹⁰ | R¹¹ |
|---|---|---|---|---|---|
| —Cl | —Cl | —$^t$Bu | —Me | —H | —H |
| —Cl | —Me | —$^t$Bu | —Me | —H | —H |
| —Me | —Me | —$^t$Bu | —Me | —H | —H |
| —Cl | —Cl | —$^t$Bu | —Me | —H | —Me |
| —Cl | —Me | —$^t$Bu | —Me | —H | —Me |
| —Me | —Me | —$^t$Bu | —Me | —H | —Me |
| —Cl | —Cl | —$^t$Bu | —Me | —Me | —Me |
| —Cl | —Me | —$^t$Bu | —Me | —Me | —Me |
| —Me | —Me | —$^t$Bu | —Me | —Me | —Me |
| —Cl | —Cl | —$^t$Bu | —Et | —H | —H |
| —Cl | —Me | —$^t$Bu | —Et | —H | —H |
| —Me | —Me | —$^t$Bu | —Et | —H | —H |
| —Cl | —Cl | —$^t$Bu | —Et | —H | —Me |
| —Cl | —Me | —$^t$Bu | —Et | —H | —Me |
| —Me | —Me | —$^t$Bu | —Et | —H | —Me |
| —Cl | —Cl | —$^t$Bu | —Et | —Me | —Me |
| —Cl | —Me | —$^t$Bu | —Et | —Me | —Me |
| —Me | —Me | —$^t$Bu | —Et | —Me | —Me |
| —Cl | —Cl | —$^t$Bu | —$^n$Pr | —H | —H |
| —Cl | —Me | —$^t$Bu | —$^n$Pr | —H | —H |
| —Me | —Me | —$^t$Bu | —$^n$Pr | —H | —H |
| —Cl | —Cl | —$^t$Bu | —$^n$Pr | —H | —Me |
| —Cl | —Me | —$^t$Bu | —$^n$Pr | —H | —Me |
| —Me | —Me | —$^t$Bu | —$^n$Pr | —H | —Me |
| —Cl | —Cl | —$^t$Bu | —$^n$Pr | —Me | —Me |
| —Cl | —Me | —$^t$Bu | —$^n$Pr | —Me | —Me |
| —Me | —Me | —$^t$Bu | —$^n$Pr | —Me | —Me |
| —Cl | —Cl | —$^t$Bu | —$^i$Pr | —H | —H |
| —Cl | —Me | —$^t$Bu | —$^i$Pr | —H | —H |
| —Me | —Me | —$^t$Bu | —$^i$Pr | —H | —H |
| —Cl | —Cl | —$^t$Bu | —$^i$Pr | —H | —Me |
| —Cl | —Me | —$^t$Bu | —$^i$Pr | —H | —Me |
| —Me | —Me | —$^t$Bu | —$^i$Pr | —H | —Me |
| —Cl | —Cl | —$^t$Bu | —$^i$Pr | —Me | —Me |
| —Cl | —Me | —$^t$Bu | —$^i$Pr | —Me | —Me |
| —Me | —Me | —$^t$Bu | —$^i$Pr | —Me | —Me |

TABLE 5

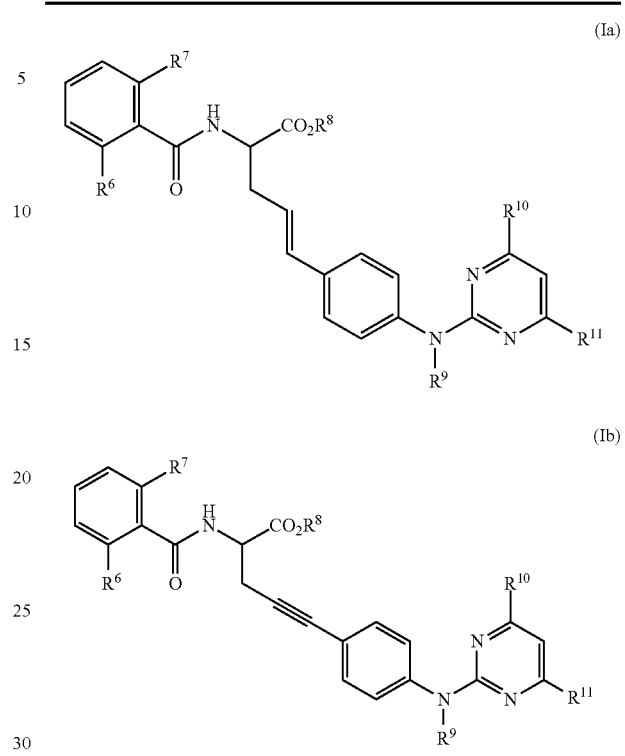

| R⁶ | R⁷ | R⁸ | R⁹ | R¹⁰ | R¹¹ |
|---|---|---|---|---|---|
| —Cl | —Cl | —$^t$Bu | —(CH$_2$)$_2$CN | —H | —H |
| —Cl | —Me | —$^t$Bu | —(CH$_2$)$_2$CN | —H | —H |
| —Me | —Me | —$^t$Bu | —(CH$_2$)$_2$CN | —H | —H |
| —Cl | —Cl | —$^t$Bu | —(CH$_2$)$_2$CN | —H | —Me |
| —Cl | —Me | —$^t$Bu | —(CH$_2$)$_2$CN | —H | —Me |
| —Me | —Me | —$^t$Bu | —(CH$_2$)$_2$CN | —H | —Me |
| —Cl | —Cl | —$^t$Bu | —(CH$_2$)$_2$CN | —Me | —Me |
| —Cl | —Me | —$^t$Bu | —(CH$_2$)$_2$CN | —Me | —Me |
| —Me | —Me | —$^t$Bu | —(CH$_2$)$_2$CN | —Me | —Me |
| —Cl | —Cl | —$^t$Bu | 4-tetrahydropyranyl | —H | —H |
| —Cl | —Me | —$^t$Bu | 4-tetrahydropyranyl | —H | —H |
| —Me | —Me | —$^t$Bu | 4-tetrahydropyranyl | —H | —H |
| —Cl | —Cl | —$^t$Bu | 4-tetrahydropyranyl | —H | —Me |
| —Cl | —Me | —$^t$Bu | 4-tetrahydropyranyl | —H | —Me |
| —Me | —Me | —$^t$Bu | 4-tetrahydropyranyl | —H | —Me |
| —Cl | —Cl | —$^t$Bu | 4-tetrahydropyranyl | —Me | —Me |
| —Cl | —Me | —$^t$Bu | 4-tetrahydropyranyl | —Me | —Me |
| —Me | —Me | —$^t$Bu | 4-tetrahydropyranyl | —Me | —Me |

The symbol "-$^t$Bu" shown in Tables 4 and 5 represents tert-butyl group; the symbol "-$^n$Pr" shown in Tables 1, 3 and 4 represents normal propyl group; and the symbol "-$^i$Pr" shown in Tables 1, 3 and 4 represents isopropyl group. The compounds shown in Tables 1 to 5 include pharmaceutically acceptable salts thereof.

Among the ingredients of the therapeutic or prophylactic agents for allergic dermatitis according to the present invention, preferred ingredients also include compounds represented by Formula (Ic) or (Id). Specific examples of the compounds represented by Formula (Ic) or (Id) are shown in Tables 6 and 7.

TABLE 6

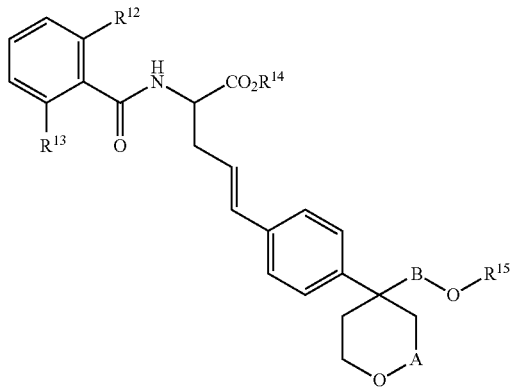

(Ic)

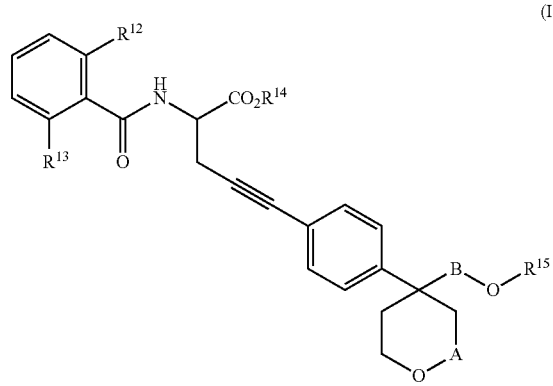

(Id)

| $R^{12}$ | $R^{13}$ | $R^{14}$ | $R^{15}$ | A | B |
|---|---|---|---|---|---|
| —Cl | —Cl | —H | —Me | —CH$_2$— | bond |
| —Cl | —Me | —H | —Me | —CH$_2$— | bond |
| —Me | —Me | —H | —Me | —CH$_2$— | bond |
| —Cl | —Cl | —H | —Me | —CH$_2$—CH$_2$— | bond |
| —Cl | —Me | —H | —Me | —CH$_2$—CH$_2$— | bond |
| —Me | —Me | —H | —Me | —CH$_2$—CH$_2$— | bond |
| —Cl | —Cl | —H | —Me | —CH$_2$— | —CH$_2$— |
| —Cl | —Me | —H | —Me | —CH$_2$— | —CH$_2$— |
| —Me | —Me | —H | —Me | —CH$_2$— | —CH$_2$— |
| —Cl | —Cl | —H | —Me | —CH$_2$—CH$_2$— | —CH$_2$— |
| —Cl | —Me | —H | —Me | —CH$_2$—CH$_2$— | —CH$_2$— |
| —Me | —Me | —H | —Me | —CH$_2$—CH$_2$— | —CH$_2$— |
| —Cl | —Cl | —H | —Et | —CH$_2$— | bond |
| —Cl | —Me | —H | —Et | —CH$_2$— | bond |
| —Me | —Me | —H | —Et | —CH$_2$— | bond |
| —Cl | —Cl | —H | —Et | —CH$_2$—CH$_2$— | bond |
| —Cl | —Me | —H | —Et | —CH$_2$—CH$_2$— | bond |
| —Me | —Me | —H | —Et | —CH$_2$—CH$_2$— | bond |
| —Cl | —Cl | —H | —Et | —CH$_2$— | —CH$_2$— |
| —Cl | —Me | —H | —Et | —CH$_2$— | —CH$_2$— |
| —Me | —Me | —H | —Et | —CH$_2$— | —CH$_2$— |
| —Cl | —Cl | —H | —Et | —CH$_2$—CH$_2$— | —CH$_2$— |
| —Cl | —Me | —H | —Et | —CH$_2$—CH$_2$— | —CH$_2$— |
| —Me | —Me | —H | —Et | —CH$_2$—CH$_2$— | —CH$_2$— |
| —Cl | —Cl | —Me | —Me | —CH$_2$— | bond |
| —Cl | —Me | —Me | —Me | —CH$_2$— | bond |
| —Me | —Me | —Me | —Me | —CH$_2$— | bond |
| —Cl | —Cl | —Me | —Me | —CH$_2$—CH$_2$— | bond |
| —Cl | —Me | —Me | —Me | —CH$_2$—CH$_2$— | bond |
| —Me | —Me | —Me | —Me | —CH$_2$—CH$_2$— | bond |
| —Cl | —Cl | —Me | —Me | —CH$_2$— | —CH$_2$— |
| —Cl | —Me | —Me | —Me | —CH$_2$— | —CH$_2$— |
| —Me | —Me | —Me | —Me | —CH$_2$— | —CH$_2$— |
| —Cl | —Cl | —Me | —Me | —CH$_2$—CH$_2$— | —CH$_2$— |
| —Cl | —Me | —Me | —Me | —CH$_2$—CH$_2$— | —CH$_2$— |
| —Me | —Me | —Me | —Me | —CH$_2$—CH$_2$— | —CH$_2$— |

TABLE 7

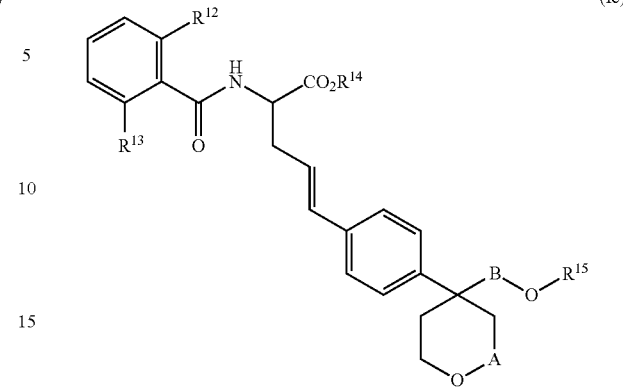

(Ic)

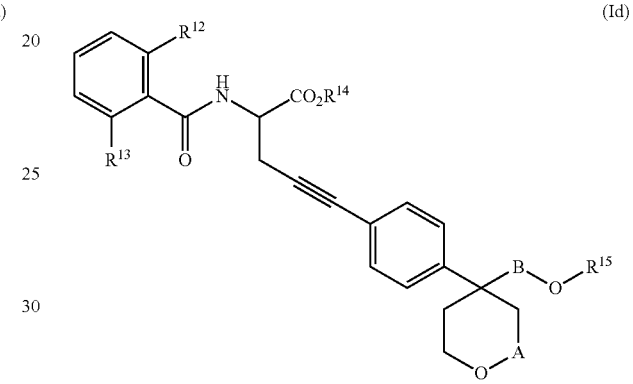

(Id)

| $R^{12}$ | $R^{13}$ | $R^{14}$ | $R^{15}$ | A | B |
|---|---|---|---|---|---|
| —Cl | —Cl | —Me | —Et | —CH$_2$— | bond |
| —Cl | —Me | —Me | —Et | —CH$_2$— | bond |
| —Me | —Me | —Me | —Et | —CH$_2$— | bond |
| —Cl | —Cl | —Me | —Et | —CH$_2$—CH$_2$— | bond |
| —Cl | —Me | —Me | —Et | —CH$_2$—CH$_2$— | bond |
| —Me | —Me | —Me | —Et | —CH$_2$—CH$_2$— | bond |
| —Cl | —Cl | —Me | —Et | —CH$_2$— | —CH$_2$— |
| —Cl | —Me | —Me | —Et | —CH$_2$— | —CH$_2$— |
| —Me | —Me | —Me | —Et | —CH$_2$— | —CH$_2$— |
| —Cl | —Cl | —Me | —Et | —CH$_2$—CH$_2$— | —CH$_2$— |
| —Cl | —Me | —Me | —Et | —CH$_2$—CH$_2$— | —CH$_2$— |
| —Me | —Me | —Me | —Et | —CH$_2$—CH$_2$— | —CH$_2$— |
| —Cl | —Cl | —$^t$Bu | —Me | —CH$_2$— | bond |
| —Cl | —Me | —$^t$Bu | —Me | —CH$_2$— | bond |
| —Me | —Me | —$^t$Bu | —Me | —CH$_2$— | bond |
| —Cl | —Cl | —$^t$Bu | —Me | —CH$_2$—CH$_2$— | bond |
| —Cl | —Me | —$^t$Bu | —Me | —CH$_2$—CH$_2$— | bond |
| —Me | —Me | —$^t$Bu | —Me | —CH$_2$—CH$_2$— | bond |
| —Cl | —Cl | —$^t$Bu | —Me | —CH$_2$— | —CH$_2$— |
| —Cl | —Me | —$^t$Bu | —Me | —CH$_2$— | —CH$_2$— |
| —Me | —Me | —$^t$Bu | —Me | —CH$_2$— | —CH$_2$— |
| —Cl | —Cl | —$^t$Bu | —Me | —CH$_2$—CH$_2$— | —CH$_2$— |
| —Cl | —Me | —$^t$Bu | —Me | —CH$_2$—CH$_2$— | —CH$_2$— |
| —Me | —Me | —$^t$Bu | —Me | —CH$_2$—CH$_2$— | —CH$_2$— |
| —Cl | —Cl | —$^t$Bu | —Et | —CH$_2$— | bond |
| —Cl | —Me | —$^t$Bu | —Et | —CH$_2$— | bond |
| —Me | —Me | —$^t$Bu | —Et | —CH$_2$— | bond |
| —Cl | —Cl | —$^t$Bu | —Et | —CH$_2$—CH$_2$— | bond |
| —Cl | —Me | —$^t$Bu | —Et | —CH$_2$—CH$_2$— | bond |
| —Me | —Me | —$^t$Bu | —Et | —CH$_2$—CH$_2$— | bond |
| —Cl | —Cl | —$^t$Bu | —Et | —CH$_2$— | —CH$_2$— |
| —Cl | —Me | —$^t$Bu | —Et | —CH$_2$— | —CH$_2$— |
| —Me | —Me | —$^t$Bu | —Et | —CH$_2$— | —CH$_2$— |
| —Cl | —Cl | —$^t$Bu | —Et | —CH$_2$—CH$_2$— | —CH$_2$— |
| —Cl | —Me | —$^t$Bu | —Et | —CH$_2$—CH$_2$— | —CH$_2$— |
| —Me | —Me | —$^t$Bu | —Et | —CH$_2$—CH$_2$— | —CH$_2$— |

The symbol "-$^t$Bu" shown in Table 7 represents tert-butyl group, and the symbol "bond" shown in Tables 6 and 7 represents valence bond. The compounds shown in Tables 6 and 7 include pharmaceutically acceptable salts thereof.

The compounds represented by Formula (I) or the pharmaceutically acceptable salts thereof which are comprised as an effective ingredient in the therapeutic or prophylactic agents for allergic dermatitis according to the present invention can be synthesized by the following steps:

Conversion of the compounds represented by the following Formula (VI):

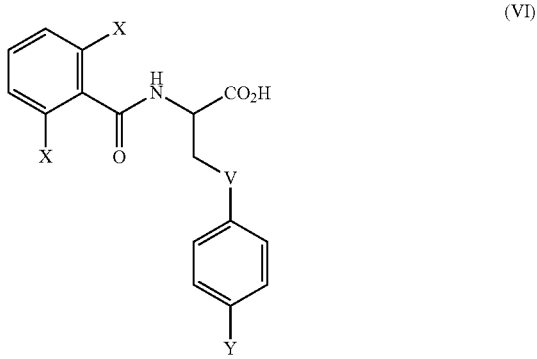

(VI)

(wherein the symbols have the same meanings as described above):
to a pharmaceutically acceptable salt thereof can be attained by a conventional method using a base (inorganic base such as sodium hydroxide; organic base such as triethylamine; or basic amino acid such as lysine) or an acid (acetic acid; inorganic acid such as nitric acid or sulfuric acid; organic acid such as acetic acid or maleic acid; organic sulfonic acid such as p-toluenesulfonic acid; acidic amino acid such as aspartic acid).

The compounds of Formula (VI) can be obtained by converting the esterified carboxyl group $CO_2R^{16}$ of a compound of the Formula (VII):

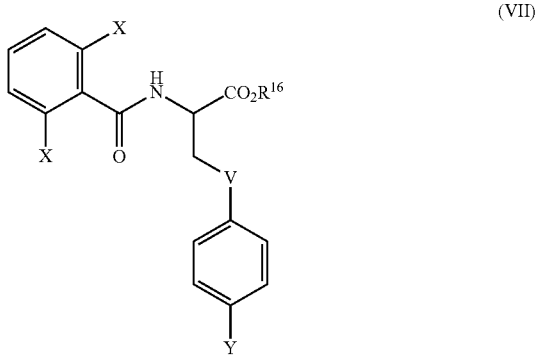

(VII)

[wherein $R^{16}$ represents $C_1$-$C_5$ alkyl, and other symbols have the same meanings as described above]
to carboxyl group.

Conversion of the esterified carboxyl group $CO_2R^{16}$ to carboxyl group may be attained by a conventional method such as hydrolysis using a base (alkaline metal hydroxide such as lithium hydroxide, sodium hydroxide, barium hydroxide) or an acid (such as hydrochloric acid), or acid (e.g. trifluoroacetic acid) treatment. The amount of the base used is usually 0.9 to 100 equivalents, preferably 0.9 to 10.0 equivalents with respect to the compound of Formula (VII). The amount of the acid used is usually 1.0 equivalent with respect to the compound of Formula (VII) to an excess amount used as a solvent, preferably 1.0 to 100 equivalents with respect to the compound of Formula (VII).

Examples of the solvent include aprotic bipolar solvents such as DMF and DMSO; ether solvents such as diethyl ether, THF and DME; alcoholic solvents such as methanol and ethanol; halogen-containing solvents such as dichloromethane, chloroform, carbon tetrachloride and 1,2-dichloroethane; water; and mixtures thereof. Among these, DMF, THF, methanol, ethanol or water is preferably used. The reaction temperature is thought to be −30° C. to 200° C. In case of hydrolysis using a base, the reaction temperature is preferably −20° C. to 60° C., more preferably −10° C. to 40° C. In case of hydrolysis using an acid, the reaction temperature is preferably 0° C. to 180° C., more preferably 0° C. to 100° C. The reaction time may appropriately be selected depending on the conditions such as reaction temperature, and satisfactory results are usually obtained by selecting a reaction time between about 1 minute and hours.

The compounds of Formula (VII) may be synthesized by the following method (Method A or Method B) depending on the structure of "V" (V has the same meaning as described above) in Formula (I):
Method A: In cases where V is —CH═CH—

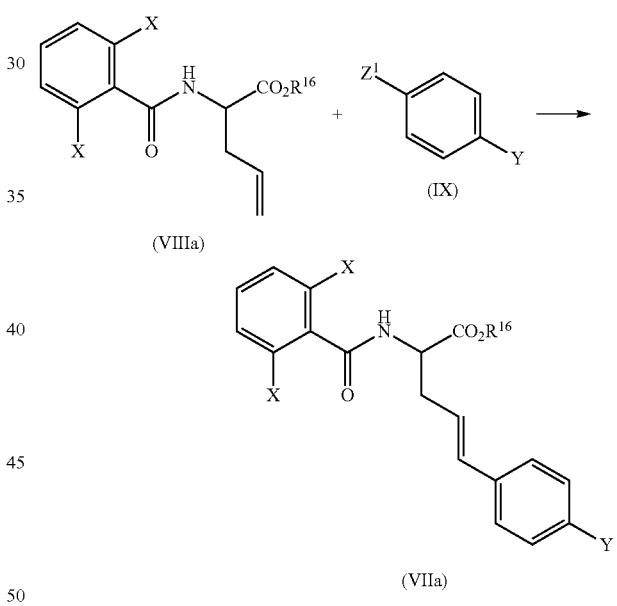

[wherein $Z^1$ represents a leaving group such as halogen atom or trifluoromethanesulfonyloxy group, and the other symbols have the same meanings as described above]

The compounds of Formula (VIIa) can be synthesized by coupling a compound of Formula (VIIIa) with a compound of Formula (IX).

The coupling reaction is carried out in the presence of a palladium catalyst and a base, and in the presence or absence of a phosphine ligand, in an appropriate solvent.

The compound of Formula (IX) is used in an amount of 1.0 to 10 equivalents, preferably 1.0 to 4.0 equivalents with respect to the compound of Formula (VIIIa).

Examples of the palladium catalyst include palladium acetate, tetrakis(triphenylphosphine)palladium, bis(triphenylphosphine)palladium dichloride, palladium(I) chloride, bis(dibenzylideneacetone)palladium, and bis(diphenylphosphino) ferrocene palladium dichloride. Among these, palladium acetate, tetrakis(triphenylphosphine)palladium or bis(dibenzylideneacetone)palladium is preferably used. The amount of the palladium catalyst used is 0.001 to 1 equivalent, preferably 0.01 to 0.2 equivalents with respect to the compound of Formula (VIIIa).

Examples of the base include potassium carbonate, potassium phosphate, cesium carbonate, sodium hydroxide, potassium hydroxide, sodium-tert-butoxide, triethylamine, diisopropylamine, diisopropylethylamine and n-butylamine. Among these, potassium carbonate or potassium phosphate is preferably used. The amount of the base used is 1 to 10 equivalents, preferably 1 to 4 equivalents with respect to the compound of Formula (VIIIa).

Examples of the phosphine ligand include triphenylphosphine, tris(2-methylphenyl)phosphine, tributylphosphine, triethylphosphine, tri-tert-butylphosphine, 2,2'-bis(diphenylphosphino)-1,1'-biphenyl, 2-(di-tert-butylphosphino)-1,1'-binaphthyl, 2-(dicyclohexylphosphino)diphenyl and 9,9-dimethyl-4,5-bis(diphenylphosphino)xanthene. Among these, tributylphosphine, tris(2-methylphenyl)phosphine or 9,9-dimethyl-4,5-bis(diphenylphosphino)xanthene is preferably used. The amount of the phosphine ligand used is 0.001 to 1 equivalent, preferably 0.01 to 0.2 equivalents with respect to the compound of Formula (VIIa).

Examples of the solvent include aprotic bipolar solvents such as DMF, DMSO and NMP; ether solvents such as THF, DME and dioxane; alcoholic solvents such as methanol and ethanol; halogen-containing solvents such as dichloromethane, chloroform, carbon tetrachloride and 1,2-dichloroethane; aromatic solvents such as benzene, toluene and xylene; and water. Among these, DMF, dioxane or water is preferably used. The reaction temperature is thought to be 0° C. to 200° C., and is preferably 40° C. to 160° C., more preferably 60° C. to 140° C. The reaction time may appropriately be selected depending on the conditions such as reaction temperature, 1.5 and satisfactory results are usually obtained by selecting a reaction time between about 30 minutes and 30 hours.

Method B: In cases where V is —CH≡CH—

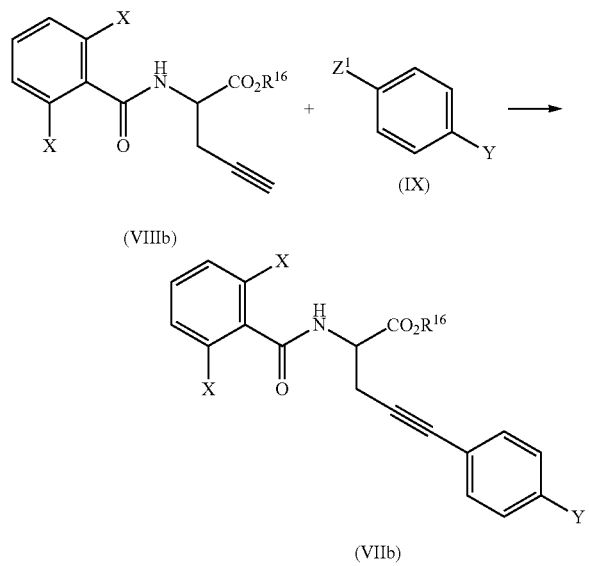

[wherein the symbols have the same meanings as described above]

The compounds of Formula (VIIb) can be synthesized by the coupling reaction between a compound of Formula (VIIIb) and a compound of Formula (IX). The coupling reaction is carried out in the presence of a palladium catalyst, a base, and a copper catalyst, in the presence or absence of a phosphine ligand, in an appropriate solvent.

The compound of Formula (IX) is used in an amount of 1.0 to 10 equivalents, preferably 1.0 to 4.0 equivalents with respect to the compound of Formula (VIIIb).

Examples of the palladium catalyst include palladium acetate, tetrakis(triphenylphosphine)palladium, bis(triphenylphosphine)palladium dichloride, palladium(II) chloride, bis(dibenzylideneacetone)palladium, and bis(diphenylphosphino) ferrocene palladium dichloride. Among these, tetrakis(triphenylphosphine)palladium or bis(triphenylphosphine)palladium dichloride is preferably used. The amount of the palladium catalyst used is 0.001 to 1 equivalent, preferably 0.005 to 0.2 equivalents with respect to the compound of Formula (VIIIb).

Examples of the base include potassium carbonate, potassium phosphate, cesium carbonate, sodium hydroxide, potassium hydroxide, sodium-tert-butoxide, diethylamine, triethylamine, diisopropylamine, diisopropylethylamine and n-butylamine. Among these, diethylamine, triethylamine, diisopropylamine or diisopropylethylamine is preferably used. The amount of the base used is 1 equivalent with respect to the compound of Formula (VIIIb) to an excess amount used as a solvent, preferably 4 equivalents with respect to the compound of Formula (VIIIb) to an excess amount.

Examples of the copper catalyst include copper powder, copper iodide and copper bromide, and copper iodide is preferably used. The copper catalyst is used in an amount of 0.001 to 0.5 equivalents, preferably 0.01 to 0.4 equivalents with respect to the compound of Formula (VIIIb).

Examples of the phosphine ligand include triphenylphosphine, tris(2-methylphenyl)phosphine, tetrakis(triphenyl)phosphine, tributylphosphine, triethylphosphine, tri-tert-butylphosphine, 2,2'-bis(diphenylphosphino)-1,1'-biphenyl, 2-(di-tert-butylphosphino)-1,1'-binaphthyl, 2-(dicyclohexylphosphino)diphenyl and 9,9-dimethyl-4,5-bis(diphenylphosphino)xanthene. Preferably, no phosphine ligand is used, or tris(2-methylphenyl)phosphine or tetrakis(triphenyl) phosphine is preferably used. When the phosphine ligand is used, the amount thereof is 0.001 to 0.5 equivalents, preferably 0.005 to 0.4 equivalents with respect to the compound of Formula (VIIIb).

Examples of the solvent include aprotic bipolar solvents such as DMF, DMSO and NMP; ether solvents such as THF, DME and dioxane; alcoholic solvents such as methanol and ethanol; halogen-containing solvents such as dichloromethane, chloroform, carbon tetrachloride and 1,2-dichloroethane; aromatic solvents such as benzene, toluene and xylene; organic amine solvents such as diethylamine, triethylamine and diisopropylamine; and water; as well as mixtures thereof. Preferably, THF, diethylamine, diisopropylamine, triethylamine or a mixture thereof is used. The reaction temperature is thought to be −40° C. to 200° C., and is preferably −20° C. to 100° C., more preferably −10° C. to 60° C. The reaction time may appropriately be selected depending on the conditions such as reaction temperature, and satisfactory results are usually obtained by selecting a reaction time between about 1 minute and 30 hours.

The compounds of Formula (VIIIa) and the compounds of Formula (VIIIb) can be synthesized by the following method:

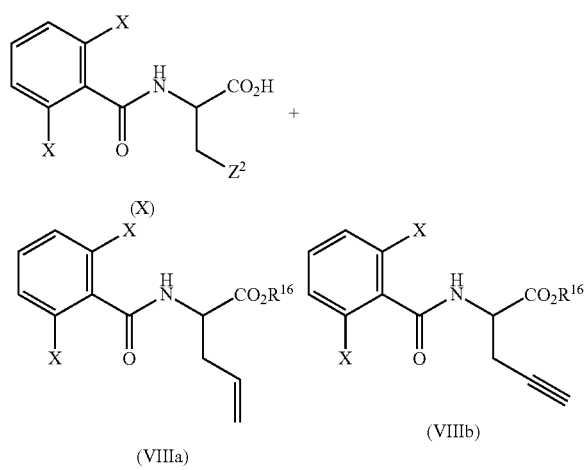

(X)

(VIIIa)

(VIIIb)

[wherein $Z^2$ represents —CH=CH$_2$ or —C≡CH, and the other symbols have the same meanings as described above]

The compounds of Formula (VIIIa) and the compounds of Formula (VIIIb) can be synthesized by the following methods (Method C, Method D or Method E):

Method C:

The compounds can be synthesized by condensing a compound of Formula (X) with $R^{16}$—OH (wherein $R^{16}$ represents the same meaning as described above). The condensation reaction may be carried out in the presence of a condensing agent, in the presence or absence of a base, in an appropriate solvent. Examples of the condensing agent include dicyclohexylcarbodiimide, BOP reagent and EDC. Preferably, EDC or BOP reagent is used. In cases where the base exists, examples of the base include triethylamine, diisopropylethylamine, pyridine, 4-dimethylaminopyridine and N-methylmorpholine. Preferably, triethylamine, 4-dimethylaminopyridine or diisopropylethylamine is used. The amount of $R^{16}$—OH used is 1.0 to 100 equivalents, preferably 1.0 to 4.0 equivalents with respect to the compound of Formula (X). The condensing agent is used in an amount of 1.0 to 20 equivalents, preferably 1.0 to 5.0 equivalents with respect to the compound of Formula (X). The base is used in an amount of 1.0 to 100 equivalents, preferably 1.0 to 40 equivalents with respect to the compound of Formula (X).

Examples of the solvent include aprotic bipolar solvents such as DMF, DMSO and NMP; ether solvents such as THF, DME and dioxane; and halogen-containing solvents such as dichloromethane, chloroform and 1,2-dichloroethane. Preferably, THF or dichloromethane is used. The reaction temperature is thought to be −40° C. to 100° C., and is preferably 0° C. to 60° C. The reaction time may appropriately be selected depending on the conditions such as reaction temperature, and satisfactory results are usually obtained by selecting a reaction time between about 1 minute and 30 hours.

Method D:

The compounds can be synthesized by condensing a reactive derivative of a compound of Formula (X) with $R^{16}$—OH (wherein $R^{16}$ represents the same meaning as described above) in the presence of a base. Examples of the reactive derivative of the compound of Formula (X) include acid halides (such as acid chloride). Examples of the base include organic amine bases such as triethylamine, pyridine and diisopropylethylamine; and inorganic bases such as sodium carbonate, potassium carbonate and sodium hydrogen carbonate. Preferably, triethylamine, pyridine or diisopropylethylamine is used. The amount of $R^{16}$—OH is 1.0 to 100 equivalents, preferably 1.0 to 20 equivalents with respect to the compound of Formula (X). The base is used in an amount of 1.0 to 100 equivalents, preferably 1.0 to 4.0 equivalents with respect to the compound of Formula (X).

Examples of the solvent include aprotic bipolar solvents such as DMF, DMSO and NMP; ether solvents such as THF, DME and dioxane; halogen-containing solvents such as dichloromethane, chloroform and 1,2-dichloroethane; and aromatic solvents such as benzene and toluene. Preferably, dichloromethane or THF is used. The reaction temperature is thought to be −10° C. to 100° C., and is preferably 0° C. to 40° C. The reaction time may appropriately be selected depending on the conditions such as reaction temperature, and satisfactory results are usually obtained by selecting a reaction time between about 1 minute and 30 hours.

Method E:

In cases where $R^{16}$ is methyl or ethyl, the compounds can be synthesized by adding a compound of Formula (X) to a mixture of methanol or ethanol and thionyl chloride. The amount of methanol or ethanol used is usually 1.0 equivalent with respect to the compound of Formula (X) to an excess amount used as a solvent, and is preferably 10 equivalents with respect to the compound of Formula (X) to an excess amount used as a solvent. The amount of thionyl chloride used is usually 1 equivalent with respect to the compound of Formula (X) to an excess amount used as a solvent. The reaction temperature is thought to be −50° C. to 60° C., and is preferably −20° C. to 40° C. The reaction time may appropriately be selected depending on the conditions such as reaction temperature, and satisfactory results are usually obtained by selecting a reaction time between about 1 minute and 60 hours.

The compounds of Formula (X) can be synthesized by the following method:

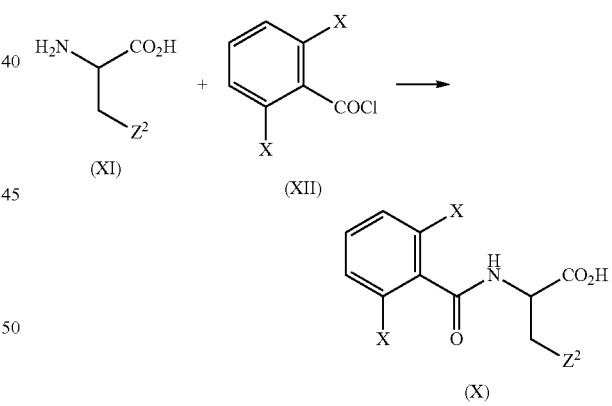

[wherein the symbols have the same meanings as described above]

The compounds can be synthesized by condensing a compound of Formula (XI) with a compound of Formula (XII) in the presence of a base in an appropriate solvent. The compounds of Formulae (XI) and (XII) are normally available materials. The compound of Formula (XII) is used in an amount of 1.0 to 20 equivalents, preferably 1.0 to 4.0 equivalents with respect to the compound of Formula (XI).

Examples of the base include organic amine bases such as triethylamine, pyridine and diisopropylethylamine; and inorganic bases such as sodium hydroxide, potassium hydroxide, sodium carbonate, potassium carbonate and sodium hydrogen carbonate. Preferably, triethylamine, pyridine, diisopropylethylamine, sodium hydroxide or potassium hydroxide is used. The base is used in an amount of 1.0 to 100 equivalents, preferably 1.0 to 50 equivalents with respect to the compound of Formula (XI).

Examples of the solvent include aprotic bipolar solvents such as DMF, DMSO and NMP; ether solvents such as THF, DME and dioxane; halogen-containing solvents such as dichloromethane, chloroform and 1,2-dichloroethane; and water, as well as mixtures thereof. Preferably, dichloromethane, THF, dioxane, water or a mixture thereof is used. The reaction temperature is thought to be −10° C. to 100° C., and is preferably 0° C. to 40° C. The reaction time may appropriately be selected depending on the conditions such as reaction temperature, and satisfactory results are usually obtained by selecting a reaction time between about 1 minute and 60 hours.

The compounds of Formula (IX) can be synthesized by the following method (Method F to Method H) depending on the structure of "Y" (Y has the same meaning as described above) in Formula (IX):

Method F:

In cases where Y is represented by the following Formula (IIa):

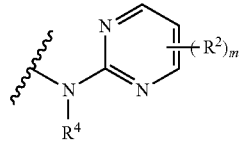

(IIa)

[wherein the symbols have the same meanings as described above]

the compounds of Formula (IX) can be synthesized by the following method:

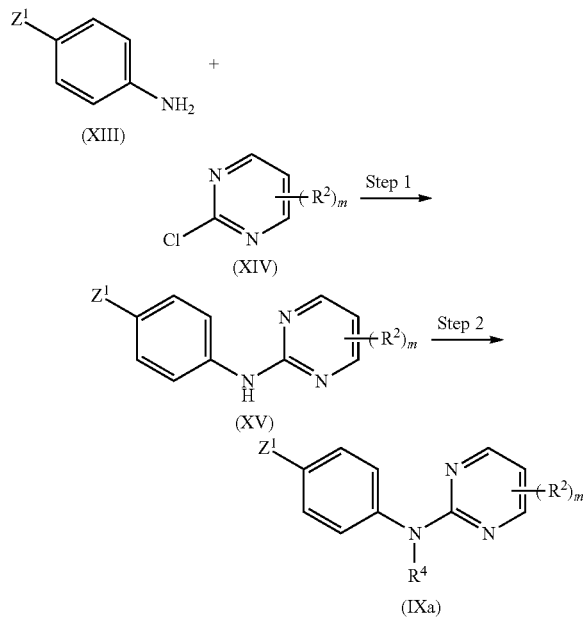

[wherein the symbols have the same meanings as described above]

Step 1:

The compounds of Formula (XV) may be synthesized by condensing a compound of Formula (XIII) and a compound of Formula (XIV) in the presence of an acid in an appropriate solvent. Examples of the acid include acetic acid, trifluoroacetic acid, methanesulfonic acid, p-toluenesulfonic acid and camphor sulfonic acid. Preferably, acetic acid is used. The compounds of Formula (XIII) are normally available materials and the compounds of Formula (XIV) are normally available materials or may be synthesized by a known method. The compound of Formula (XIV) is used in an amount of 1.0 to 10 equivalents, preferably 1.0 to 4.0 equivalents with respect to the compound of Formula (XIII). The acid is used in an amount of 1.0 equivalent to an excess amount used as a solvent, preferably in an amount of 1.0 to 20 equivalents.

Examples of the solvent include ether solvents such as THF, DME and dioxane; halogen-containing solvents such as dichloromethane and carbon tetrachloride; aromatic solvents such as benzene, toluene and xylene; and aprotic bipolar solvents such as DMF and DMSO. Preferably, DME or dioxane is used. The reaction temperature is thought to be 0° C. to 160° C., and is preferably 40° C. to 100° C. The reaction time may appropriately be selected depending on the conditions such as reaction temperature, and satisfactory results are usually obtained by selecting a reaction time between about 1 hour and 30 hours.

Step 2:

The compounds of Formula (IXa) can be synthesized by adding a base to a compound of Formula (XV) in an appropriate solvent and further adding $R^4$—$Z^1$ (wherein the symbols have the same meanings as described above) to conduct condensation. The compound of $R^4$—$Z^1$ is used in an amount of 1.0 to 10 equivalents, preferably 1.0 to 4.0 equivalents with respect to the compound of Formula (XV).

Examples of the base include metal hydrides such as sodium hydride and potassium hydride; inorganic bases such as potassium carbonate, sodium carbonate and cesium carbonate; organic metals such as butyllithium; and organic amines such as DBU, diisopropylethylamine and triethylamine. Preferably, sodium hydride is used. The base is used in an amount of 1.0 to 50 equivalents, preferably 1.0 to 20 equivalents with respect to the compound of Formula (XV). Examples of the solvent include ether solvents such as THF, DME and dioxane; halogen-containing solvents such as dichloromethane and carbon tetrachloride; aromatic solvents such as benzene, toluene and xylene; and aprotic bipolar solvents such as DMF and DMSO. Preferably, DMF or THF is used. The reaction temperature is thought to be −78° C. to 160° C., and is preferably −20° C. to 40° C. The reaction time may appropriately be selected depending on the conditions such as reaction temperature, and satisfactory results are usually obtained by selecting a reaction time between about 15 minutes and 30 hours.

Method G:

In cases where Y is represented by the following Formula (IIb):

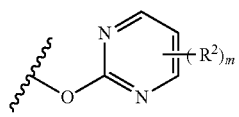

(IIb)

[wherein the symbols have the same meanings as described above]

the compounds of Formula (IX) can be synthesized by the following method:

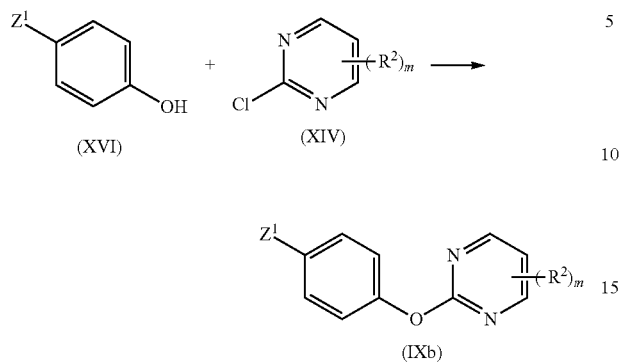

[wherein the symbols have the same meanings as described above]

The compounds can be synthesized by condensing a compound of Formula (XVI) and a compound of Formula (XIV) in the presence of a base in an appropriate solvent. The compounds of Formula (XVI) are normally available materials. The amount of the compound of Formula (XIV) used is 1.0 to 10 equivalents, preferably 1.0 to 4.0 equivalents with respect to the compound of Formula (XVI).

Examples of the base include metal hydrides such as sodium hydride and potassium hydride; inorganic bases such as potassium carbonate, sodium carbonate and cesium carbonate; organic metals such as butyllithium; and organic amines such as DBU, diisopropylethylamine and triethylamine. Preferably, potassium carbonate or sodium carbonate is used. The amount of the base used is 1.0 to 50 equivalents, preferably 1.0 to 20 equivalents with respect to the compound of Formula (XVI).

Examples of the solvent include ether solvents such as THF, DME and dioxane; halogen-containing solvents such as dichloromethane and carbon tetrachloride; aromatic solvents such as benzene, toluene and xylene; and aprotic bipolar solvents such as DMF and DMSO. Preferably, DMF is used. The reaction temperature is thought to be 0° C. to 200° C., and is preferably 20° C. to 140° C. The reaction time may appropriately be selected depending on the conditions such as reaction temperature, and satisfactory results are usually obtained by selecting a reaction time between about 30 minutes and 30 hours.

Method H:

In cases where Y is represented by the following Formula (IIIa):

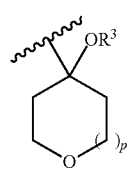

[wherein the symbols have the same meanings as described above]

the compounds of Formula (IX) can be synthesized by the following method:

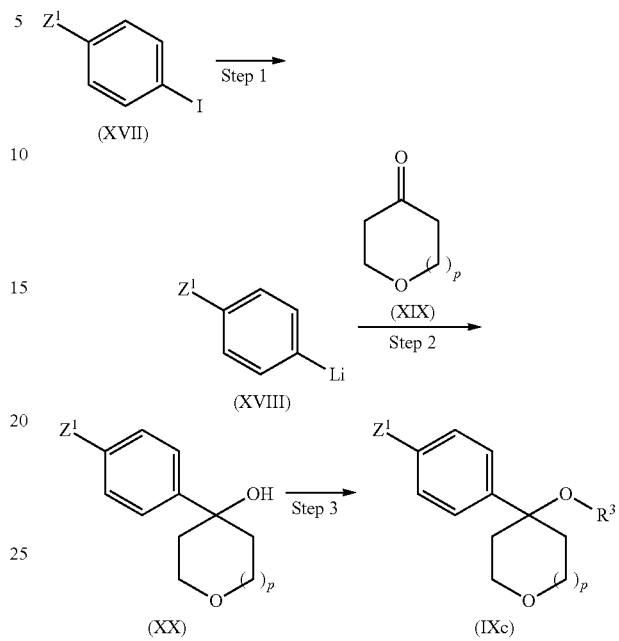

[wherein the symbols have the same meanings as described above]

Steps 1 and 2:

By lithiation of a compound of Formula (XVII) in an appropriate solvent, a compound of Formula (XVIII) is obtained. By subsequently reacting this compound without isolation with a compound of Formula (XIX), a compound of Formula (XX) is obtained. The compounds of Formula (XVII) are normally available materials. Examples of the lithiating agent include lithium, n-butyllithium, sec-butyllithium and tert-butyllithium. Preferably, n-butyllithium is used. The amount of the lithiating agent used is 1.0 to 4.0 equivalents, preferably 1.0 to 2.2 equivalents with respect to the compound of Formula (XVII). The compounds of Formula (XIX) are normally available materials. The amount of the compound of Formula (XIX) used is 1.0 to 10 equivalents, preferably 1.0 to 4.0 equivalents with respect to the compound of Formula (XVII).

Examples of the solvent include ether solvents such as ether, dioxane and THF, and preferably, THF is used. The reaction temperature in Step 1 is thought to be −100° C. to 0° C., and is preferably −78° C. to 0° C. The reaction temperature in Step 2 is thought to be −100° C. to 40° C., and is preferably −78° C. to 40° C. The reaction time may appropriately be selected depending on the conditions such as reaction temperature, and in Step 1, about 5 minutes to 2 hours is usually appropriate, and in Step 2, satisfactory results are usually obtained by selecting a reaction time between about 5 minutes and 24 hours.

Step 3

The compounds of Formula (IXc) can be synthesized by adding a base to a compound of Formula (XX) in an appropriate solvent, and subsequently adding $R^3$—$Z^1$ (wherein the symbols have the same meanings as described above) to conduct condensation. The compounds represented by $R^3$—$Z^1$ are normally available materials. The amount of $R^3$—$Z^1$ used is 1.0 to 20 equivalents, preferably 1.0 to 4.0 equivalents with respect to the compound of Formula (XX).

Examples of the base include metal hydrides such as sodium hydride and potassium hydride; inorganic bases such as potassium carbonate, sodium carbonate and cesium carbonate; organic metals such as butyllithium; and organic amines such as DBU, diisopropylethylamine and triethylamine. Preferably, sodium hydride is used. The amount of the base used is 1.0 to 50 equivalents, preferably 1.0 to 20 equivalents with respect to the compound of Formula (XX).

Examples of the solvent include ether solvents such as THF, DME and dioxane; halogen-containing solvents such as dichloromethane and carbon tetrachloride; aromatic solvents such as benzene, toluene and xylene; and aprotic bipolar solvents such as DMF and DMSO. Preferably, DMF or THF is used. The reaction temperature is thought to be $-78°$ C. to $100°$ C., and is preferably $-20°$ C. to $40°$ C. The reaction time may appropriately be selected depending on the conditions such as reaction temperature, and satisfactory results are usually obtained by selecting a reaction time between about 15 minutes and 30 hours.

The workup and purification of each step in the synthesis of the compounds represented by Formula (I) or pharmaceutically acceptable salts thereof can be carried out by an ordinary method. That is, as the workup, separation extraction, filtration or the like may be employed. As the purification, column chromatography, thin layer chromatography, recrystallization, reprecipitation, distillation or the like may be employed.

The therapeutic or prophylactic agents for allergic dermatitis according to the present invention have a glycine structure substituted with an allyl group or propargyl group, a substructure represented by Formula (II) or (III), and the 2,6-di-substituted benzoyl structure shown in Formula (I). These compounds have more excellent oral absorbability and in vivo stability than those disclosed in WO099/26923 mentioned in Background Art, and therefore exhibit therapeutic or prophylactic effects on allergic dermatitis.

The oral absorbability and in vivo stability of the therapeutic or prophylactic agents of the present invention may be confirmed by using as an index bioavailability (BA) and clearance of the compound administered to an animal, but the method for confirmation is not restricted thereto.

The excellent effect of the therapeutic or prophylactic agents of the present invention on allergic dermatitis may be evaluated based on the activity to inhibit the swelling response caused by an antigen by using the method described in the literature [Inflamm. Res., 47, 506-511 (1998)]. It is known that the dermatitis reaction observed in this model is similar to the swelling response observed when an antigen is applied to a human patient suffering from allergic dermatitis. This method is also used as an animal model of atopic dermatitis. However, the evaluation method is not restricted thereto.

The therapeutic or prophylactic agents according to the present invention inhibit allergic dermatitis induced by an antigen in an animal model, and therefore can be used for ameliorating allergic dermatitis induced by an antigen, more specifically, diffuse neurodermatitis, atopic eczema, atopic neurodermatitis, Besnier's prurigo, acute infantile eczema, flexural eczema, infantile eczema on the limbs, infantile atopic eczema, infantile xerotic eczema, infantile eczema, adult atopic dermatitis, endogenic eczema, infantile dermatitis, chronic infantile eczema and the like. Examples of the antigen mentioned herein include mite allergens (*Dermatophagoides farinae, Dermatophagoides pteronyssinus* and the like), food allergens (albumen, milk, wheat, soy bean, rice, corn, sesame, buckwheat and the like), pollen allergens (ragweed, *Artemisia*, Solidago (goldenrod), vernal grass, orchard grass, Bermuda grass, timothy, reed and the like), fungus allergens (*Candida, Penicillium, Cladosporium, Aspergillus, Alternaria* and the like), animal epithelium allergens (cat, dog), and hapten antigens (DNFB, DNP, TNP and the like). Moreover, the therapeutic or prophylactic agents according to the present invention may be used for ameliorating the symptoms accompanied by allergic dermatitis, for example, erythema, papule, scale, incrustation, lichenification, xerosis (dry skin), pruritus, xeroderma, chilitis, keratosis follicular, darkening of eyelids, facial pallor, pityriasis alba, food intolerance, white dermographism, and delayed blanch response.

The effect of the therapeutic or prophylactic agents according to the present invention on allergic dermatitis can be explained by the inhibition of leukocyte functions (e.g., adhesion and growth of cells) and inhibition of production of inflammatory mediators (e.g., cytokines and chemical mediators) by leukocytes. As the leukocytes, neutrophils, monocytes, lymphocytes, which are originated from peripheral blood, or established cell lines thereof, are used. For the evaluations of the leukocyte functions and the inflammatory mediators, the methods described in, for example, Current Protocols in Immunology (John Wiley & Sons, Inc) are used, but the evaluation methods are not restricted thereto.

The therapeutic or prophylactic agents for allergic dermatitis according to the present invention can be used as a pharmaceutical for mammals (e.g., mouse, rat, hamster, rabbit, dog, monkey, bovine, ovine, human and the like).

When using the compound clinically, the drug may be the free compound or a salt thereof per se, or an additive(s) such as a vehicle, stabilizer, preservative, buffering agent, solubilizer, emulsifier, diluent and/or isotonic agent, may be admixed appropriately. The drug may be produced by a conventional method by appropriately using these pharmaceutical carriers. Examples of the administration mode include oral preparations such as tablets, capsules, granules, powders and syrups; parenteral preparations such as inhalants, injection solutions, suppositories and liquids; and topical preparations such as ointments, creams and patches. Further, known sustained-release preparations are also included.

The therapeutic or prophylactic agent for allergic dermatitis according to the present invention preferably contains the above-described effective ingredient in an amount of 0.001 to 90% by weight, more preferably 0.01 to 70% by weight. Although the dose may be selected depending on the symptoms, age, body weight, sex, administration method and the like, in case of an injection solution, a dose of 0.01 mg to 25 g, preferably 0.1 mg to 10 g, in case of an oral preparation, a dose of 0.1 mg to 50 g, preferably 1 mg to 20 g, and in case of a topical preparation, a dose of 0.0001 to 10%, preferably 0.001 to 5%, in terms of the effective ingredient, respectively, may be administered to an adult per day in one time or dividedly in several times.

Examples of the pharmaceutically acceptable carrier or diluent include binders (syrups, gelatin, gum Arabic, sorbitol, polyvinyl chloride, tragacanth and the like), vehicles (sucrose, lactose, corn starch, calcium phosphate, sorbitol, glycine and the like), lubricants (magnesium stearate, polyethylene glycol, talc, silica and the like).

The therapeutic or prophylactic agent for allergic dermatitis according to the present invention may be used alone, or may be blended with or used together with other drug(s) for therapy or prophylaxis of the disease, or for alleviation or suppression of symptoms, or for complementation or enhancement of the prophylactic or therapeutic effect, or for decreasing the dose.

Examples of the drugs which may be used together include steroids (prednisolone, methylprednisolone, hydrocortisone, betamethasone and the like), immunosuppressants (cyclosporin, tacrolimus and the like), vaseline, urea ointments, zinc oxide ointments, antihistamines (chlorpheniramine and the like), antiallergic drugs (sodium cromoglycate), Th2 cytokine inhibitors (suplatast and the like), NFκB decoy DNAs, adhesion molecule inhibitors, active oxygen scavengers, active oxygen production inhibitors, antibiotics (metronidazole and the like), antibacterial agents and the like.

EXAMPLES

The present invention will now be described more practically by way of examples thereof. Abbreviations used herein mean the following compounds.

Abbreviations:
THF: tetrahydrofuran
DMF: dimethylformamide
Boc: tert-butoxycarbonyl
DMF: dimethylformamide
NMP: N-methylpyrrolidone
DME: dimethoxyethane
DMSO: dimethylsulfoxide
BOP: benzotriazol-1-yloxytris(dimethylamino)-phosphonium hexafluoro phosphate
EDC: 1-ethyl-3-(3-dimethylaminopropyl)carbodiimide hydrochloride
DBU: 1,8-diazabicyclo[5.4.0]undeca-7-ene
HOBT: 1-hydroxybenzotriazole

Reference Example 1

Tetrahydro-4-(4-iodophenyl)-2H-pyran-4-ol

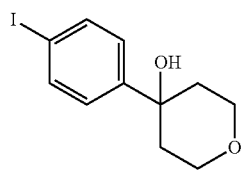 [SMILES: OC1(c2ccc(I)cc2)CCOCC1]

Under an argon atmosphere, a solution of n-butyllithium (2.59M, in hexane) (8.76 ml) was added dropwise to a solution of 1,4-diiodobenzene (7.49 g) in anhydrous THF (50 ml) at −78° C., and the resulting mixture was stirred at −78° C. for minutes. Tetrahydro-4H-pyran-4-one (2.09 ml) was added dropwise thereto and the resulting mixture was stirred at −78° C. for 1.5 hours. After stirring the mixture for another 3 hours at room temperature, water was added, and the resulting mixture was extracted with ethyl acetate. Organic layer was washed once with water and once with saturated brine, and dried over anhydrous sodium sulfate. After removing anhydrous sodium sulfate by filtration, the filtrate was concentrated. The residue was recrystallized from cyclohexane/ethyl acetate mixed solvent to obtain tetrahydro-4-(4-iodophenyl)-2H-pyran-4-ol (4.12 g).

Reference Example 2

Tetrahydro-4-(4-iodophenyl)-4-methoxy-2H-pyran

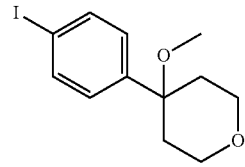

Under an argon atmosphere, a solution of tetrahydro-4-(4-iodophenyl)-2H-pyran-4-ol (2.99 g) in anhydrous DMF (10 ml) was added dropwise to a suspension of sodium hydride (60 wt %) (432 mg) in anhydrous DMF (20 ml) at room temperature, and the resulting mixture was stirred at room temperature for 75 minutes. Methyl iodide (0.92 ml) was added dropwise to the reaction solution and the resulting mixture was stirred at room temperature for 8.5 hours. Water was added thereto and the resulting mixture was extracted twice with ethyl acetate. Organic layers were washed with saturated brine, and dried over anhydrous sodium sulfate. After removing anhydrous sodium sulfate by filtration, the filtrate was concentrated. The residue was purified by column chromatography (silica gel, eluent: cyclohexane/ethyl acetate=10/1) to obtain tetrahydro-4-(4-iodophenyl)-4-methoxy-2H-pyran (2.87 g). NMR (H$^1$, CDCl$_3$): δ 1.90-2.02 (4H, m), 2.97 (3H, s), 3.80-3.88 (4H, m), 7.14 (1H, d, J=8.5 Hz), 7.70 (1H, d, J=8.5 Hz)

Reference Example 3

4-Ethoxy-tetrahydro-4-(4-iodophenyl)-2H-pyran

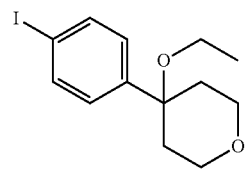 [SMILES: CCOC1(c2ccc(I)cc2)CCOCC1]

In the same manner as in Reference Example 2, tetrahydro-4-(4-iodophenyl)-2H-pyran-4-ol (302 mg) and iodoethane (0.119 ml) were reacted to obtain 4-ethoxy-tetrahydro-4-(4-iodophenyl)-2H-pyran (269 mg).

Reference Example 4

4-(4-Bromophenyl)-tetrahydro-4-(methoxymethyl)-2H-pyran

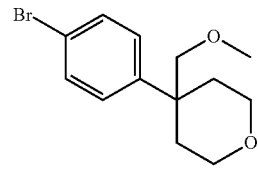

(1) Under an argon atmosphere, sodium hydride (60 wt %) (240 mg) was added to a solution of 2-(4-bromophenyl)acetic acid methyl ester (916 mg) in anhydrous DMF (20 ml) at 0° C., and the resulting mixture was stirred at 0° C. for 30 minutes. To the reaction solution, bis(2-bromoethyl)ether (0.70 mL) was added, and the resulting mixture was stirred at 0° C. for 1 hour. Sodium hydride (60 wt %) (240 mg) was added thereto and the resulting mixture was further stirred at 0° C. for 1 hour. Saturated aqueous ammonium chloride solution was added thereto, and the resulting mixture was extracted with ethyl acetate. Organic layer was washed once with saturated brine, and dried over anhydrous sodium sulfate. After removing anhydrous sodium sulfate by filtration, the filtrate was concentrated. The residue was purified by column chromatography (silica gel, eluent: hexane/ethyl acetate=4/1) to obtain 4-(4-bromophenyl)-tetrahydro-2H-pyran-4-carboxylic acid methyl ester (472 mg).

(2) Under an argon atmosphere, a solution of 4-(4-bromophenyl)-tetrahydro-2H-pyran-4-carboxylic acid methyl ester (472 mg) obtained in (1) in anhydrous THF (8.7 mL) was added to a 1.0 M solution of diisobutylaluminum hydride in hexane (8.7 mL) at 0° C., and the resulting mixture was stirred at 0° C. for 30 minutes. After adding methanol (2.1 ml) to the reaction solution, 1N hydrochloric acid (8.7 mL) was added thereto and the resulting mixture was extracted 4 times with diethyl ether. Organic layers were washed with saturated brine, and dried over anhydrous sodium sulfate. After removing anhydrous sodium sulfate by filtration, the filtrate was concentrated to obtain (4-(4-bromophenyl)-tetrahydro-2H-pyran-4-yl)methanol (405 mg).

(3) Under an argon atmosphere, sodium hydride (60 wt %) (88 mg) was added to a solution of (4-(4-bromophenyl)-tetrahydro-2H-pyran-4-yl)methanol (397 mg) obtained in (2) in anhydrous DMF (1.5 mL) at 0° C., and the resulting mixture was stirred at 0° C. for 30 minutes. Methyl iodide (0.13 ml) was added dropwise to the reaction solution, and the resulting mixture was stirred at room temperature for 2 hours. Saturated brine was added thereto and the resulting mixture was extracted 3 times with ethyl acetate. Organic layers were washed with saturated brine and dried over anhydrous sodium sulfate. After removing anhydrous sodium sulfate by filtration, the filtrate was concentrated. The residue was purified by column chromatography (silica gel, eluent: hexane/ethyl acetate=5/1) to obtain 4-(4-bromophenyl)-tetrahydro-4-(methoxymethyl)-2H-pyran (399 mg).

Reference Example 5

4-(4-Iodophenyl)-4-methoxyoxepane

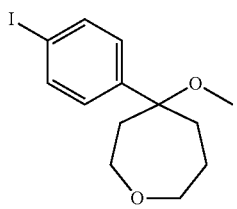 [SMILES: COC1(c2ccc(I)cc2)CCCOCC1]

(1) Under an argon atmosphere, a solution of n-butyllithium (1.50 M, in hexane) (0.5 ml) was added dropwise to a solution of 1,4-diiodobenzene (250 mg) in anhydrous THF (3 ml) at −78° C., and the resulting mixture was stirred at −78° C. for 30 minutes. Oxepan-4-one (151 mg) was added to the reaction solution, and the resulting mixture was stirred at −78° C. for 1 hour. Saturated aqueous ammonium chloride solution was added thereto, and the resulting mixture was extracted with ethyl acetate. Organic layer was washed with saturated brine, and dried over anhydrous sodium sulfate. After removing anhydrous sodium sulfate by filtration, the filtrate was concentrated. The residue was purified by column chromatography (silica gel, eluent: hexane/ethyl acetate=5/1) to obtain 4-(4-iodophenyl)oxepan-4-ol (89 mg).

(2) Under an argon atmosphere, a solution of 4-(4-iodophenyl)oxepan-4-ol (86 mg) obtained in (1) in anhydrous DMF (1.0 mL) was added to a suspension of sodium hydride (60 wt %) (16 mg) in anhydrous DMF (1.0 ml) at 0° C., and the resulting mixture was stirred at 0° C. for 30 minutes. Methyl iodide (0.025 ml) was added dropwise to the reaction solution, and the resulting mixture was stirred at room temperature for 10 hours. Saturated brine was added thereto, and the resulting mixture was extracted 3 times with ethyl acetate. Organic layers were washed with saturated brine and dried over anhydrous sodium sulfate. After removing anhydrous sodium sulfate by filtration, the filtrate was concentrated. The residue was purified by column chromatography (silica gel, eluent: hexane/ethyl acetate=6/1) to obtain 4-(4-iodophenyl)-4-methoxyoxepane (63 mg).

Reference Example 6

2-(4-Iodophenoxy)pyrimidine

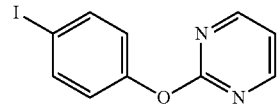 [SMILES: Ic1ccc(Oc2ncccn2)cc1]

Under an argon atmosphere, potassium carbonate (207 mg) was added to a solution of 4-iodophenol (220 mg) and 2-chloropyrimidine (114 mg) in DMF (1 ml), and the resulting mixture was stirred at 120° C. for 3 hours. The reaction solution was cooled to room temperature and saturated brine was added thereto, followed by extracting the resulting mixture with chloroform. Organic layer was washed with saturated brine and dried over anhydrous sodium sulfate. After removing anhydrous sodium sulfate by filtration, the filtrate was concentrated. The residue was purified by column chromatography (silica gel, eluent: hexane/ethyl acetate=3/1) to obtain 2-(4-iodophenoxy)pyrimidine (288 mg). NMR (1', CDCl$_3$): δ 6.97-7.00 (2H, m), 7.06 (1H, t, J=4.6 Hz), 7.73-7.75 (2H, m), 8.57 (2H, d, J=4.6 Hz)

Reference Example 7

2-(4-Iodophenoxy)-5-ethylpyrimidine

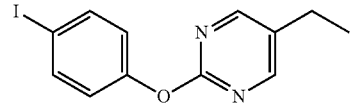

In the same manner as in Reference Example 6, 4-iodophenol (220 mg) and 5-ethyl-2-chloropyrimidine (0.121 ml)

were reacted in the presence of potassium carbonate (415 mg) to obtain 2-(4-iodophenoxy)-5-ethylpyrimidine (256 mg).

Reference Example 8

2-(4-Iodophenoxy)-4-methoxypyrimidine

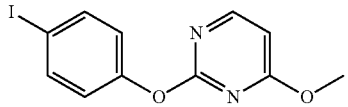 [SMILES: COc1ccnc(Oc2ccc(I)cc2)n1]

Under an argon atmosphere, sodium hydride (108 mg) was added to a solution of 4-iodophenol (220 mg) and 2-chloro-4-methoxypyrimidine (168 mg) in anhydrous DMF (10 ml), and the resulting mixture was stirred at 125° C. for 9 hours. The reaction solution was cooled to room temperature and water was added thereto, followed by extracting the resulting mixture with ethyl acetate. Organic layer was washed with saturated brine and dried over anhydrous sodium sulfate. After removing anhydrous sodium sulfate by filtration, the filtrate was concentrated. The residue was purified by column chromatography (silica gel, eluent: hexane/ethyl acetate=5/1) to obtain 2-(4-iodophenoxy)-4-methoxypyrimidine (312 mg).

Reference Example 9

2-(4-Iodophenoxy)-4,6-dimethoxypyrimidine

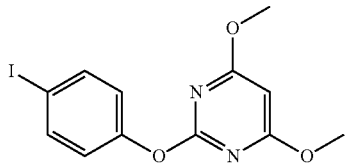 [SMILES: COc1cc(OC)nc(Oc2ccc(I)cc2)n1]

In the same manner as in Reference Example 8, 4-iodophenol (223 mg) and 2-chloro-4,6-dimethoxypyrimidine (192 mg) were reacted by using sodium hydride to obtain 2-(4-iodophenoxy)-4,6-dimethoxypyrimidine (322 mg).

Reference Example 10

2-(4-Iodophenoxy)-4,6-dimethylpyrimidine

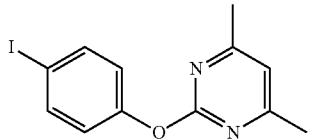 [SMILES: Cc1cc(C)nc(Oc2ccc(I)cc2)n1]

(1) Under an argon atmosphere, phosphorus oxychloride (2 ml) was added to 4,6-dimethyl-2-hydroxypyrimidine (400 mg), and the resulting mixture was stirred for 1 hour while heating the mixture to reflux. The reaction solution was cooled to room temperature, and the cooled solution was added in small portions to water. After adding sodium hydrogen carbonate in small portions to the resulting mixture to neutralize it, the mixture was extracted with ethyl acetate. Organic layer was washed twice with water and once with saturated brine, and dried over anhydrous sodium sulfate. After removing anhydrous sodium sulfate by filtration, the filtrate was concentrated to obtain 2-chloro-4,6-dimethylpyrimidine (350 mg).

(2) In the same manner as in Reference Example 8, 4-iodophenol (223 mg) and 2-chloro-4,6-dimethylpyrimidine (157 mg) were reacted by using sodium hydride to obtain 2-(4-iodophenoxy)-4,6-dimethylpyrimidine (226 mg), Reference Example 11

N-(4-Iodophenyl)pyrimidin-2-amine

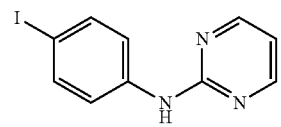 [SMILES: Ic1ccc(Nc2ncccn2)cc1]

Under an argon atmosphere, 2-chloropyrimidine (16.5 g) and acetic acid (11.7 ml) were added to a solution of 4-iodoaniline (30 g) in dioxane (500 ml), and the resulting mixture was stirred for 13 hours while heating the mixture to reflux. The reaction solution was cooled to room temperature and saturated aqueous sodium hydrogen carbonate solution was added thereto, followed by extracting the resulting mixture 4 times with ethyl acetate. Organic layers were washed 3 times with saturated brine and dried over anhydrous sodium sulfate. After removing anhydrous sodium sulfate by filtration, the filtrate was concentrated. The residue was purified by column chromatography (silica gel, eluent: cyclohexane/ethyl acetate=4/1). The product was recrystallized from dichloromethane/hexane mixed solvent to obtain N-(4-iodophenyl)pyrimidin-2-amine (22.27 g). NMR (H$^1$, CDCl$_3$): δ 6.73 (1H, t, J=4.6 Hz), 7.18 (1H, brs), 7.40-7.42 (2H, m), 7.59-7.61 (2H, m), 8.41 (2H, d, J=4.6 Hz)

Reference Example 12

N-(4-Bromophenyl)pyrimidin-2-amine

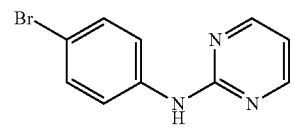

Under an argon atmosphere, 2-chloropyrimidine (2.68 g) and acetic acid (1.97 ml) were added to a solution of 4-bromoaniline (4.03 g) in dioxane (200 ml), and the resulting mixture was stirred for 3 hours while heating the mixture to reflux. Saturated aqueous sodium hydrogen carbonate solution was added in small portions to the reaction solution to neutralize it, and the resulting mixture was concentrated. Ethyl acetate (500 ml) was added to the residue and the resulting mixture was stirred at room temperature for 10 minutes, followed by removing insoluble matter by filtration. The filtrate was washed with saturated aqueous sodium hydrogen carbonate solution and with saturated brine, and dried over anhydrous sodium sulfate. After removing anhydrous sodium sulfate by filtration, the filtrate was concentrated. The residue was recrystallized from ethyl acetate to obtain N-(4-bromophenyl)pyrimidin-2-amine (3.02 g).

Reference Example 13

N-(4-Iodophenyl)-N-methylpyrimidin-2-amine

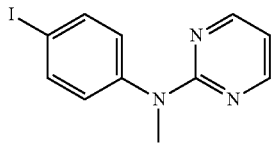

Under an argon atmosphere, a solution of N-(4-iodophenyl)pyrimidin-2-amine (1.47 g) in anhydrous DMF (10 ml) was added dropwise to a suspension of sodium hydride (218 mg) in anhydrous DMF (8 ml), and the resulting mixture was stirred at room temperature for 75 minutes. Methyl iodide (0.37 ml) was added dropwise to the reaction solution and the resulting mixture was stirred at room temperature for another 1 hour. Water was added thereto and the resulting mixture was extracted with ethyl acetate. Organic layer was washed twice with water and once with saturated brine, and dried over anhydrous sodium sulfate. After removing anhydrous sodium sulfate by filtration, the filtrate was concentrated. The residue was recrystallized from hexane to obtain N-(4-iodophenyl)-N-methylpyrimidin-2-amine (1.38 g). NMR ($H^1$, $CDCl_3$): δ 3.49 (3H, s), 6.58 (1H, t, J=4.6 Hz), 7.07-7.09 (2H, m), 7.67-7.69 (2H, m), 8.32 (2H, d, J=4.6 Hz)

Reference Example 14

N-(4-Iodophenyl)-N-ethylpyrimidin-2-amine

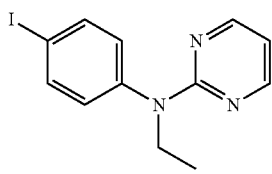 [SMILES: CCN(c1ccc(I)cc1)c1ncccn1]

Under an argon atmosphere, a solution of N-(4-iodophenyl)pyrimidin-2-amine (255 mg) in anhydrous DMF (1 ml) was added dropwise to a suspension of sodium hydride (40 mg) in anhydrous DMF (1 ml), and the resulting mixture was stirred at room temperature for 75 minutes. Ethyl iodide (0.10 ml) was added dropwise to the reaction solution and the resulting mixture was stirred at room temperature overnight. Saturated brine was added thereto and the resulting mixture was extracted with chloroform. Organic layer was washed with saturated brine and dried over anhydrous sodium sulfate. After removing anhydrous sodium sulfate by filtration, the filtrate was concentrated. The residue was purified by column chromatography (silica gel, eluent: cyclohexane/chloroform=1/10) to obtain N-(4-iodophenyl)-N-ethylpyrimidin-2-amine (264 mg). NMR ($H^1$, $CDCl_3$): δ 1.23 (3H, t, J=6.8 Hz), 4.01 (2H, q, J=6.8 Hz), 6.57 (1H, t, J=4.9 Hz), 7.03-7.06 (2H, m), 7.70-7.74 (2H, m), 8.32 (2H, d, J=4.9 Hz)

Reference Example 15

N-(4-Iodophenyl)-N-(2-methoxyethyl)pyrimidin-2-amine

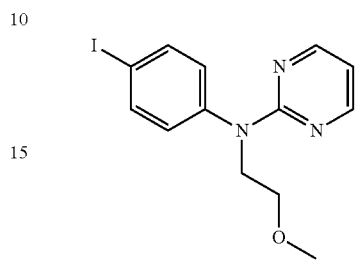

Under an argon atmosphere, 2-bromoethylmethyl ether (0.14 ml) and sodium hydride (48 mg) were added to a solution of N-(4-iodophenyl)pyrimidin-2-amine (300 mg) in anhydrous DMF (1 ml), and the resulting mixture was stirred at room temperature overnight. Saturated brine was added to the reaction solution and the resulting mixture was extracted with chloroform, followed by drying the organic layer over anhydrous sodium sulfate. After removing anhydrous sodium sulfate by filtration, the filtrate was concentrated. The residue was purified by column chromatography (silica gel, eluent: hexane/chloroform=1/10) to obtain N-(4-iodophenyl)-N-(2-methoxyethyl)pyrimidin-2-amine (233 mg). NMR ($H^1$, $CDCl_3$): δ 3.32 (3H, s), 3.63 (2H, t, J=5.9 Hz), 4.14 (2H, t, J=5.9 Hz), 6.59 (1H, t, J=4.9 Hz), 7.09-7.13 (2H, m), 7.70-7.73 (2H, m), 8.32 (2H, d, J=4.9 Hz)

Reference Example 16

N-(4-Iodophenyl)-N-isopropylpyrimidin-2-amine

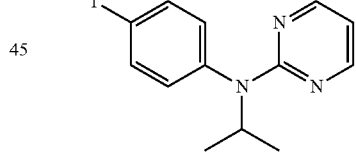

Under an argon atmosphere, a solution of N-(4-iodophenyl)pyrimidin-2-amine (8.00 g) in anhydrous DMF (50 ml) was added dropwise to a suspension of sodium hydride (1.08 g) in anhydrous DMF (200 ml), and the resulting mixture was stirred at room temperature for 80 minutes. To the reaction solution, 2-iodopropane (4.03 ml) was added, and the resulting mixture was stirred at room temperature for 2 hours. Sodium hydride (1.08 g) was added to the reaction solution and thereafter 2-iodopropane (4.03 ml) was added dropwise thereto, followed by stirring the resulting mixture at room temperature for 6 hours. Water was added to the reaction solution and the resulting mixture was extracted twice with ethyl acetate. Organic layers were washed 4 times with water and once with saturated brine, and dried over anhydrous sodium sulfate. After removing anhydrous sodium sulfate by filtration, the filtrate was concentrated. The residue was purified by column chromatography (silica gel, eluent:

cyclohexane→cyclohexane/ethyl acetate=50/1). The obtained solid was recrystallized from hexane to obtain N-(4-iodophenyl)-N-isopropylpyrimidin-2-amine (7.06 g). NMR (H$^1$, CDCl$_3$): δ 1.14 (3H, s), 1.16 (3H, s), 5.12-5.19 (1H, m), 6.52 (1H, t, J=4.6 Hz), 6.88-6.92 (2H, m), 7.74-7.77 (2H, m), 8.29 (2H, d, J=4.6 Hz)

Reference Example 17 (4-Acetoxybenzyl)-(4-iodophenyl)pyrimidin-2-ylamine

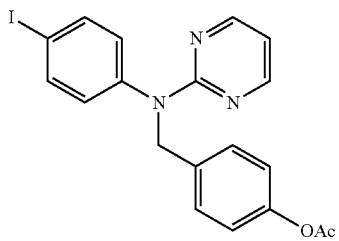 [SMILES: CC(=O)Oc1ccc(CN(c2ccc(I)cc2)c2ncccn2)cc1]

Under an argon atmosphere, a solution of N-(4-iodophenyl)pyrimidin-2-amine (68 mg) in anhydrous DMF (1.0 ml) was added dropwise to a solution of sodium hydride (16 mg) in anhydrous DMF (1.0 ml), and the resulting mixture was stirred at room temperature for 30 minutes. To the reaction solution, a solution of 4-acetoxybenzyl chloride (0.04 ml) in anhydrous DMF (0.5 ml) was added, and the resulting mixture was stirred at room temperature overnight. Saturated brine was added to the reaction solution and the resulting mixture was extracted with chloroform. Organic layer was dried over anhydrous sodium sulfate. After removing anhydrous sodium sulfate by filtration, the filtrate was concentrated. The residue was purified by column chromatography (silica gel, eluent: hexane/ethyl acetate=6/1) to obtain (4-acetoxybenzyl)-(4-iodophenyl)pyrimidin-2-ylamine (67 mg). NMR (H$^1$, CDCl$_3$): δ 2.28 (3H, s), 5.22 (2H, s), 6.63 (1H, t, J=4.6 Hz), 6.98-7.02 (4H, m), 7.26 (2H, d, J=8.1 Hz), 7.64-7.67 (2H, m), 8.34 (2H, d, J=4.6 Hz)

Reference Example 18

3-(N-(4-Iodophenyl)-N-(pyrimidin-2-yl)amino)propanenitrile

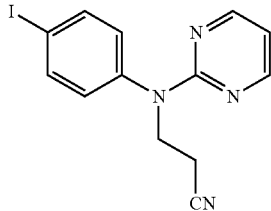 [SMILES: N#CCCN(c1ccc(I)cc1)c1ncccn1]

Under an argon atmosphere, a solution of N-(4-iodophenyl)pyrimidin-2-amine (100 mg) in anhydrous DMF (1.0 ml) was added to a suspension of sodium hydride (16 mg) in anhydrous DMF (1.0 ml), and the resulting mixture was stirred at room temperature for 30 minutes. To the reaction solution, a solution of 3-bromopropionitrile (0.04 ml) in anhydrous DMF (0.5 ml) was added, and the resulting mixture was stirred at room temperature overnight. Saturated brine was added to the reaction solution and the resulting mixture was extracted with chloroform. Organic layer was dried over anhydrous sodium sulfate. After removing anhydrous sodium sulfate by filtration, the filtrate was concentrated. The residue was purified by column chromatography (silica gel, eluent: hexane/chloroform=1/10) to obtain 3-(N-(4-iodophenyl)-N-(pyrimidin-2-yl)amino)propanenitrile (94 mg). NMR (H$^1$, CDCl$_3$): δ 2.82 (2H, t, J=6.8 Hz), 4.24 (2H, t, J=6.8 Hz), 6.68 (1H, t, J=4.9 Hz), 7.06-7.10 (2H, m), 7.74-7.78 (2H, m), 8.35 (2H, d, J=4.9 Hz)

Reference Example 19

N-Benzyl-N-(4-iodophenyl)pyrimidin-2-amine

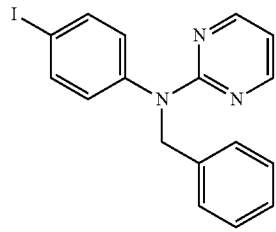

Under an argon atmosphere, N-(4-iodophenyl)pyrimidin-2-amine (75 mg) was added to a suspension of sodium hydride (16 mg) in anhydrous DMF (3 ml), and the resulting mixture was stirred at room temperature for 30 minutes. The reaction solution was cooled to 0° C. and benzyl bromide (0.039 ml) was added thereto, followed by stirring the resulting mixture at room temperature for 1 hour. Saturated brine was added to the reaction solution and the resulting mixture was extracted 3 times with ethyl acetate. Organic layers were washed 3 times with water and dried over anhydrous sodium sulfate. After removing anhydrous sodium sulfate by filtration, the filtrate was concentrated. The residue was purified by column chromatography (silica gel, eluent: ethyl acetate/hexane=1/15) to obtain N-benzyl-N-(4-iodophenyl)pyrimidin-2-amine (67 mg).

Reference Example 20

N-(4-Bromophenyl)-N-(4-methoxybenzyl)pyrimidin-2-amine

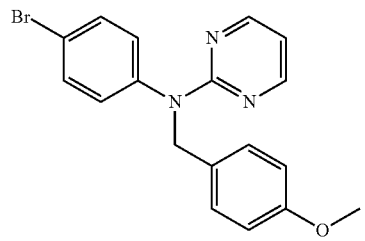 [SMILES: COc1ccc(CN(c2ccc(Br)cc2)c2ncccn2)cc1]

Under an argon atmosphere, N-(4-bromophenyl)pyrimidin-2-amine (75 mg) was added to a suspension of sodium hydride (16 mg) in anhydrous DMF (3 ml), and the resulting mixture was stirred at room temperature for 30 minutes. The reaction solution was cooled to 0° C. and 4-methoxybenzyl chloride (0.045 ml) was added thereto, followed by stirring the resulting mixture at room temperature for 1 hour. Saturated brine was added to the reaction solution and the resulting mixture was extracted 3 times with ethyl acetate. Organic layers were washed 3 times with water and once with saturated brine, and dried over anhydrous sodium sulfate. After removing anhydrous sodium sulfate by filtration, the filtrate was concentrated. The residue was purified by column chromatography (silica gel, eluent: ethyl acetate/hexane=1/10) to obtain N-(4-bromophenyl)-N-(4-methoxybenzyl)pyrimidin-2-amine (107 mg).

Reference Example 21

N-(4-Bromophenyl)-N-butylpyrimidin-2-amine

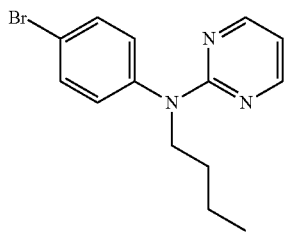 [SMILES: CCCCN(c1ccc(Br)cc1)c1ncccn1]

Under an argon atmosphere, N-(4-bromophenyl)pyrimidin-2-amine (160 mg) was added to a suspension of sodium hydride (33 mg) in anhydrous DMF (3 ml), and the resulting mixture was stirred at room temperature for 30 minutes. The reaction solution was cooled to 0° C. and n-butyl iodide (0.080 ml) was added thereto, followed by stirring the resulting mixture at room temperature for 1 hour, Saturated brine was added to the reaction solution and the resulting mixture was extracted 3 times with ethyl acetate. Organic layers were washed 3 times with water and once with saturated brine, and dried over anhydrous sodium sulfate. After removing anhydrous sodium sulfate by filtration, the filtrate was concentrated. The residue was purified by column chromatography (silica gel, eluent: ethyl acetate/hexane=1/10) to obtain N-(4-bromophenyl)-N-butylpyrimidin-2-amine (194 mg).

Reference Example 22

N-(4-Bromophenyl)-N-((pyridin-3-yl)methyl)pyrimidin-2-amine

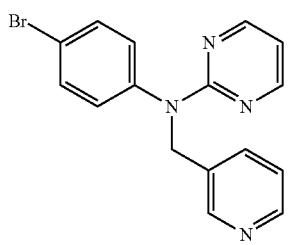 [SMILES: Brc1ccc(N(Cc2cccnc2)c2ncccn2)cc1]

Under an argon atmosphere, N-(4-bromophenyl)pyrimidin-2-amine (200 mg) was added to a suspension of sodium hydride (48 mg) in anhydrous DMF (8 ml), and the resulting mixture was stirred at room temperature for 30 minutes. The reaction solution was cooled to 0° C., and 3-chloromethylpyridine hydrochloride (600 mg) and triethylamine (1.00 ml) were added thereto, followed by stirring the resulting mixture at room temperature for 2 hours. Saturated brine was added to the reaction solution and the resulting mixture was extracted 3 times with ethyl acetate. Organic layers were washed 3 times with water and once with saturated brine, and dried over anhydrous sodium sulfate. After removing anhydrous sodium sulfate by filtration, the filtrate was concentrated. The residue was purified by column chromatography (silica gel, eluent: ethyl acetate/hexane=3/1) to obtain N-(4-bromophenyl)-N-((pyridin-3-yl)methyl)pyrimidin-2-amine (232 mg). NMR (H$^1$, CDCl$_3$): δ 5.23 (2H, s), 6.65 (1H, t, J=4.6 Hz), 7.08-7.12 (2H, m), 7.20 (1H, dd, J=7.8, 4.9 Hz), 7.46-7.50 (2H, m), 7.59-7.61 (1H, m), 8.35 (2H, d, J=4.6 Hz), 8.49 (1H, dd, J=4.9, 1.5 Hz), 8.54 (1H, d, J=2.2 Hz)

Reference Example 23

N-(4-Bromophenyl)-N-((thiazol-4-yl)methyl)pyrimidin-2-amine

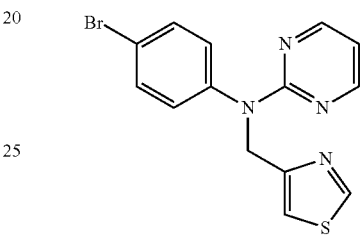

Under an argon atmosphere, N-(4-bromophenyl)pyrimidin-2-amine (200 mg) was added to a suspension of sodium hydride (48 mg) in anhydrous DMF (8 ml), and the resulting mixture was stirred at room temperature for 30 minutes. The reaction solution was cooled to 0° C., and thiazoylmethyl chloride hydrochloride (816 mg) and triethylamine (1.00 ml) were added thereto, followed by stirring the resulting mixture at room temperature for 2 hours. Saturated brine was added to the reaction solution and the resulting mixture was extracted 3 times with ethyl acetate. Organic layers were washed 3 times with water and once with saturated brine, and dried over anhydrous sodium sulfate. After removing anhydrous sodium sulfate by filtration, the filtrate was concentrated. The residue was purified by column chromatography (silica gel, eluent: ethyl acetate/hexane=1/3) to obtain N-(4-bromophenyl)-N-((thiazol-4-yl)methyl)pyrimidin-2-amine (190 mg).

Reference Example 24

N-(4-Iodophenyl)-4-methoxy-N-methylpyrimidin-2-amine

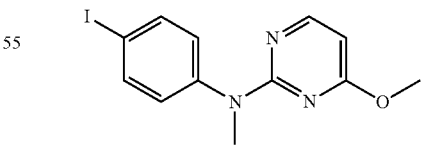

(1) Under an argon atmosphere, sodium hydride (100 mg) was added to a solution of 4-iodoaniline (220 mg) and 2-chloro-4-methoxypyrimidine (145 mg) in anhydrous DMF (10 ml), and the resulting mixture was stirred at 125° C. for 21 hours. The reaction solution was cooled to room temperature and water was added thereto, followed by extracting the resulting mixture with ethyl acetate. Organic layer was washed twice with water and once with saturated brine, and dried over anhydrous sodium sulfate. After removing anhydrous sodium sulfate by filtration, the filtrate was concentrated. The residue was purified by column chromatography (silica gel, eluent: hexane/ethyl acetate=10/1) to obtain N-(4-iodophenyl)-4-methoxypyrimidin-2-amine (46 mg).

(2) Under an argon atmosphere, N-(4-iodophenyl)-4-methoxypyrimidin-2-amine (46 mg) was added to a suspension of sodium hydride (11 mg) in anhydrous DMF (5 ml), and the resulting mixture was stirred at room temperature for 5 minutes. Methyl iodide (0.0096 ml) was added dropwise to the reaction solution, and the resulting mixture was stirred at room temperature for 23 hours. Water was added thereto and the resulting mixture was extracted with ethyl acetate. Organic layer was washed twice with water and once with saturated brine, and dried over anhydrous sodium sulfate. After removing anhydrous sodium sulfate by filtration, the filtrate was concentrated. The residue was purified by column chromatography (silica gel, eluent: hexane/ethyl acetate=3/1) to obtain N-(4-iodophenyl)-4-methoxy-N-methylpyrimidin-2-amine (46 mg).

Reference Example 25

N-(4-Iodophenyl)-4,6-dimethoxy-N-methylpyrimidin-2-amine

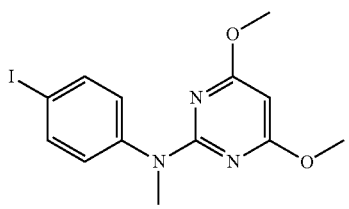 [SMILES: COc1cc(OC)nc(N(C)c2ccc(I)cc2)n1]

(1) In the same manner as in Reference Example 24-(1), 4-iodoaniline (220 mg) and 2-chloro-4,6-dimethoxypyrimidine (200 mg) were reacted in the presence of sodium hydride to obtain N-(4-iodophenyl)-4,6-dimethoxypyrimidin-2-amine (141 mg).

(2) In the same manner as in Reference Example 24-(2), sodium hydride (16 mg), N-(4-iodophenyl)-4,6-dimethoxypyrimidin-2-amine (140 mg) and methyl iodide (0.024 ml) were reacted to obtain N-(4-iodophenyl)-4,6-dimethoxy-N-methylpyrimidin-2-amine (118 mg).

Reference Example 26

N-(4-Bromophenyl)-N-phenylpyrimidin-2-amine

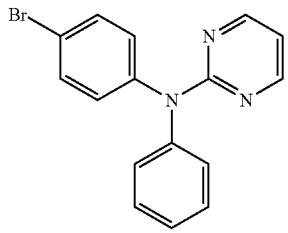 [SMILES: Brc1ccc(N(c2ccccc2)c2ncccn2)cc1]

Under an argon atmosphere, a suspension of N-(4-bromophenyl)pyrimidin-2-amine (250 mg), copper iodide (1.9 mg), trans-1,2-cyclohexanediamine (0.015 ml) and sodium-tert-butoxide (144 mg) in dioxane (1 ml) was stirred at 110° C. for 22 hours in a pressure-resistant test tube. The reaction solution was filtered and the filtrate was concentrated. The residue was purified by thin layer chromatography (silica gel, mobile phase: chloroform/ethyl acetate=5/1) to obtain N-(4-bromophenyl)-N-phenylpyrimidin-2-amine (56 mg).

Reference Example 27

Trifluoromethanesulfonic acid 4-[pyrimidin-2-yl-(tetrahydropyran-4-yl)amino]phenyl ester

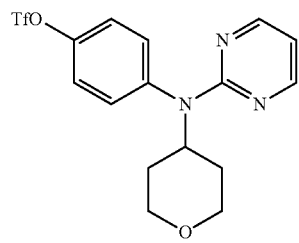 [SMILES: O=S(=O)(Oc1ccc(N(c2ncccn2)C2CCOCC2)cc1)C(F)(F)F]

(1) Acetic acid (0.856 ml) was added to a solution of p-anisidine (1.23 g) and 2-chloropyrimidine (1.72 g) in dioxane (20 ml), and the resulting mixture was stirred overnight while heating the mixture to reflux. After cooling the reaction solution to room temperature, 1 N aqueous sodium hydroxide solution was added thereto and the resulting mixture was extracted 3 times with chloroform, followed by drying the organic layers over anhydrous sodium sulfate. After removing anhydrous sodium sulfate by filtration, the filtrate was concentrated. The residue was reprecipitated from chloroform/hexane mixed solvent to obtain N-(4-methoxyphenyl)pyrimidin-2-amine (1.39 g).

(2) Under an argon atmosphere, p-toluenesulfonyl chloride (3.82 g) was added to a solution of tetrahydro-2H-pyran-4-ol (2.00 g) in pyridine (50 ml) at 0° C., and the resulting mixture was stirred at room temperature overnight. After adding 1 N hydrochloric acid thereto, the resulting mixture was extracted 3 times with ethyl acetate. Organic layers were washed 3 times with water and dried over anhydrous sodium sulfate. After removing anhydrous sodium sulfate by filtration, the filtrate was concentrated. The residue was purified by column chromatography (silica gel, eluent: ethyl acetate/hexane=1/6) to obtain tetrahydro-2H-pyran-4-yl-4-methylbenzenesulfonate (2.92 g).

(3) Under an argon atmosphere, N-4-(methoxyphenyl)pyrimidin-2-amine (402 mg) was added to a suspension of sodium hydride (120 mg) in anhydrous DMF (15 ml), and the resulting mixture was stirred at room temperature for 30 minutes. A solution of tetrahydro-2H-pyran-4-yl-4-methylbenzenesulfonate (2.92 g) in anhydrous DMF (10 ml) was added to the reaction solution, and the resulting mixture was stirred at 50° C. for 24 hours. Sodium hydride (120 mg) was further added to the reaction solution, and the resulting mixture was stirred at 50° C. for 24 hours. The solution was cooled to room temperature, and saturated brine was added thereto, followed by extracting the resulting mixture 3 times with ethyl acetate. Organic layers were washed 3 times with water and dried over anhydrous sodium sulfate. After removing anhydrous sodium sulfate by filtration, the filtrate was concentrated. The residue was purified by column chromatography (silica gel, eluent: ethyl acetate/hexane=1/3) to obtain N-(tetrahydro-2H-pyran-4-yl)-N-(4-methoxyphenyl)pyrimidin-2-amine (342 mg).

(4) A mixture of N-(tetrahydro-2H-pyran-4-yl)-N-(4-methoxyphenyl)pyrimidin-2-amine (342 mg) and pyridine hydrochloride (2.00 g) was heated to 170° C. and stirred for 1 hour. Pyridine hydrochloride (1.00 g) was further added to the reaction solution, and the resulting mixture was stirred at 170° C. for 1 hour. The reaction solution was allowed to cool to room temperature and saturated brine was added thereto, followed by extracting the resulting mixture 3 times with ethyl acetate. Organic layers were washed 3 times with water and dried over anhydrous sodium sulfate. After removing anhydrous sodium sulfate by filtration, the filtrate was concentrated. To a suspension of the obtained residue and potassium carbonate (498 mg) in THF (15 ml), N-phenylbis(trifluoromethanesulfonimide) (514 mg) was added, and the resulting mixture was stirred at room temperature for 5 hours. Saturated brine was added to the reaction solution, and the resulting mixture was extracted 3 times with ethyl acetate, followed by drying the organic layers over anhydrous sodium sulfate. After removing anhydrous sodium sulfate by filtration, the filtrate was concentrated. The residue was purified by column chromatography (silica gel, eluent: ethyl acetate/hexane=1/5) to obtain trifluoromethanesulfonic acid 4-[pyrimidin-2-yl-(tetrahydropyran-4-yl)amino]phenyl ester (228 mg). NMR (H$^1$, CDCl$_3$): δ 1.52-1.61 (2H, m), 1.83-1.87 (2H, m), 3.57 (2H, dt, J=12.0, 1.6 Hz), 4.00 (2H, dd, J=11.6, 4.8 Hz), 4.97-5.03 (1H, m), 6.59 (1H, t, J=4.8 Hz), 7.19-7.23 (2H, m), 7.34-7.37 (2H, m), 8.29 (2H, d, J=4.8 Hz)

Reference Example 28

N-(4-Iodophenyl)-N-(3-methyl-2-butenyl)pyrimidin-2-amine

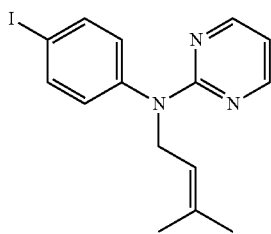 [SMILES: CC(C)=CCN(c1ccc(I)cc1)c1ncccn1]

In the same manner as in Reference Example 13, N-(4-iodophenyl)pyrimidin-2-amine (150 mg) and 1-bromo-3-methyl-2-butene (90 mg) were reacted in the presence of sodium hydride to obtain N-(4-iodophenyl)-N-(3-methyl-2-butenyl)pyrimidin-2-amine (175 mg).

Reference Example 29

N-(Cyclopropylmethyl)-N-(4-iodophenyl)pyrimidin-2-amine

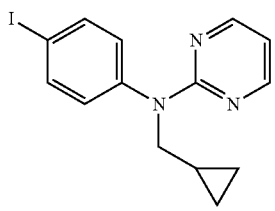 [SMILES: Ic1ccc(N(CC2CC2)c2ncccn2)cc1]

In the same manner as in Reference Example 13, N-(4-iodophenyl)pyrimidin-2-amine (150 mg) and cyclopropylmethyl bromide (82 mg) were reacted in the presence of sodium hydride to obtain N-(cyclopropylmethyl)-N-(4-iodophenyl)pyrimidin-2-amine (162 mg).

Reference Example 30

N-(4-Iodophenyl)-N-isobutylpyrimidin-2-amine

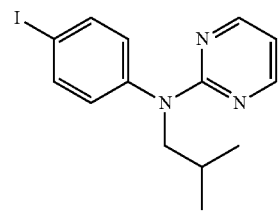 [SMILES: CC(C)CN(c1ccc(I)cc1)c1ncccn1]

In the same manner as in Reference Example 13, N-(4-iodophenyl)pyrimidin-2-amine (150 mg) and isobutyl bromide (83 mg) were reacted in the presence of sodium hydride to obtain N-(4-iodophenyl)-N-isobutylpyrimidin-2-amine (167 mg).

Reference Example 31

N-(4-Iodophenyl)-N-propylpyrimidin-2-amine

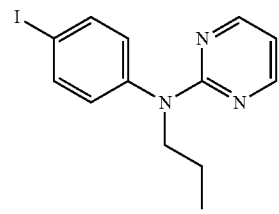 [SMILES: CCCN(c1ccc(I)cc1)c1ncccn1]

In the same manner as in Reference Example 13, N-(4-iodophenyl)pyrimidin-2-amine (300 mg) and propyl bromide (0.11 ml) were reacted in the presence of sodium hydride to obtain N-(4-iodophenyl)-N-propylpyrimidin-2-amine (348 mg).

Reference Example 32

N-(4-Iodophenyl)-N-((pyridin-4-yl)methyl)pyrimidin-2-amine

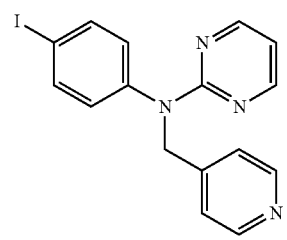 [SMILES: Ic1ccc(N(Cc2ccncc2)c2ncccn2)cc1]

In the same manner as in Reference Example 22, N-(4-iodophenyl)pyrimidin-2-amine (300 mg) and 4-bromomethylpyridine hydrobromide (307 mg) were reacted in the presence of sodium hydride to obtain N-(4-iodophenyl)-N-((pyridin-4-yl)methyl)pyrimidin-2-amine (93 mg).

Reference Example 33

N-(4-Iodophenyl)-N-((pyridin-2-yl)methyl)pyrimidin-2-amine

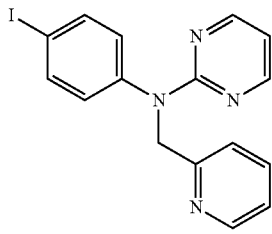 [SMILES: Ic1ccc(N(Cc2ccccn2)c2ncccn2)cc1]

In the same manner as in Reference Example 22, N-(4-iodophenyl)pyrimidin-2-amine (300 mg) and 2-bromomethylpyridine hydrobromide (307 mg) were reacted in the presence of sodium hydride to obtain N-(4-iodophenyl)-N-((pyridin-2-yl)methyl)pyrimidin-2-amine (282 mg).

Reference Example 34

2-Amino-5-[4-(methyl-pyrimidin-2-ylamino)phenyl]pent-4-enoic acid methyl ester

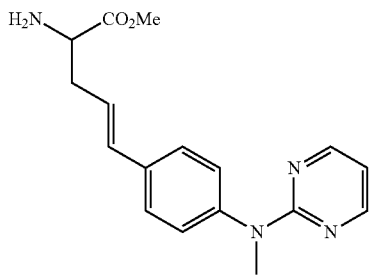 [SMILES: COC(=O)C(N)C/C=C/c1ccc(N(C)c2ncccn2)cc1]

(1) Allylglycine (1.82 g) was dissolved in 1N aqueous sodium hydroxide solution (60 ml), and di-tert-butyl dicarbonate (4.15 g) was added thereto, followed by stirring the resulting mixture at room temperature for 11 hours. Di-tert-butyl dicarbonate (4.15 g) was further added to the reaction solution and the resulting mixture was stirred at room temperature overnight. After adding water to the reaction solution and washing it with ether, the solution was acidified with 3N hydrochloric acid. The solution was extracted twice with ethyl acetate. Organic layers were washed with saturated brine and dried over anhydrous sodium sulfate. After removing anhydrous sodium sulfate by filtration, the filtrate was concentrated. The residue was recrystallized from hexane/ethyl acetate mixed solvent to obtain N-Boc-allylglycine (3.09 g).
(2) Trimethylsilyldiazomethane (2N, in hexane) (12 ml) was added dropwise to a solution of N-Boc-allylglycine (3.09 g) in dichloromethane/methanol (2/1) mixture (30 ml), and the resulting mixture was stirred at room temperature for 3 hours. After concentrating the reaction solution, the residue was purified by column chromatography (silica gel, eluent: cyclohexane/ethyl acetate=20/1→10/1) to obtain N-Boc-allylglycine methyl ester (3.11 g). NMR (H¹, CDCl₃): δ 2.43-2.55 (2H, m), 3.72 (3H, s), 4.34-4.39 (1H, brm), 5.02 (1H, brs), 5.09-5.13 (2H, m), 5.62-5.72 (1H, m)
(3) Under an argon atmosphere, palladium acetate (54 mg) and tris(2-methylphenyl)phosphine (70 mg) were added to a suspension of N-Boc-allylglycine methyl ester (1.03 g), N-(4-iodophenyl)-N-methylpyrimidin-2-amine (1.40 g) and potassium carbonate (933 mg) in DMF (15 ml), and the resulting mixture was stirred at 80° C. overnight. The reaction solution was allowed to cool to room temperature and ethyl acetate was added thereto. The solution was washed 3 times with water and once with saturated brine, and dried over anhydrous sodium sulfate. After removing anhydrous sodium sulfate by filtration, the filtrate was concentrated. The residue was purified by column chromatography (silica gel, eluent: cyclohexane/ethyl acetate=20/1→4/1). The obtained solid was recrystallized from hexane/ethyl acetate mixed solvent to obtain 2-tert-butoxycarbonylamino-5-[4-(methyl-pyrimidin-2-ylamino)phenyl]pent-4-enoic acid methyl ester (976 mg).
(4) Trifluoroacetic acid (2 ml) was added to a solution of 2-tert-butoxycarbonylamino-5-[4-(methyl-pyrimidin-2-ylamino)phenyl]pent-4-enoic acid methyl ester (976 mg) in dichloromethane (20 ml), and the resulting mixture was stirred at room temperature for 4.5 hours. Water was added to the reaction solution, and sodium hydrogen carbonate was added thereto in small portions to neutralize it, followed by extracting the resulting solution twice with chloroform. Organic layers were washed with saturated brine and dried over anhydrous sodium sulfate. After removing anhydrous sodium sulfate by filtration, the filtrate was concentrated to dryness to obtain 2-amino-5-[4-(methyl-pyrimidin-2-ylamino)phenyl]pent-4-enoic acid methyl ester (599 mg). NMR (H¹, CDCl₃): δ 2.58-2.64 (2H, brm), 3.48-3.58 (1H, brm), 3.52 (3H, s), 3.75 (3H, s), 6.07-6.14 (1H, m), 6.49 (1H, d, J=5.6 Hz), 6.57 (1H, t, J=4.6 Hz), 7.26 (2H, d, J=8.1 Hz), 7.38 (2H, d, J=8.3 Hz), 8.34 (2H, d, J=4.6 Hz)

Reference Example 35

2-(2,6-Dichlorobenzamido)pent-4-enoic acid methyl ester

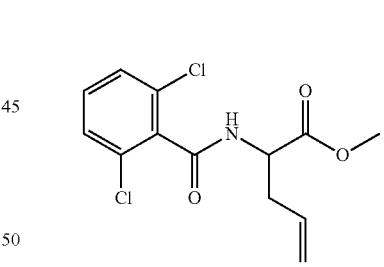

(1) Allylglycine (10.11 g) was dissolved in a mixed solvent of 2N aqueous sodium hydroxide solution (176 ml) and dioxane (175 ml), and 2,6-dichlorobenzoyl chloride (15.10 ml) was added dropwise thereto, followed by stirring the resulting mixture at room temperature for 10 hours. After concentrating the reaction solution to remove dioxane, water (150 ml) was added thereto and the resulting solution was washed with ether. Aqueous layer was acidified by adding 3N hydrochloric acid in small portions thereto, and extracted 3 times with ethyl acetate. Organic layers were washed with saturated brine and dried over anhydrous sodium sulfate. After removing anhydrous sodium sulfate by filtration, the filtrate was concentrated. The residue was recrystallized from hexane/ethyl acetate mixed solvent to obtain 2-(2,6-dichlorobenzamido)pent-4-enoic acid (23.48 g).

(2) Under an argon atmosphere, a solution of 2-(2,6-dichlorobenzamido)pent-4-enoic acid (23.48 g) in methanol (250 ml) was cooled to 0° C. Thionyl chloride (10.70 ml) was added dropwise to the solution while keeping the reaction temperature not higher than 10° C., and thereafter the resulting mixture was stirred at room temperature for 5.5 hours. Water was added to the reaction solution, and sodium hydrogen carbonate was added thereto in small portions to neutralize it. After concentrating the reaction solution to remove methanol, aqueous layer was extracted twice with ethyl acetate. Organic layers were washed 3 times with water and once with saturated brine, and dried over anhydrous sodium sulfate. After removing anhydrous sodium sulfate by filtration, the filtrate was concentrated. The residue was recrystallized from hexane/ethyl acetate mixed solvent to obtain 2-(2,6-dichlorobenzamido)pent-4-enoic acid methyl ester (21.70 g). NMR (H$^1$, CDCl$_3$): δ 2.55-2.61 (1H, m), 2.68-2.75 (1H, m), 3.72 (3H, s), 4.88 (1H, td, J=7.8, 5.4 Hz), 5.06-5.13 (2H, m), 5.64-5.74 (1H, m), 6.33 (1H, brd, J=7.1 Hz), 7.17-7.26 (3H, m)

Reference Example 36

2-(2,6-Difluorobenzamido)pent-4-enoic acid methyl ester

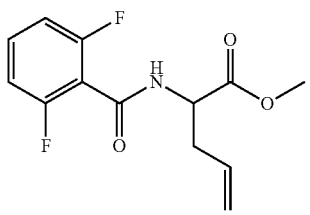 [SMILES: C=CCC(NC(=O)c1c(F)cccc1F)C(=O)OC]

(1) In the same manner as in Reference Example 35-(1), allylglycine (285 mg) was reacted with 2,6-difluorobenzoyl chloride (0.374 ml) to obtain 2-(2,6-difluorobenzamido)pent-4-enoic acid (471 mg).
(2) In the same manner as in Reference Example 35-(2), thionyl chloride (0.242 ml) was reacted with a solution of 2-(2,6-difluorobenzamido)pent-4-enoic acid (471 mg) in methanol (20 ml) to obtain 2-(2,6-difluorobenzamido)pent-4-enoic acid methyl ester (430 mg).

Reference Example 37

2-(2,6-Dichlorobenzamido)pent-4-ynoic acid methyl ester

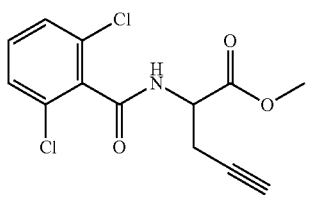 [SMILES: C#CCC(NC(=O)c1c(Cl)cccc1Cl)C(=O)OC]

(1) Propargylglycine (5.00 g) was dissolved in a mixed solvent of 2N aqueous sodium hydroxide solution (100 ml) and dioxane (100 ml), and 2,6-dichlorobenzoyl chloride (9.45 ml) was added dropwise thereto at 0° C., followed by stirring the resulting mixture at room temperature overnight. Water was added to the reaction solution, and the solution was washed with ether. Aqueous layer was acidified by adding 3N hydrochloric acid in small portions thereto and extracted with ethyl acetate, and organic layer was dried over anhydrous sodium sulfate. After removing anhydrous sodium sulfate by filtration, the filtrate was concentrated to dryness to obtain 2-(2,6-dichlorobenzamido)pent-4-ynoic acid.

(2) Under an argon atmosphere, a solution of thionyl chloride (5.25 ml) in absolute methanol (200 ml) was cooled to 0° C. To the solution, a solution of 2-(2,6-dichlorobenzamido)pent-4-ynoic acid obtained in (1) in methanol (50 ml) was added dropwise, and the resulting mixture was stirred at room temperature overnight. Water was added to the reaction solution, and the solution was extracted with ethyl acetate. Organic layer was washed with saturated aqueous sodium hydrogen carbonate solution and dried over anhydrous sodium sulfate. After removing anhydrous sodium sulfate by filtration, the filtrate was concentrated. A mixed solvent of ethyl acetate/ether (1/1) (300 ml) was added to the residue, and insoluble matter was removed by filtration. The filtrate was concentrated and the residue was recrystallized twice from hexane/ethyl acetate mixed solvent to obtain 2-(2,6-dichlorobenzamido)pent-4-ynoic acid methyl ester (9.61 g).

Reference Example 38

(S)-2-(2,6-Dichlorobenzamido)pent-4-enoic acid methyl ester

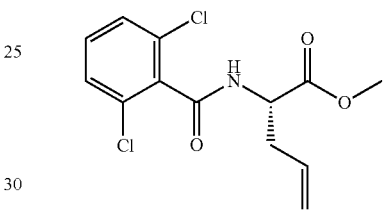

(1) In a mixed solvent of 2N aqueous sodium hydroxide solution (27.4 ml) and THF (55 ml), L-allylglycine (5.22 g) was dissolved, and 2,6-dichlorobenzoyl chloride (7.79 ml) was added dropwise thereto, followed by stirring the resulting mixture at room temperature for 1 hour. After concentrating the reaction solution to remove methanol, water (100 ml) was added thereto and the resulting mixture was washed with ether. Aqueous layer was acidified by adding 3N hydrochloric acid in small portions thereto, and extracted 3 times with ethyl acetate. Organic layers were washed with saturated brine and dried over anhydrous sodium sulfate. After removing anhydrous sodium sulfate by filtration, the filtrate was concentrated. The residue was recrystallized from hexane/ethyl acetate mixed solvent to obtain (S)-2-(2,6-dichlorobenzamido)pent-4-enoic acid (11.65 g). NMR (H$^1$, CDCl$_3$): δ 2.66-2.73 (1H, m), 2.80-2.86 (1H, m), 4.99 (1H, td, J=7.6, 5.6 Hz), 5.18-5.25 (2H, m), 5.76-5.86 (1H, m), 6.39 (1H, brd, J=7.6 Hz), 7.25-7.34 (3H, m)
(2) Under an argon atmosphere, a solution of (S)-2-(2,6-dichlorobenzamido)pent-4-enoic acid (11.46 g) in methanol (120 ml) was cooled to 0° C. Thionyl chloride (5.22 ml) was added dropwise to the solution while keeping the reaction temperature not higher than 10° C., and thereafter the resulting mixture was stirred at room temperature for 3 hours. Water was added to the reaction solution, and sodium hydrogen carbonate was added thereto in small portions to neutralize it. After concentrating the reaction solution to remove methanol, aqueous layer was extracted twice with ethyl acetate. Organic layers were washed 3 times with water and once with saturated brine, and dried over anhydrous sodium sulfate. After removing anhydrous sodium sulfate by filtration, the filtrate was concentrated. The residue was recrystallized from hexane/ethyl acetate mixed solvent to obtain (S)-2-(2,6-dichlorobenzamido)pent-4-enoic acid methyl ester (11.68 g). NMR (H$^1$, CDCl$_3$): δ 2.62-2.69 (1H, m), 2.76-2.83 (1H, m), 3.79 (3H, s), 4.96 (1H, td, J=7.8, 5.4 Hz), 5.14-5.21 (2H, m), 5.72-5.82 (1H, m), 6.42 (1H, brd, J=6.8 Hz), 7.25-7.34 (3H, m)

Example 1

(E)-2-(2,6-Dichlorobenzamido)-5-[4-(4-hydroxytetrahydropyran-4-yl)-phenyl]pent-4-enoic acid methyl ester

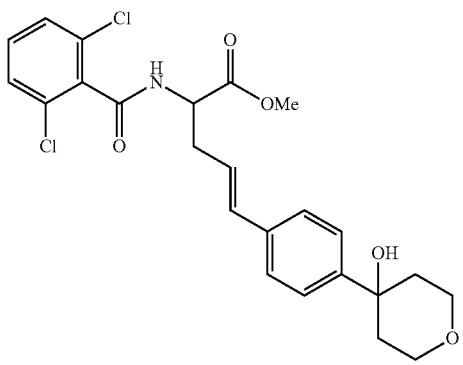 [SMILES: COC(=O)C(C/C=C/c1ccc(C2(O)CCOCC2)cc1)NC(=O)c1c(Cl)cccc1Cl]

Under an argon atmosphere, palladium acetate (4.7 mg) and tris(2-methylphenyl)phosphine (6.1 mg) were added to a suspension of 2-(2,6-dichlorobenzamido)pent-4-enoic acid methyl ester (60.4 mg), tetrahydro-4-(4-iodophenyl)-2H-pyran-4-ol (60.8 mg) and potassium carbonate (41.5 mg) in DMF (4 ml), and the resulting mixture was stirred at 80° C. for 6 hours. After cooling the reaction solution to room temperature, ethyl acetate was added thereto and the solution was washed 3 times with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=2/1→1/4) and thereafter by thin layer chromatography (silica gel, mobile phase: cyclohexane/ethyl acetate=1/1) to obtain (E)-2-(2,6-dichlorobenzamido)-5-[4-(4-hydroxytetrahydropyran-4-yl)-phenyl]pent-4-enoic acid methyl ester (56 mg).

Example 2

(E)-2-(2,6-Dichlorobenzamido)-5-[4-(4-hydroxytetrahydropyran-4-yl)-phenyl]pent-4-enoic acid

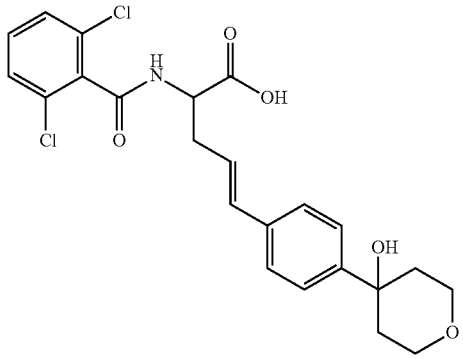 [SMILES: O=C(NC(C/C=C/c1ccc(C2(O)CCOCC2)cc1)C(=O)O)c1c(Cl)cccc1Cl]

To a solution of (E)-2-(2,6-dichlorobenzamido)-5-[4-(4-hydroxytetrahydropyran-4-yl)-phenyl]pent-4-enoic acid methyl ester (56 mg) in THF (1.76 ml), 0.1N aqueous sodium hydroxide solution (1.76 ml) was added, and the resulting mixture was stirred at room temperature for 2 hours. After washing the reaction solution with ether, aqueous layer was acidified by adding 1N hydrochloric acid thereto and extracted twice with ethyl acetate. Organic layers were washed with saturated brine and dried over anhydrous sodium sulfate. After removing anhydrous sodium sulfate by filtration, the filtrate was concentrated to dryness to obtain (E)-2-(2,6-dichlorobenzamido)-5-[4-(4-hydroxytetrahydropyran-4-yl)-phenyl]pent-4-enoic acid (48 mg).

Example 3

(E)-2-(2,6-Dichlorobenzamido)-5-[4-(4-methoxytetrahydropyran-4-yl)-phenyl]pent-4-enoic acid methyl ester

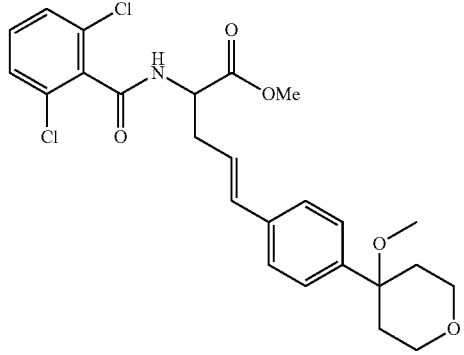 [SMILES: COC(=O)C(C/C=C/c1ccc(C2(OC)CCOCC2)cc1)NC(=O)c1c(Cl)cccc1Cl]

In the same manner as in Example 1, 2-(2,6-dichlorobenzamido)pent-4-enoic acid methyl ester (2.11 g) was reacted with tetrahydro-4-(4-iodophenyl)-4-methoxy-2H-pyran (2.22 g) in the presence of potassium carbonate (1.45 g), palladium acetate (81.7 mg) and tris(2-methylphenyl)phosphine (106.2 mg) to obtain (E)-2-(2,6-dichlorobenzamido)-5-[4-(4-methoxytetrahydropyran-4-yl)-phenyl]pent-4-enoic acid methyl ester (2.74 g). Column chromatography (silica gel, eluent: cyclohexane/chloroform=2/1→cyclohexane/ethyl acetate=10/1→cyclohexane/ethyl acetate=4/1) was used for purification.

Example 4

(E)-2-(2,6-Dichlorobenzamido)-5-[4-(4-methoxytetrahydropyran-4-yl)-phenyl]pent-4-enoic acid

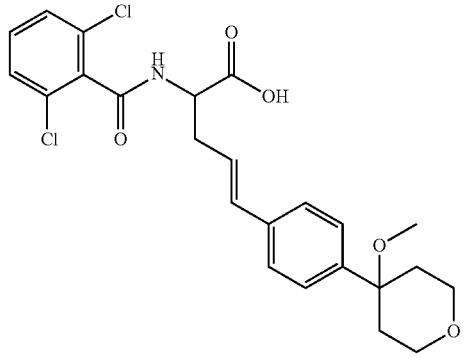 [SMILES: COC1(c2ccc(/C=C/CC(NC(=O)c3c(Cl)cccc3Cl)C(=O)O)cc2)CCOCC1]

In the same manner as in Example 2, 0.1N aqueous sodium hydroxide solution (63.1 ml) was added to a solution of (E)-2-(2,6-dichlorobenzamido)-5-[4-(4-methoxytetrahydropyran-4-yl)-phenyl]pent-4-enoic acid methyl ester (2.70 g) in THF (63.1 ml) to hydrolyze it to obtain (E)-2-(2,6-dichlorobenzamido)-5-[4-(4-methoxytetrahydropyran-4-yl)-phenyl]pent-4-enoic acid (2.50 g).

Example 5

(E)-2-(2,6-Dichlorobenzamido)-5-[4-(4-ethoxytetrahydropyran-4-yl)-phenyl]pent-4-enoic acid methyl ester

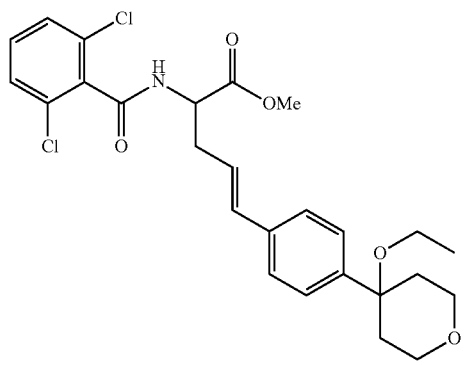 [SMILES: CCOC1(c2ccc(/C=C/CC(NC(=O)c3c(Cl)cccc3Cl)C(=O)O)cc2)CCOCC1]

In the same manner as in Example 1,2-(2,6-dichlorobenzamido)pent-4-enoic acid methyl ester (60.4 mg) was reacted with tetrahydro-4-(4-iodophenyl)-4-ethoxy-2H-pyran (66.4 mg) to obtain (E)-2-(2,6-dichlorobenzamido)-5-[4-(4-ethoxytetrahydropyran-4-yl)-phenyl]pent-4-enoic acid methyl ester (68.9 mg). Column chromatography (silica gel, eluent: cyclohexane/chloroform=2/1→cyclohexane/ethyl acetate=4/1) was used for purification.

Example 6

(E)-2-(2,6-Dichlorobenzamido)-5-[4-(4-ethoxytetrahydropyran-4-yl)-phenyl]pent-4-enoic acid

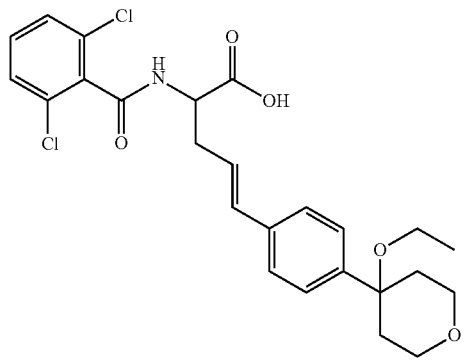

In the same manner as in Example 2, (E)-2-(2,6-dichlorobenzamido)-5-[4-(4-ethoxytetrahydropyran-4-yl)-phenyl]pent-4-enoic acid methyl ester (68.9 mg) was hydrolyzed to obtain (E)-2-(2,6-dichlorobenzamido)-5-[4-(4-ethoxytetrahydropyran-4-yl)-phenyl]pent-4-enoic acid (59.8 mg).

Example 7

(E)-2-(2,6-Dichlorobenzamido)-5-[4-(tetrahydro-4-(methoxymethyl)-2H-pyran-4-yl)phenyl]pent-4-enoic acid methyl ester

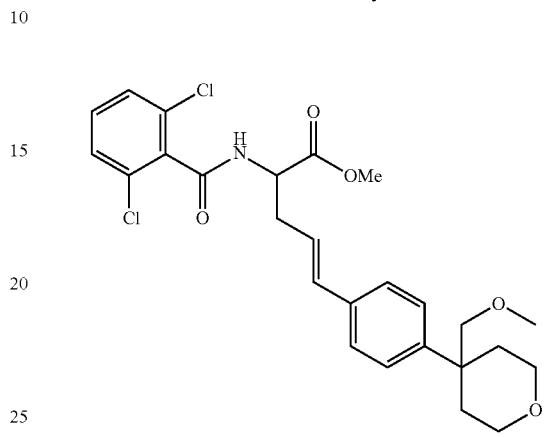

In the same manner as in Example 1,2-(2,6-dichlorobenzamido)pent-4-enoic acid methyl ester (78 mg) was reacted with tetrahydro-4-(4-bromophenyl)-4-(methoxymethyl)-2H-pyran (88 mg) to obtain (E)-2-(2,6-dichlorobenzamido)-5-[4-(tetrahydro-4-(methoxymethyl)-2H-pyran-4-yl)phenyl]pent-4-enoic acid methyl ester (97 mg). Column chromatography (silica gel, eluent: hexane/ethyl acetate=2/1) was used for purification.

Example 8

(E)-2-(2,6-Dichlorobenzamido)-5-[4-(tetrahydro-4-(methoxymethyl)-2H-pyran-4-yl)phenyl]pent-4-enoic acid sodium salt

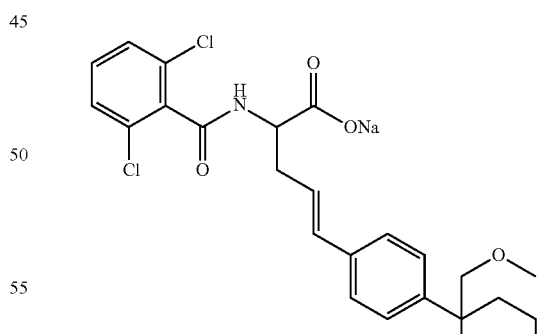

To a solution of (E)-2-(2,6-dichlorobenzamido)-5-[4-(tetrahydro-4-(methoxymethyl)-2H-pyran-4-yl)phenyl]pent-4-enoic acid methyl ester (86 mg) in THF (1.7 ml), 0.1N aqueous sodium hydroxide solution (1.7 ml) was added, and the resulting mixture was stirred at room temperature for 2 hours. After washing the reaction solution with ether, aqueous layer was concentrated to obtain (E)-2-(2,6-dichlorobenzamido)-

5-[4-(tetrahydro-4-(methoxymethyl)-2H-pyran-4-yl)phenyl]pent-4-enoic acid sodium salt (66 mg).

Example 9

(E)-2-(2,6-Dichlorobenzamido)-5-[4-(4-methoxyoxepan-4-yl)phenyl]pent-4-enoic acid methyl ester

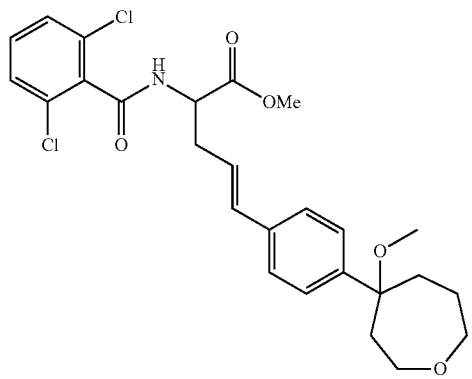

In the same manner as in Example 1, 2-(2,6-dichlorobenzamido)pent-4-enoic acid methyl ester (46 mg) was reacted with 4-(4-iodophenyl)-4-methoxyoxepane (60 mg) to obtain (E)-2-(2,6-dichlorobenzamido)-5-[4-(4-methoxyoxepan-4-yl)phenyl]pent-4-enoic acid methyl ester (66 mg). Column chromatography (silica gel, eluent: hexane/ethyl acetate=2/1) was used for purification.

Example 10

(E)-2-(2,6-Dichlorobenzamido)-5-[4-(4-methoxyoxepan-4-yl)phenyl]pent-4-enoic acid sodium salt

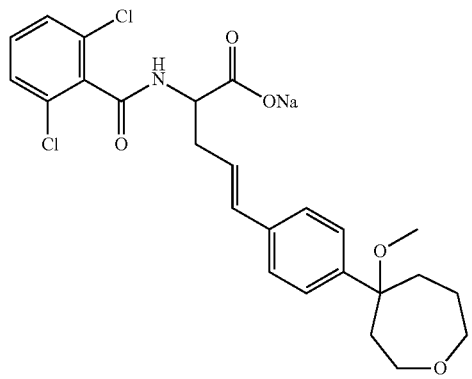

In the same manner as in Example 8, (E)-2-(2,6-dichlorobenzamido)-5-[4-(4-methoxyoxepan-4-yl)phenyl]pent-4-enoic acid methyl ester (57 mg) was hydrolyzed to obtain (E)-2-(2,6-dichlorobenzamido)-5-[4-(4-methoxyoxepan-4-yl)phenyl]pent-4-enoic acid sodium salt (18 mg).

Example 11

(E)-2-(2,6-Dichlorobenzamido)-5-[4-(pyrimidin-2-yloxy)phenyl]pent-4-enoic acid methyl ester

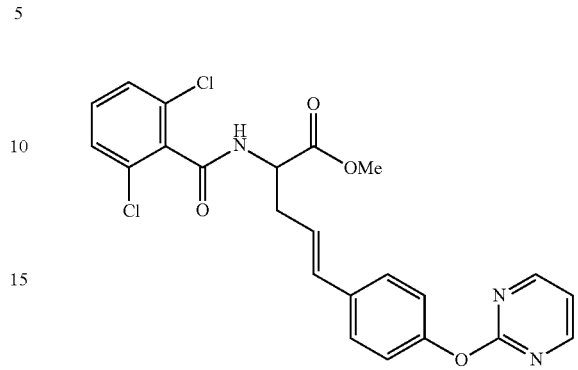

In the same manner as in Example 1, 2-(2,6-dichlorobenzamido)pent-4-enoic acid methyl ester (54.4 mg) was reacted with 2-(4-iodophenoxy)pyrimidine (59.2 mg) to obtain (E)-2-(2,6-dichlorobenzamido)-5-[4-(pyrimidin-2-yloxy)phenyl]pent-4-enoic acid methyl ester (53.0 mg). Thin layer chromatography (silica gel, mobile phase: cyclohexane/ethyl acetate=10/1) was used for purification.

Example 12

(E)-2-(2,6-Dichlorobenzamido)-5-[4-(pyrimidin-2-yloxy)phenyl]pent-4-enoic acid

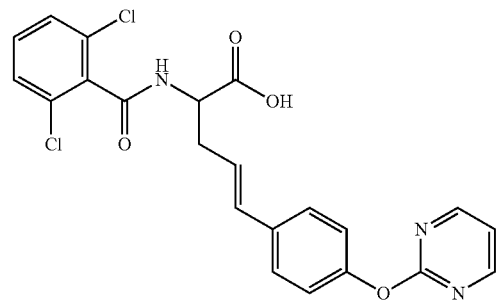 [SMILES: O=C(NC(C/C=C/c1ccc(Oc2ncccn2)cc1)C(=O)O)c1c(Cl)cccc1Cl]

In the same manner as in Example 2, (E)-2-(2,6-dichlorobenzamido)-5-[4-(pyrimidin-2-yloxy)phenyl]pent-4-enoic acid methyl ester (97.2 mg) was hydrolyzed to obtain (E)-2-(2,6-dichlorobenzamido)-5-[4-(pyrimidin-2-yloxy)phenyl]pent-4-enoic acid (77.5 mg).

Example 13

(E)-2-(2,6-Dichlorobenzamido)-5-[4-(5-ethylpyrimidin-2-yloxy)phenyl]pent-4-enoic acid methyl ester

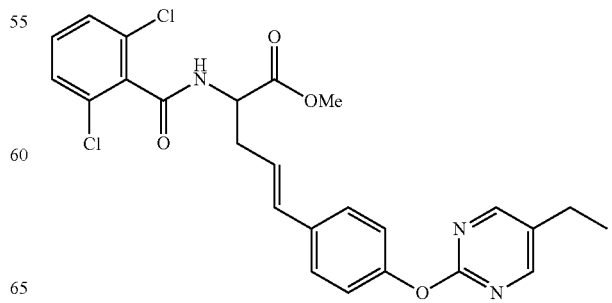

In the same manner as in Example 1,2-(2,6-dichlorobenzamido)pent-4-enoic acid methyl ester (50.0 mg) was reacted with 2-(4-iodophenoxy)-5-ethylpyrimidine (54.1 mg) to obtain (E)-2-(2,6-dichlorobenzamido)-5-[4-(5-ethylpyrimidin-2-yloxy)phenyl]pent-4-enoic acid methyl ester (62.2 mg). Column chromatography (chloroform) and thin layer chromatography (cyclohexane/ethyl acetate=1/2) were used for purification.

Example 14

(E)-2-(2,6-Dichlorobenzamido)-5-[4-(5-ethylpyrimidin-2-yloxy)phenyl]pent-4-enoic acid sodium salt

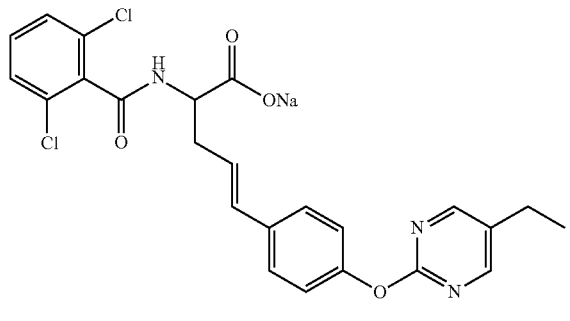

In the same manner as in Example 8, (E)-2-(2,6-dichlorobenzamido)-5-[4-(5-ethylpyrimidin-2-yloxy)phenyl]pent-4-enoic acid methyl ester (62.2 mg) was hydrolyzed to obtain (E)-2-(2,6-dichlorobenzamido)-5-[4-(5-ethylpyrimidin-2-yloxy)phenyl]pent-4-enoic acid sodium salt (45.1 mg).

Example 15

(E)-2-(2,6-Dichlorobenzamido)-5-[4-(4-methoxypyrimidin-2-yloxy)phenyl]pent-4-enoic acid methyl ester

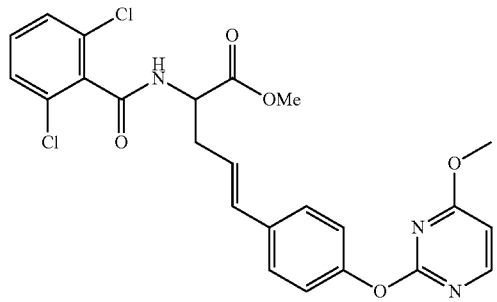 [SMILES: COC(=O)C(C/C=C/c1ccc(Oc2nccc(OC)n2)cc1)NC(=O)c1c(Cl)cccc1Cl]

In the same manner as in Example 1,2-(2,6-dichlorobenzamido)pent-4-enoic acid methyl ester (60 mg) was reacted with 2-(4-iodophenoxy)-4-methoxypyrimidine (78 mg) to obtain (E)-2-(2,6-dichlorobenzamido)-5-[4-(4-methoxypyrimidin-2-yloxy)phenyl]pent-4-enoic acid methyl ester (32 mg). Column chromatography (silica gel, eluent: hexane/ethyl acetate=2/1→cyclohexane/chloroform=1/1→1/10→0/1) was used for purification.

Example 16

(E)-2-(2,6-Dichlorobenzamido)-5-[4-(4-methoxypyrimidin-2-yloxy)phenyl]pent-4-enoic acid

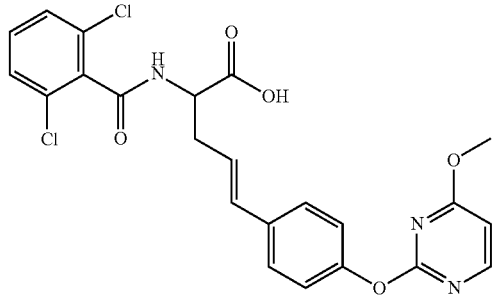 [SMILES: COc1ccnc(Oc2ccc(/C=C/CC(NC(=O)c3c(Cl)cccc3Cl)C(=O)O)cc2)n1]

In the same manner as in Example 2, (E)-2-(2,6-dichlorobenzamido)-5-[4-(4-methoxypyrimidin-2-yloxy)phenyl]pent-4-enoic acid methyl ester (30 mg) was hydrolyzed to obtain (E)-2-(2,6-dichlorobenzamido)-5-[4-(4-methoxypyrimidin-2-yloxy)phenyl]pent-4-enoic acid (28 mg).

Example 17

(E)-2-(2,6-Dichlorobenzamido)-5-[4-(4,6-dimethoxypyrimidin-2-yloxy)phenyl]pent-4-enoic acid methyl ester

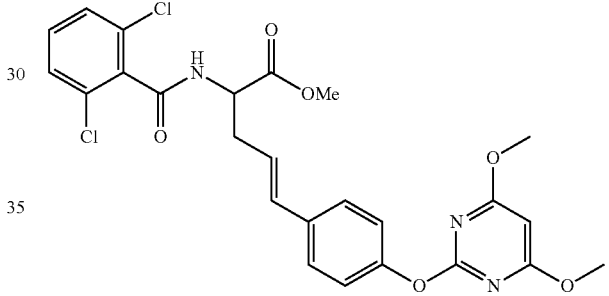

In the same manner as in Example 1,2-(2,6-dichlorobenzamido)pent-4-enoic acid methyl ester (30 mg) was reacted with 2-(4-iodophenoxy)-4,6-dimethoxypyrimidine (40 mg) to obtain (E)-2-(2,6-dichlorobenzamido)-5-[4-(4,6-dimethoxypyrimidin-2-yloxy)phenyl]pent-4-enoic acid methyl ester (30 mg). Column chromatography (silica gel, eluent: hexane/ethyl acetate=2/1) was used for purification.

Example 18

(E)-2-(2,6-Dichlorobenzamido)-5-[4-(4,6-dimethoxypyrimidin-2-yloxy)phenyl]pent-4-enoic acid

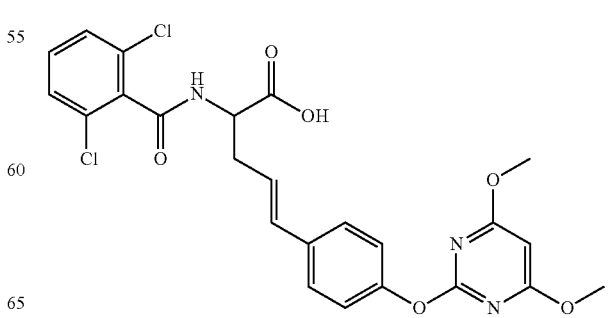

In the same manner as in Example 2, (E)-2-(2,6-dichlorobenzamido)-5-[4-(4,6-dimethoxypyrimidin-2-yloxy)phenyl]pent-4-enoic acid methyl ester (29 mg) was hydrolyzed to obtain (E)-2-(2,6-dichlorobenzamido)-5-[4-(4,6-dimethoxypyrimidin-2-yloxy)phenyl]pent-4-enoic acid (11 mg).

Example 19

(E)-2-(2,6-Dichlorobenzamido)-5-[4-(4,6-dimethylpyrimidin-2-yloxy)phenyl]pent-4-enoic acid methyl ester

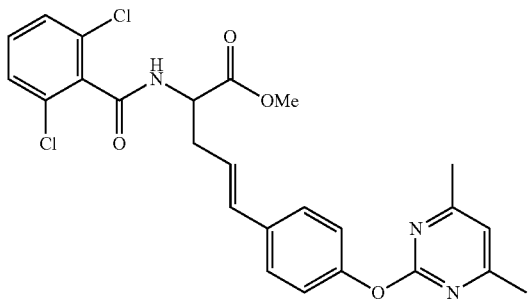 [SMILES: COC(=O)C(C/C=C/c1ccc(Oc2nc(C)cc(C)n2)cc1)NC(=O)c1c(Cl)cccc1Cl]

In the same manner as in Example 1, 2-(2,6-dichlorobenzamido)pent-4-enoic acid methyl ester (47 mg) was reacted with 2-(4-iodophenoxy)-4,6-dimethylpyrimidine (56 mg) to obtain (E)-2-(2,6-dichlorobenzamido)-5-[4-(4,6-dimethylpyrimidin-2-yloxy)phenyl]pent-4-enoic acid methyl ester (44 mg). Column chromatography (silica gel, eluent: hexane/ethyl acetate=2/1) was used for purification.

Example 20

(E)-2-(2,6-Dichlorobenzamido)-5-[4-(4,6-dimethylpyrimidin-2-yloxy)phenyl]pent-4-enoic acid

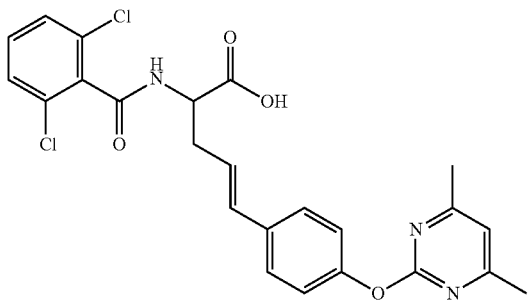 [SMILES: Cc1cc(C)nc(Oc2ccc(/C=C/CC(NC(=O)c3c(Cl)cccc3Cl)C(=O)O)cc2)n1]

In the same manner as in Example 2, (E)-2-(2,6-dichlorobenzamido)-5-[4-(4,6-dimethylpyrimidin-2-yloxy)phenyl]pent-4-enoic acid methyl ester (44 mg) was hydrolyzed to obtain (E)-2-(2,6-dichlorobenzamido)-5-[4-(4,6-dimethylpyrimidin-2-yloxy)phenyl]pent-4-enoic acid (36 mg).

Example 21

(E)-2-(2,6-Dichlorobenzamido)-5-[4-(methyl-pyrimidin-2-ylamino)phenyl]pent-4-enoic acid methyl ester

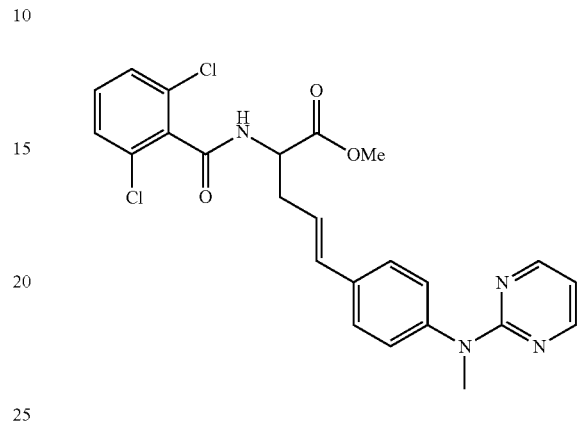

Under an argon atmosphere, palladium acetate (170.8 mg) and tris(2-methylphenyl)phosphine (222.2 mg) were added to a suspension of 2-(2,6-dichlorobenzamido)pent-4-enoic acid methyl ester (2.20 g), N-(4-iodophenyl)-N-methylpyrimidin-2-amine (2.27 g) and potassium carbonate (1.51 g) in DMF (20 ml), and the resulting mixture was stirred at 80° C. for 3 hours. After cooling the reaction solution to room temperature, ethyl acetate was added to the reaction solution, and the resulting mixture was washed twice with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=1/1→chloroform). The obtained crude product was purified again by column chromatography (silica gel, eluent: cyclohexane/ethyl acetate=4/1→2/1) to obtain (E)-2-(2,6-dichlorobenzamido)-5-[4-(methyl-pyrimidin-2-ylamino)phenyl]pent-4-enoic acid methyl ester (2.38 g).

Example 22

(E)-2-(2,6-Dichlorobenzamido)-5-[4-(methyl-pyrimidin-2-ylamino)phenyl]pent-4-enoic acid

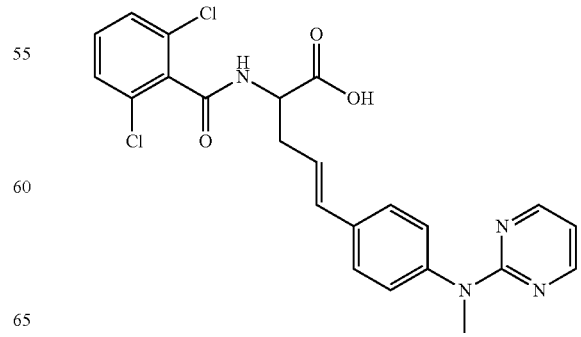

To a solution of (E)-2-(2,6-dichlorobenzamido)-5-[4-(methyl-pyrimidin-2-ylamino)phenyl]pent-4-enoic acid methyl ester (2.38 g) in THF (20 ml), 0.5N aqueous sodium hydroxide solution (14.7 ml) was added, and the resulting mixture was stirred at room temperature for 1 hour. Water (120 ml) was added to the reaction solution and the resulting mixture was washed with ether. Aqueous layer was acidified by adding 1N hydrochloric acid thereto and extracted twice with ethyl acetate. Organic layers were washed with saturated brine and dried over anhydrous sodium sulfate. After removing anhydrous sodium sulfate by filtration, the filtrate was concentrated to dryness to obtain (E)-2-(2,6-dichlorobenzamido)-5-[4-(methyl-pyrimidin-2-ylamino)phenyl]pent-4-enoic acid (2.06 g).

Example 23

(E)-2-(2,6-Dichlorobenzamido)-5-[4-(ethyl-pyrimidin-2-ylamino)phenyl]pent-4-enoic acid methyl ester

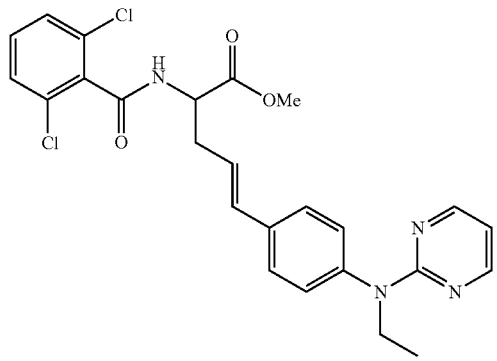 [SMILES: CCN(c1ccc(/C=C/CC(NC(=O)c2c(Cl)cccc2Cl)C(=O)OC)cc1)c1ncccn1]

In the same manner as in Example 1, 2-(2,6-dichlorobenzamido)pent-4-enoic acid methyl ester (214 mg) was reacted with N-(4-iodophenyl)-N-ethylpyrimidin-2-amine (254 mg) to obtain (E)-2-(2,6-dichlorobenzamido)-5-[4-(ethyl-pyrimidin-2-ylamino)phenyl]pent-4-enoic acid methyl ester (258 mg). Column chromatography (silica gel, eluent: hexane/ethyl acetate=4/1→hexane/ethyl acetate=2/1→hexane/ethyl acetate=1/2) was used for purification.

Example 24

(E)-2-(2,6-Dichlorobenzamido)-5-[4-(ethyl-pyrimidin-2-ylamino)phenyl]pent-4-enoic acid

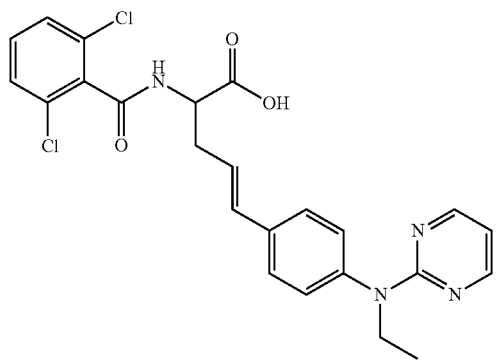 [SMILES: CCN(c1ccc(/C=C/CC(NC(=O)c2c(Cl)cccc2Cl)C(=O)O)cc1)c1ncccn1]

In the same manner as in Example 2, (E)-2-(2,6-dichlorobenzamido)-5-[4-(ethyl-pyrimidin-2-ylamino)phenyl]pent-4-enoic acid methyl ester (258 mg) was hydrolyzed to obtain (E)-2-(2,6-dichlorobenzamido)-5-[4-(ethyl-pyrimidin-2-ylamino)phenyl]pent-4-enoic acid (206 mg).

Example 25

(E)-2-(2,6-Dichlorobenzamido)-5-[4-((2-methoxyethyl)-pyrimidin-2-ylamino)phenyl]pent-4-enoic acid methyl ester

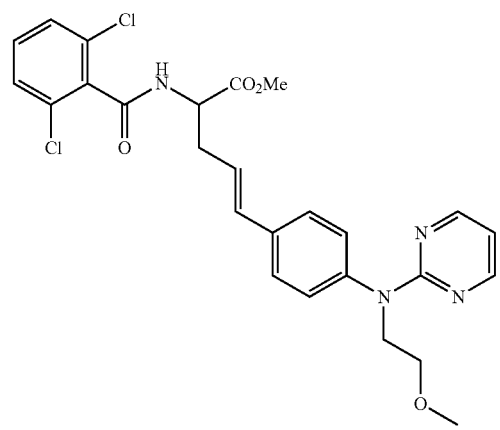 [SMILES: COCCN(c1ccc(/C=C/CC(NC(=O)c2c(Cl)cccc2Cl)C(=O)OC)cc1)c1ncccn1]

In the same manner as in Example 1, 2-(2,6-dichlorobenzamido)pent-4-enoic acid methyl ester (89 mg) was reacted with N-(4-iodophenyl)-N-(2-methoxyethyl)pyrimidin-2-amine (116 mg) to obtain (E)-2-(2,6-dichlorobenzamido)-5-[4-((2-methoxyethyl)-pyrimidin-2-ylamino)phenyl]pent-4-enoic acid methyl ester (120 mg). Column chromatography (silica gel, eluent: cyclohexane/chloroform=2/1→cyclohexane/chloroform=1/1→cyclohexane/chloroform=1/2) was used for purification.

Example 26

(E)-2-(2,6-Dichlorobenzamido)-5-[4-((2-methoxyethyl)-pyrimidin-2-ylamino)phenyl]pent-4-enoic acid sodium salt

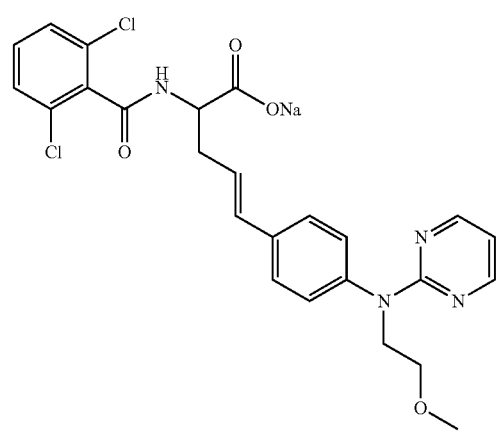

In the same manner as in Example 8, (E)-2-(2,6-dichlorobenzamido)-5-[4-((2-methoxyethyl)-pyrimidin-2-ylamino)phenyl]pent-4-enoic acid methyl ester (117 mg) was hydrolyzed to obtain (E)-2-(2,6-dichlorobenzamido)-5-[4-

((2-methoxyethyl)-pyrimidin-2-ylamino)phenyl]pent-4-enoic acid sodium salt (96 mg).

Example 27

(E)-2-(2,6-Dichlorobenzamido)-5-[4-(isopropyl-pyrimidin-2-ylamino)phenyl]pent-4-enoic acid methyl ester

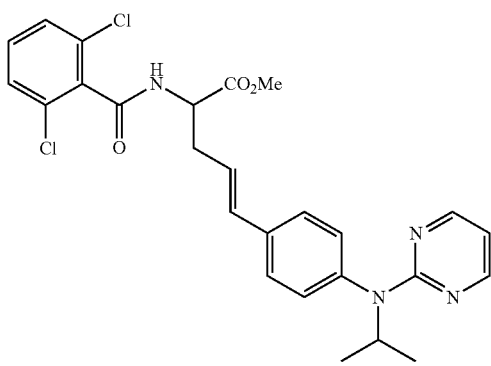 [SMILES: COC(=O)C(C/C=C/c1ccc(N(c2ncccn2)C(C)C)cc1)NC(=O)c1c(Cl)cccc1Cl]

Under an argon atmosphere, palladium acetate (316.7 mg) and tris(2-methylphenyl)phosphine (411.8 mg) were added to a suspension of 2-(2,6-dichlorobenzamido)pent-4-enoic acid methyl ester (4.09 g), N-(4-iodophenyl)-N-isopropylpyrimidin-2-amine (4.59 g) and potassium carbonate (2.80 g) in DMF (50 ml), and the resulting mixture was stirred at 80° C. for 6 hours. After cooling the reaction solution to room temperature, ethyl acetate was added thereto and the resulting mixture was washed twice with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=2/1→1/2). The obtained crude product was purified again by column chromatography (silica gel, eluent: cyclohexane/ethyl acetate=10/1→4/1) to obtain (E)-2-(2,6-dichlorobenzamido)-5-[4-(isopropyl-pyrimidin-2-ylamino)phenyl]pent-4-enoic acid methyl ester (4.65 g).

Example 28

(E)-2-(2,6-Dichlorobenzamido)-5-[4-(isopropyl-pyrimidin-2-ylamino)phenyl]pent-4-enoic acid

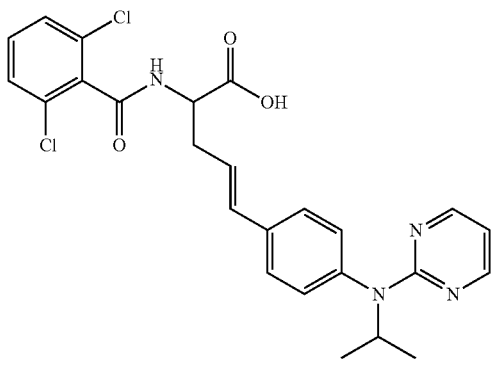 [SMILES: CC(C)N(c1ccc(/C=C/CC(NC(=O)c2c(Cl)cccc2Cl)C(=O)O)cc1)c1ncccn1]

To a solution of (E)-2-(2,6-dichlorobenzamido)-5-[4-(isopropyl-pyrimidin-2-ylamino)phenyl]pent-4-enoic acid methyl ester (5.63 g) in THF (165 ml), 0.1N aqueous sodium hydroxide solution (165 ml) was added, and the resulting mixture was stirred at room temperature for 1 hour. Water (200 ml) was added to the reaction solution and the resulting mixture was washed with ether. Aqueous layer was acidified by adding 1N hydrochloric acid thereto and extracted twice with ethyl acetate. Organic layers were washed with saturated brine and dried over anhydrous sodium sulfate. After removing anhydrous sodium sulfate by filtration, the filtrate was concentrated to dryness to obtain (E)-2-(2,6-dichlorobenzamido)-5-[4-(isopropyl-pyrimidin-2-ylamino)phenyl]pent-4-enoic acid (4.68 g).

Example 29

(E)-2-(2,6-Dichlorobenzamido)-5-[4-((4-hydroxybenzyl)-pyrimidin-2-ylamino)phenyl]pent-4-enoic acid

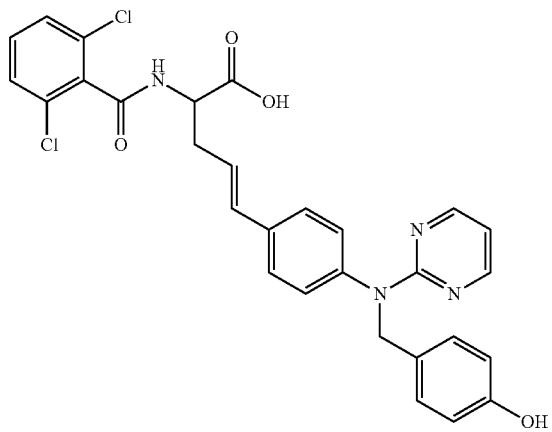 [SMILES: O=C(NC(C/C=C/c1ccc(N(Cc2ccc(O)cc2)c2ncccn2)cc1)C(=O)O)c1c(Cl)cccc1Cl]

(1) In the same manner as in Example 1,2-(2,6-dichlorobenzamido)pent-4-enoic acid methyl ester (45.6 mg) was reacted with (4-iodophenyl)-(4-acetoxybenzyl)pyrimidin-2-ylamine (67.4 mg) to obtain (E)-2-(2,6-dichlorobenzamido)-5-[4-((4-acetoxy-benzyl)-pyrimidin-2-ylamino)phenyl]pent-4-enoic acid methyl ester (61.7 mg). Column chromatography (silica gel, eluent: ethyl acetate/hexane=1/3→3/1) and thin layer chromatography (silica gel, mobile phase: cyclohexane/ethyl acetate=1/5) were used for purification.

(2) To a solution of (E)-2-(2,6-dichlorobenzamido)-5-[4-((4-acetoxy-benzyl)-pyrimidin-2-ylamino)phenyl]pent-4-enoic acid methyl ester (61.7 mg) in THF (3.0 ml), 0.1N aqueous sodium hydroxide solution (3.0 ml) was added, and the resulting mixture was stirred at room temperature for 2 hours. Water (50 ml) was added to the reaction solution and the resulting mixture was washed with ether. Aqueous layer was acidified by adding 1N hydrochloric acid thereto and extracted twice with ethyl acetate. Organic layers were washed with saturated brine and dried over anhydrous sodium sulfate. After removing anhydrous sodium sulfate by filtration, the filtrate was concentrated to dryness to obtain (E)-2-

(2,6-dichlorobenzamido)-5-[4-((4-hydroxy-benzyl)-pyrimidin-2-ylamino)phenyl]pent-4-enoic acid (43 mg).

Example 30

(E)-5-[4-((2-Cyano-ethyl)-pyrimidin-2-yl-amino)-phenyl]-2-(2,6-dichlorobenzamido)-pent-4-enoic acid methyl ester

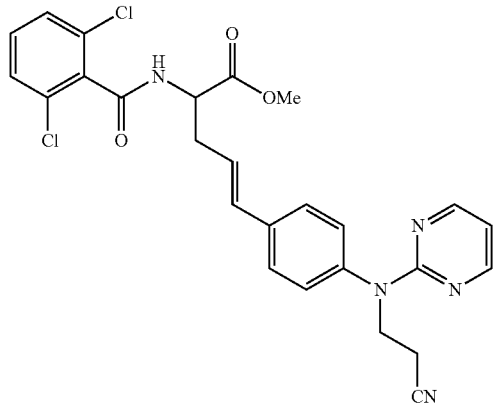

In the same manner as in Example 1,2-(2,6-dichlorobenzamido)pent-4-enoic acid methyl ester (73 mg) was reacted with 3-(N-(4-iodophenyl)-N-(pyrimidin-2-yl)amino)propanenitrile (94 mg) to obtain (E)-5-[4-((2-cyano-ethyl)-pyrimidin-2-yl-amino)-phenyl]-2-(2,6-dichlorobenzamido)-pent-4-enoic acid methyl ester (100 mg). Column chromatography (silica gel, eluent: cyclohexane/chloroform=2/1-1/2-1/5) was used for purification.

Example 31

(E)-5-[4-((2-Cyano-ethyl)-pyrimidin-2-yl-amino)-phenyl]-2-(2,6-dichlorobenzamido)-pent-4-enoic acid sodium salt

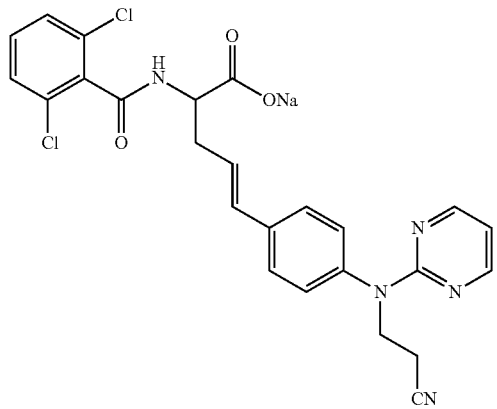

In the same manner as in Example 8, (E)-5-[4-((2-cyano-ethyl)-pyrimidin-2-yl-amino)-phenyl]-2-(2,6-dichlorobenzamido)-pent-4-enoic acid methyl ester (90 mg) was hydrolyzed to obtain (E)-5-[4-((2-cyano-ethyl)-pyrimidin-2-yl-amino)-phenyl]-2-(2,6-dichlorobenzamido)-pent-4-enoic acid sodium salt (68 mg).

Example 32

(E)-5-[4-(Benzyl-pyrimidin-2-yl-amino)-phenyl]-2-(2,6-dichlorobenzamido)-pent-4-enoic acid methyl ester

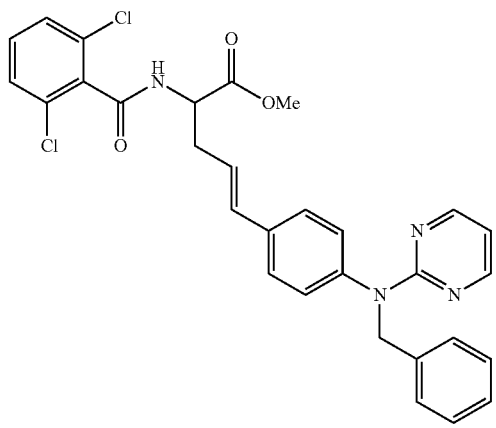 [SMILES: COC(=O)C(C/C=C/c1ccc(N(Cc2ccccc2)c2ncccn2)cc1)NC(=O)c1c(Cl)cccc1Cl]

In the same manner as in Example 1,2-(2,6-dichlorobenzamido)pent-4-enoic acid methyl ester (59.3 mg) was reacted with N-benzyl-N-(4-iodophenyl)pyrimidin-2-amine (67.0 mg) to obtain (E)-5-[4-(benzyl-pyrimidin-2-yl-amino)-phenyl]-2-(2,6-dichlorobenzamido)-pent-4-enoic acid methyl ester (58.7 mg). Column chromatography (silica gel, eluent: chloroform/cyclohexane=2/1→chloroform) and thin layer chromatography (silica gel, mobile phase: cyclohexane/ethyl acetate=2/1) were used for purification.

Example 33

(E)-5-[4-(Benzyl-pyrimidin-2-yl-amino)-phenyl]-2-(2,6-dichlorobenzamido)-pent-4-enoic acid sodium salt

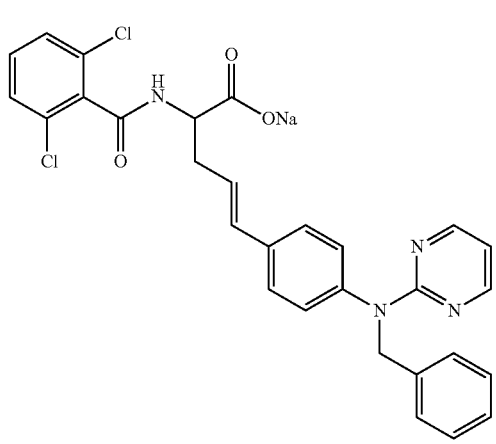

In the same manner as in Example 8, (E)-5-[4-(benzyl-pyrimidin-2-yl-amino)-phenyl]-2-(2,6-dichlorobenzamido)- pent-4-enoic acid methyl ester (58.7 mg) was hydrolyzed to obtain (E)-5-[4-(benzyl-pyrimidin-2-yl-amino)-phenyl]-2-(2,6-dichlorobenzamido)-pent-4-enoic acid sodium salt (33.5 mg).

Example 34

(E)-2-(2,6-Dichlorobenzamido)-5-[4-((4-methoxy-benzyl)-pyrimidin-2-ylamino)phenyl]pent-4-enoic acid methyl ester

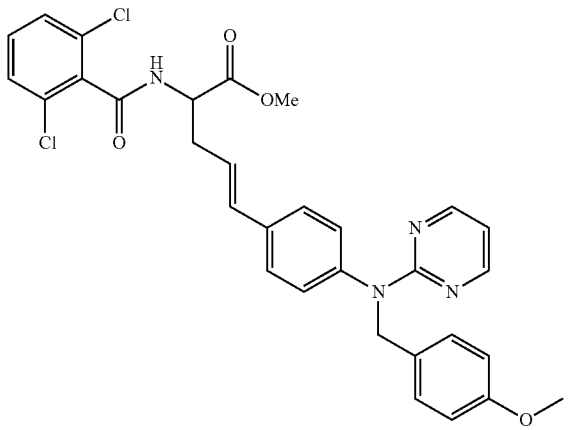

In the same manner as in Example 1,2-(2,6-dichlorobenzamido)pent-4-enoic acid methyl ester (83.3 mg) was reacted with N-(4-methoxybenzyl)-N-(4-bromophenyl)pyrimidin-2-amine (102.4 mg) to obtain (E)-2-(2,6-dichlorobenzamido)-5-[4-((4-methoxy-benzyl)-pyrimidin-2-ylamino)phenyl]pent-4-enoic acid methyl ester (102.4 mg). Column chromatography (silica gel, eluent: hexane/ethyl acetate=3/1→1/3) and thin layer chromatography (silica gel, mobile phase: cyclohexane/ethyl acetate=1/5) were used for purification.

Example 35

(E)-2-(2,6-Dichlorobenzamido)-5-[4-((4-methoxy-benzyl)-pyrimidin-2-ylamino)phenyl]pent-4-enoic acid sodium salt

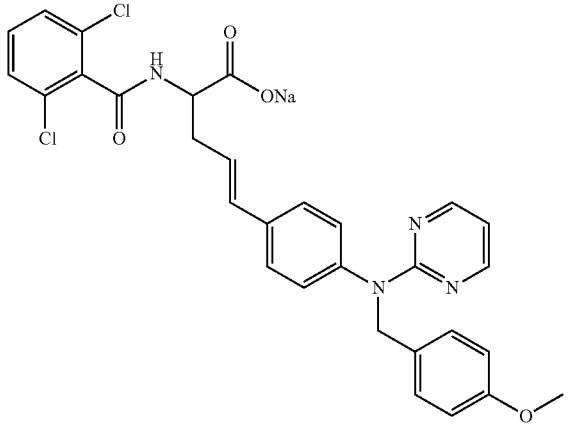

In the same manner as in Example 8, (E)-2-(2,6-dichlorobenzamido)-5-[4-((4-methoxy-benzyl)-pyrimidin-2-ylamino)phenyl]pent-4-enoic acid methyl ester (102.4 mg) was hydrolyzed to obtain (E)-2-(2,6-dichlorobenzamido)-5-[4-((4-methoxy-benzyl)-pyrimidin-2-ylamino)phenyl]pent-4-enoic acid sodium salt (76.4 mg).

Example 36

(E)-5-(4-Butyl-pyrimidin-2-yl-amino)-phenyl]-2-(2,6-dichlorobenzamido)-pent-4-enoic acid methyl ester

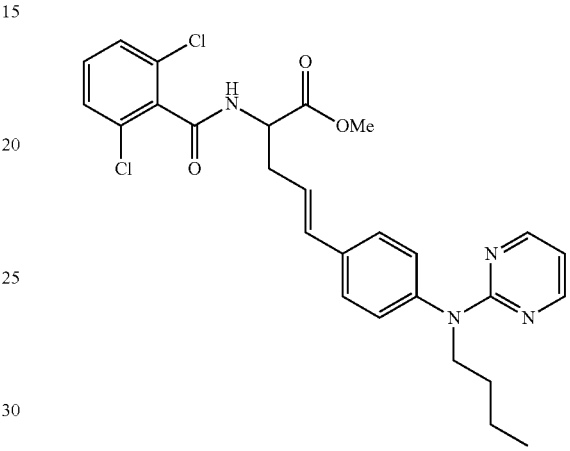

In the same manner as in Example 1,2-(2,6-dichlorobenzamido)pent-4-enoic acid methyl ester (90.4 mg) was reacted with N-(4-bromophenyl)-N-butylpyrimidin-2-amine (92.0 mg) to obtain (E)-5-(4-butyl-pyrimidin-2-yl-amino)-phenyl]-2-(2,6-dichlorobenzamido)-pent-4-enoic acid methyl ester (78.8 mg). Column chromatography (silica gel, eluent: chloroform/cyclohexane=2/1→chloroform) and thin layer chromatography (silica gel, mobile phase: cyclohexane/ethyl acetate=2/1) were used for purification.

Example 37

(E)-5-(4-Butyl-pyrimidin-2-yl-amino)-phenyl]-2-(2,6-dichlorobenzamido)-pent-4-enoic acid sodium salt

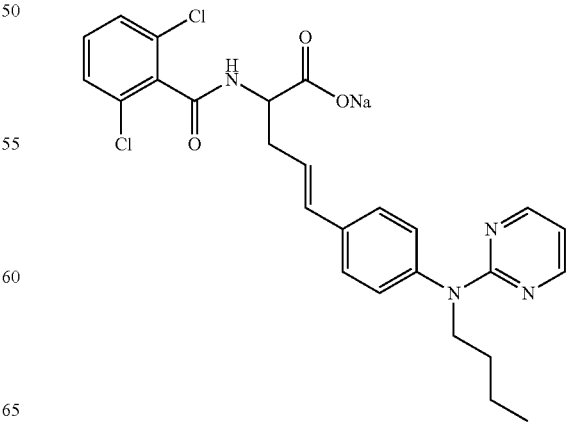

In the same manner as in Example 8, (E)-5-(4-butyl-pyrimidin-2-yl-amino)-phenyl]-2-(2,6-dichlorobenzamido)-pent-4-enoic acid methyl ester (78.8 mg) was hydrolyzed to obtain (E)-5-(4-butyl-pyrimidin-2-yl-amino)-phenyl]-2-(2,6-dichlorobenzamido)-pent-4-enoic acid sodium salt (42.0 mg).

Example 38

(E)-2-(2,6-Dichlorobenzamido)-5-[4-(pyridin-3-ylmethyl-pyrimidin-2-ylamino)phenyl]pent-4-enoic acid methyl ester

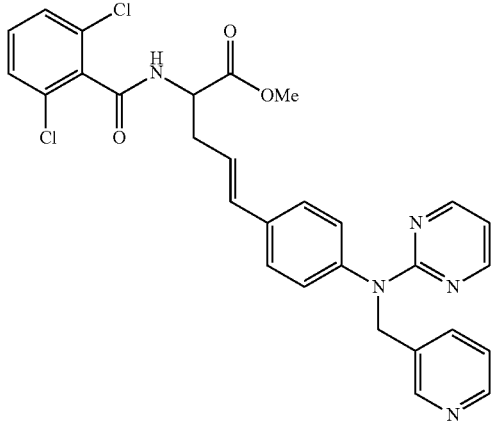 [SMILES: COC(=O)C(C/C=C/c1ccc(N(Cc2cccnc2)c2ncccn2)cc1)NC(=O)c1c(Cl)cccc1Cl]

In the same manner as in Example 1,2-(2,6-dichlorobenzamido)pent-4-enoic acid methyl ester (1060.0 mg) was reacted with N-(4-bromophenyl)-N-((pyridin-3-yl)methyl)pyrimidin-2-amine (120.0 mg) to obtain (E)-2-(2,6-dichlorobenzamido)-5-[4-(pyridin-3-ylmethyl-pyrimidin-2-ylamino)phenyl]pent-4-enoic acid methyl ester (147.8 mg). Column chromatography (silica gel, eluent: chloroform→chloroform/ethyl acetate=1/1) and thin layer chromatography (chloroform/ethyl acetate=1/1) were used for purification.

Example 39

(E)-2-(2,6-Dichlorobenzamido)-5-[4-(pyridin-3-ylmethyl-pyrimidin-2-ylamino)phenyl]pent-4-enoic acid sodium salt

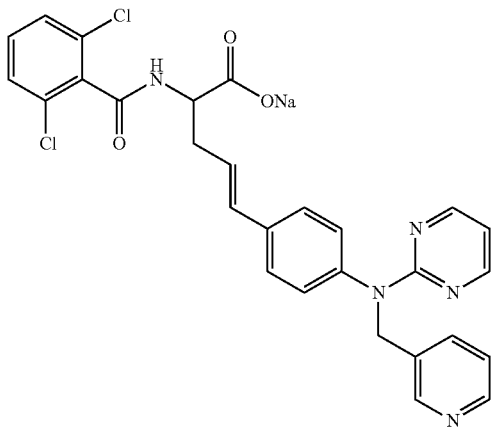

In the same manner as in Example 8, (E)-2-(2,6-dichlorobenzamido)-5-[4-(pyridin-3-ylmethyl-pyrimidin-2-ylamino)phenyl]pent-4-enoic acid methyl ester (147.8 mg) was hydrolyzed to obtain (E)-2-(2,6-dichlorobenzamido)-5-[4-(pyridin-3-ylmethyl-pyrimidin-2-ylamino)phenyl]pent-4-enoic acid sodium salt (114.4 mg).

Example 40

(E)-2-(2,6-Dichlorobenzamido)-5-[4-(pyrimidin-2-yl-thiazol-4-ylmethyl-amino)phenyl]pent-4-enoic acid methyl ester

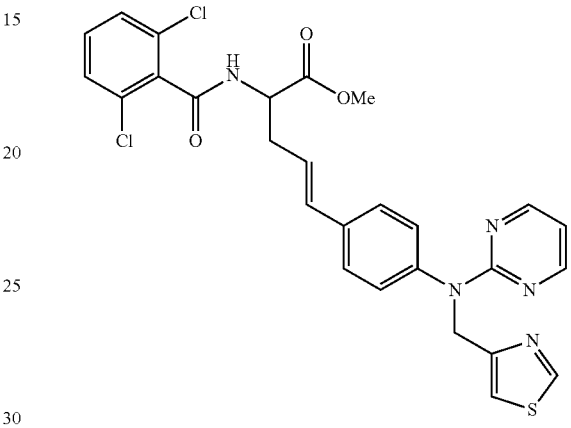

In the same manner as in Example 1,2-(2,6-dichlorobenzamido)pent-4-enoic acid methyl ester (78.0 mg) was reacted with N-(4-bromophenyl)-N-((thiazol-4-yl)methyl)pyrimidin-2-amine (90.0 mg) to obtain (E)-2-(2,6-dichlorobenzamido)-5-[4-(pyrimidin-2-yl-thiazol-4-ylmethyl-amino)phenyl]pent-4-enoic acid methyl ester (87.7 mg). Column chromatography (silica gel, eluent: chloroform→chloroform/ethyl acetate=3/1) and thin layer chromatography (cyclohexane/ethyl acetate=1/2) were used for purification.

Example 41

(E)-2-(2,6-Dichlorobenzamido)-5-[4-(pyrimidin-2-yl-thiazol-4-ylmethyl-amino)phenyl]pent-4-enoic acid sodium salt

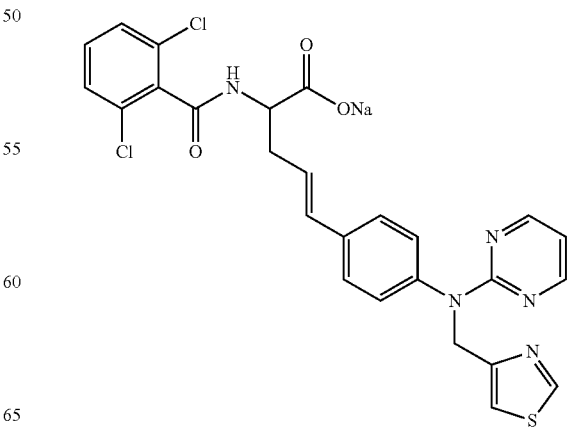

In the same manner as in Example 8, (E)-2-(2,6-dichlorobenzamido)-5-[4-(pyrimidin-2-yl-thiazol-4-ylmethyl-amino)phenyl]pent-4-enoic acid methyl ester (87.7 mg) was hydrolyzed to obtain (E)-2-(2,6-dichlorobenzamido)-5-[4-(pyrimidin-2-yl-thiazol-4-ylmethyl-amino)phenyl]pent-4-enoic acid sodium salt (63.6 mg).

Example 42

(E)-2-(2,6-Dichlorobenzamido)-5-[4-((4-methoxy-pyrimidin-2-yl)-methyl-amino)phenyl]pent-4-enoic acid methyl ester

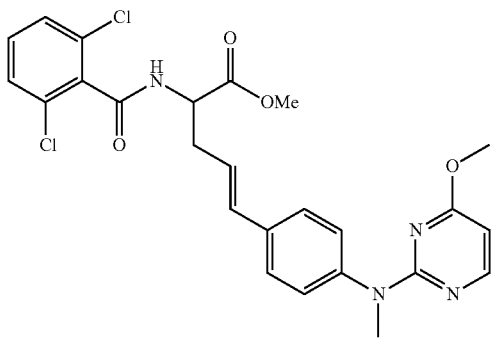 [SMILES: COC(=O)C(C/C=C/c1ccc(N(C)c2nccc(OC)n2)cc1)NC(=O)c1c(Cl)cccc1Cl]

In the same manner as in Example 1, 2-(2,6-dichlorobenzamido)pent-4-enoic acid methyl ester (43 mg) was reacted with N-(4-iodophenyl)-4-methoxy-N-methylpyrimidin-2-amine (51 mg) to obtain (E)-2-(2,6-dichlorobenzamido)-5-[4-((4-methoxy-pyrimidin-2-yl)-methyl-amino)phenyl]pent-4-enoic acid methyl ester (32 mg). Column chromatography (silica gel, eluent: hexane/ethyl acetate=2/1) was used for purification.

Example 43

(E)-2-(2,6-Dichlorobenzamido)-5-[4-((4-methoxy-pyrimidin-2-yl)-methyl-amino)phenyl]pent-4-enoic acid

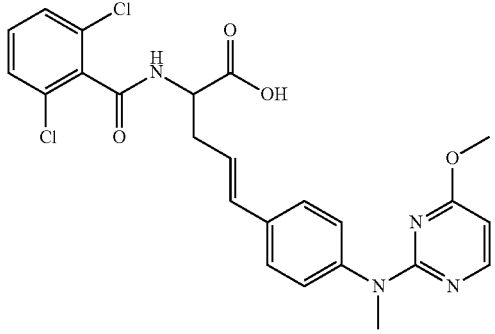 [SMILES: COc1ccnc(N(C)c2ccc(/C=C/CC(NC(=O)c3c(Cl)cccc3Cl)C(=O)O)cc2)n1]

In the same manner as in Example 2, (E)-2-(2,6-dichlorobenzamido)-5-[4-((4-methoxy-pyrimidin-2-yl)-methyl-amino)phenyl]pent-4-enoic acid methyl ester (31 mg) was hydrolyzed to obtain (E)-2-(2,6-dichlorobenzamido)-5-[4-((4-methoxy-pyrimidin-2-yl)-methyl-amino)phenyl]pent-4-enoic acid (29 mg).

Example 44

(E)-2-(2,6-Dichlorobenzamido)-5-[4-((4,6-dimethoxy-pyrimidin-2-yl)-methyl-amino)phenyl]pent-4-enoic acid methyl ester

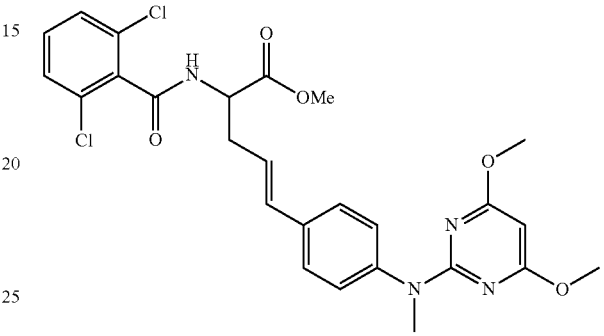

In the same manner as in Example 1, 2-(2,6-dichlorobenzamido)pent-4-enoic acid methyl ester (80 mg) was reacted with N-(4-iodophenyl)-4,6-dimethoxy-N-methylpyrimidin-2-amine (118 mg) to obtain (E)-2-(2,6-dichlorobenzamido)-5-[4-((4,6-dimethoxy-pyrimidin-2-yl)-methyl-amino)phenyl]pent-4-enoic acid methyl ester (92 mg). Column chromatography (silica gel, eluent: hexane/ethyl acetate=2/1) was used for purification.

Example 45

(E)-2-(2,6-Dichlorobenzamido)-5-[4-((4,6-dimethoxy-pyrimidin-2-yl)-methyl-amino)phenyl]pent-4-enoic acid

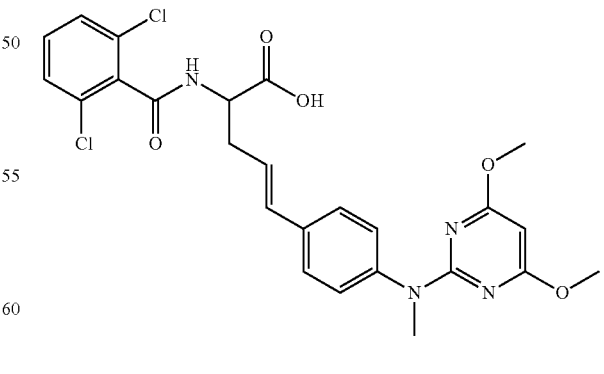

In the same manner as in Example 2, (E)-2-(2,6-dichlorobenzamido)-5-[4-((4,6-dimethoxy-pyrimidin-2-yl)-methyl-amino)phenyl]pent-4-enoic acid methyl ester (91 mg)

was hydrolyzed to obtain (E)-2-(2,6-dichlorobenzamido)-5-[4-((4,6-dimethoxy-pyrimidin-2-yl)-methyl-amino)phenyl]pent-4-enoic acid (76 mg).

Example 46

(E)-2-(2,6-Dichlorobenzamido)-5-[4-(phenyl-pyrimidin-2-ylamino)phenyl]pent-4-enoic acid methyl ester

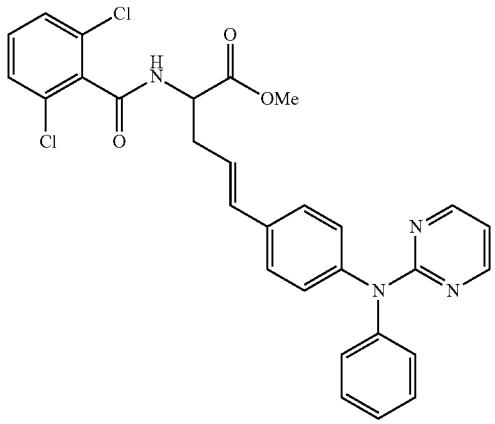

In the same manner as in Example 1,2-(2,6-dichlorobenzamido)pent-4-enoic acid methyl ester (52.4 mg) was reacted with N-(4-bromophenyl)-N-phenylpyrimidin-2-amine (56.6 mg) to obtain (E)-2-(2,6-dichlorobenzamido)-5-[4-(phenyl-pyrimidin-2-ylamino)phenyl]pent-4-enoic acid methyl ester (40.0 mg). Column chromatography (silica gel, eluent: chloroform/cyclohexane=1/1→chloroform) and thin layer chromatography (silica gel, mobile phase: cyclohexane/ethyl acetate=1/2) were used for purification.

Example 47

(E)-2-(2,6-Dichlorobenzamido)-5-[4-(phenyl-pyrimidin-2-ylamino)phenyl]pent-4-enoic acid sodium salt

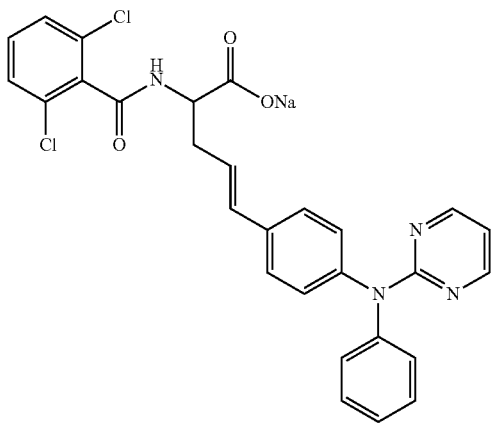

In the same manner as in Example 8, (E)-2-(2,6-dichlorobenzamido)-5-[4-(phenyl-pyrimidin-2-ylamino)phenyl]pent-4-enoic acid methyl ester (40.0 mg) was hydrolyzed to obtain (E)-2-(2,6-dichlorobenzamido)-5-[4-(phenyl-pyrimidin-2-ylamino)phenyl]pent-4-enoic acid sodium salt (25.3 mg).

Example 48

(E)-2-(2,6-Dichlorobenzamido)-5-[4-(pyrimidin-2-yl-(tetrahydro-pyran-4-yl)-amino)phenyl]pent-4-enoic acid methyl ester

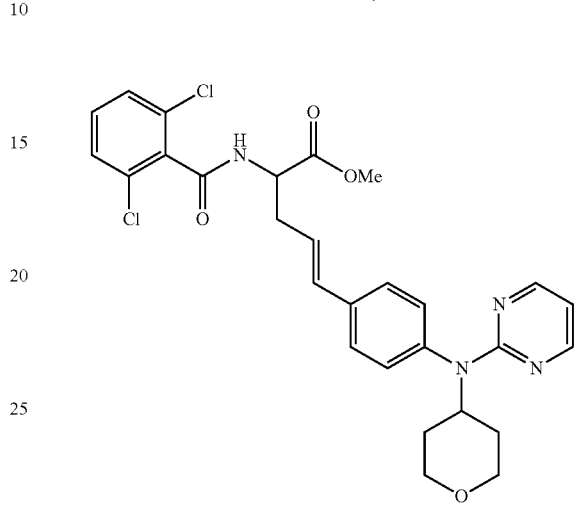

In the same manner as in Example 1,2-(2,6-dichlorobenzamido)pent-4-enoic acid methyl ester (164.0 mg) was reacted with trifluoromethanesulfonic acid 4-[pyrimidin-2-yl-(tetrahydropyran-4-yl)amino]phenyl ester (220.0 mg) to obtain (E)-2-(2,6-dichlorobenzamido)-5-[4-(pyrimidin-2-yl-(tetrahydro-pyran-4-yl)-amino)phenyl]pent-4-enoic acid methyl ester (178.5 mg). Column chromatography (silica gel, eluent: chloroform/cyclohexane=1/2→chloroform) and thin layer chromatography (silica gel, mobile phase: cyclohexane/ethyl acetate=1/1) were used for purification.

Example 49

(E)-2-(2,6-Dichlorobenzamido)-5-[4-(pyrimidin-2-yl-(tetrahydro-pyran-4-yl)-amino)phenyl]pent-4-enoic acid sodium salt

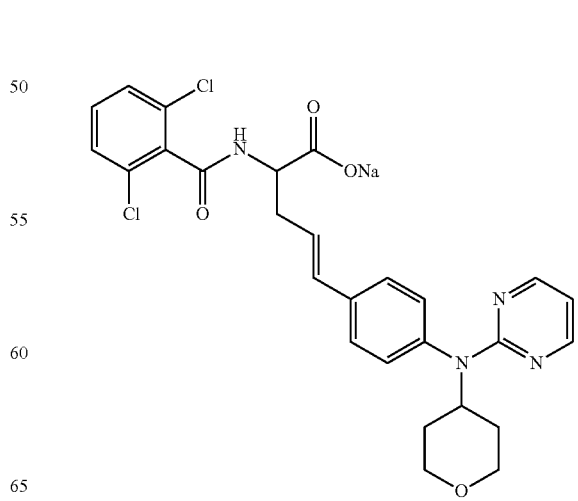

In the same manner as in Example 8, (E)-2-(2,6-dichlorobenzamido)-5-[4-(pyrimidin-2-yl-(tetrahydro-pyran-4-yl)-amino)phenyl]pent-4-enoic acid methyl ester (178.5 mg) was hydrolyzed to obtain (E)-2-(2,6-dichlorobenzamido)-5-[4-(pyrimidin-2-yl-(tetrahydro-pyran-4-yl)-amino)phenyl]pent-4-enoic acid sodium salt (103 mg).

Example 50

(E)-2-(2,6-Dichlorobenzamido)-5-[4-((3-methyl-2-butenyl)-pyrimidin-2-ylamino)phenyl]pent-4-enoic acid methyl ester

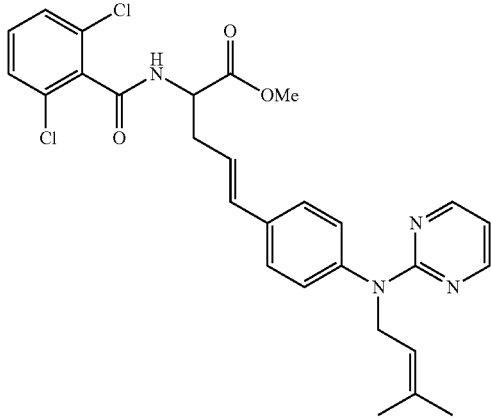

In the same manner as in Example 1,2-(2,6-dichlorobenzamido)pent-4-enoic acid methyl ester (145 mg) was reacted with N-(4-iodophenyl)-N-(3-methyl-2-butenyl)pyrimidin-2-amine (175 mg) to obtain (E)-2-(2,6-dichlorobenzamido)-5-[4-((3-methyl-2-butenyl)-pyrimidin-2-ylamino)phenyl]pent-4-enoic acid methyl ester (133 mg). Column chromatography (silica gel, eluent: hexane/ethyl acetate=1/1) was used for purification.

Example 51

(E)-2-(2,6-Dichlorobenzamido)-5-[4-((3-methyl-2-butenyl)-pyrimidin-2-ylamino)phenyl]pent-4-enoic acid sodium salt

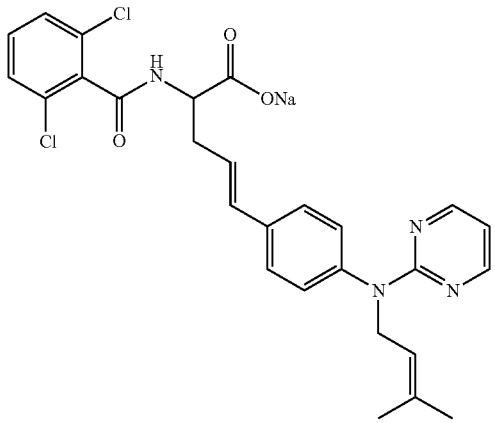

In the same manner as in Example 8, (E)-2-(2,6-dichlorobenzamido)-5-[4-((3-methyl-2-butenyl)-pyrimidin-2-ylamino)phenyl]pent-4-enoic acid methyl ester (133 mg) was hydrolyzed to obtain (E)-2-(2,6-dichlorobenzamido)-5-[4-((3-methyl-2-butenyl)-pyrimidin-2-ylamino)phenyl]pent-4-enoic acid sodium salt (95 mg).

Example 52

(E)-5-[4-(Cyclopropylmethyl-pyrimidin-2-ylamino)phenyl]-2-(2,6-dichlorobenzamido)pent-4-enoic acid methyl ester

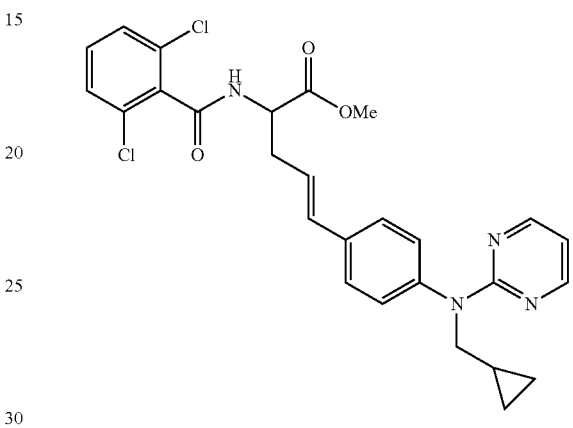

In the same manner as in Example 1,2-(2,6-dichlorobenzamido)pent-4-enoic acid methyl ester (139 mg) was reacted with N-(cyclopropylmethyl)-N-(4-iodophenyl)pyrimidin-2-amine (162 mg) to obtain (E)-5-[4-(cyclopropylmethyl-pyrimidin-2-ylamino)phenyl]-2-(2,6-dichlorobenzamido)pent-4-enoic acid methyl ester (167 mg). Column chromatography (silica gel, eluent: hexane/ethyl acetate=1/1) was used for purification.

Example 53

(E)-5-[4-(Cyclopropylmethyl-pyrimidin-2-ylamino)phenyl]-2-(2,6-dichlorobenzamido)pent-4-enoic acid sodium salt

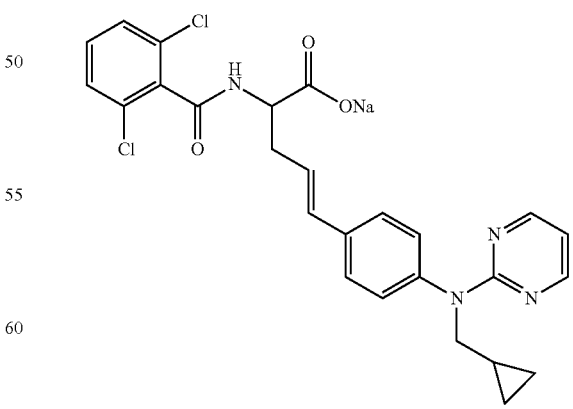

In the same manner as in Example 8, (E)-5-[4-(cyclopropylmethyl-pyrimidin-2-ylamino)phenyl]-2-(2,6-dichlorobenzamido)pent-4-enoic acid methyl ester (153 mg) was hydrolyzed to obtain (E)-5-[4-(cyclopropylmethyl-pyrimidin-2-ylamino)phenyl]-2-(2,6-dichlorobenzamido)pent-4-enoic acid sodium salt (101 mg).

Example 54

(E)-2-(2,6-Dichlorobenzamido)-5-[4-(isobutyl-pyrimidin-2-ylamino)phenyl]pent-4-enoic acid methyl ester

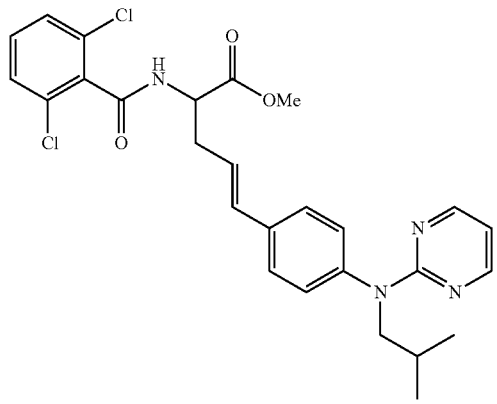 [SMILES: COC(=O)C(C/C=C/c1ccc(N(CC(C)C)c2ncccn2)cc1)NC(=O)c1c(Cl)cccc1Cl]

In the same manner as in Example 1,2-(2,6-dichlorobenzamido)pent-4-enoic acid methyl ester (143 mg) was reacted with N-(4-iodophenyl)-N-isobutylpyrimidin-2-amine (167 mg) to obtain (E)-2-(2,6-dichlorobenzamido)-5-[4-(isobutyl-pyrimidin-2-ylamino)phenyl]pent-4-enoic acid methyl ester (159 mg). Column chromatography (silica gel, eluent: hexane/ethyl acetate=1/1) was used for purification.

Example 55

(E)-2-(2,6-Dichlorobenzamido)-5-[4-(isobutyl-pyrimidin-2-ylamino)phenyl]pent-4-enoic acid sodium salt

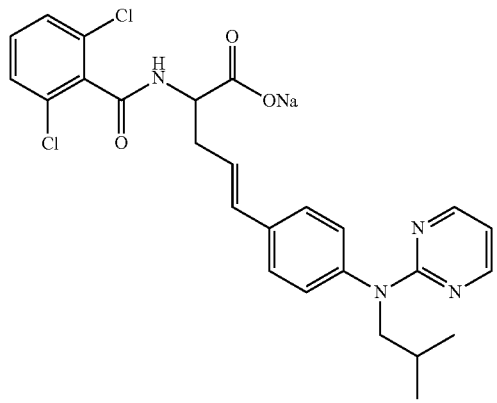

In the same manner as in Example 8, (E)-2-(2,6-dichlorobenzamido)-5-[4-(isobutyl-pyrimidin-2-ylamino)phenyl]pent-4-enoic acid methyl ester (157 mg) was hydrolyzed to obtain (E)-2-(2,6-dichlorobenzamido)-5-[4-(isobutyl-pyrimidin-2-ylamino)phenyl]pent-4-enoic acid sodium salt (128 mg).

Example 56

(E)-2-(2,6-Dichlorobenzamido)-5-[4-(propyl-pyrimidin-2-ylamino)phenyl]pent-4-enoic acid methyl ester

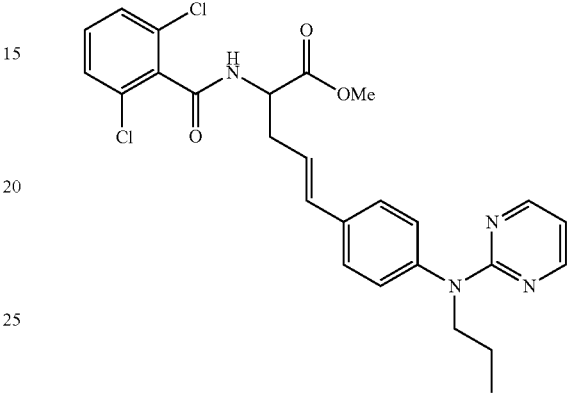

In the same manner as in Example 1,2-(2,6-dichlorobenzamido)pent-4-enoic acid methyl ester (171 mg) was reacted with N-(4-iodophenyl)-N-propylpyrimidin-2-amine (192 mg) to obtain (E)-2-(2,6-dichlorobenzamido)-5-[4-(propyl-pyrimidin-2-ylamino)phenyl]pent-4-enoic acid methyl ester (209 mg). Column chromatography (silica gel, eluent: cyclohexane/chloroform=4/1→3/1) was used for purification.

Example 57

(E)-2-(2,6-Dichlorobenzamido)-5-[4-(propyl-pyrimidin-2-ylamino)phenyl]pent-4-enoic acid

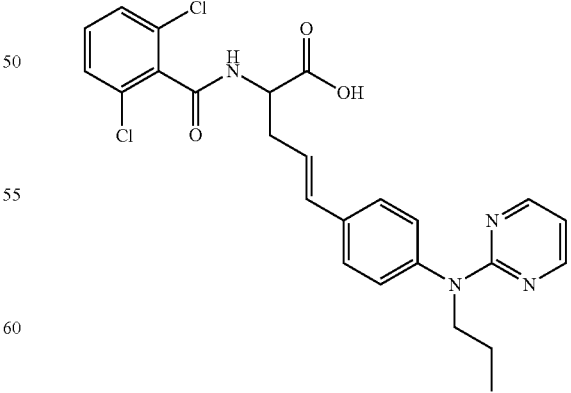

In the same manner as in Example 2, (E)-2-(2,6-dichlorobenzamido)-5-[4-(propyl-pyrimidin-2-ylamino)phenyl]pent-4-enoic acid methyl ester (127 mg) was hydrolyzed to obtain (E)-2-(2,6-dichlorobenzamido)-5-[4-(propyl-pyrimidin-2-ylamino)phenyl]pent-4-enoic acid (95 mg).

Example 58

(E)-2-(2,6-Dichlorobenzamido)-5-[4-(pyridin-4-ylmethyl-pyrimidin-2-ylamino)phenyl]pent-4-enoic acid methyl ester

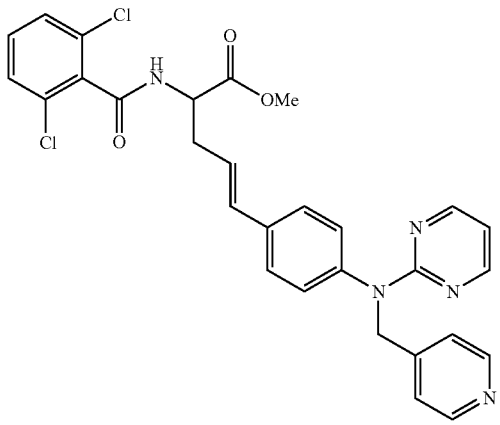 [SMILES: O=C(NC(C/C=C/c1ccc(N(Cc2ccncc2)c2ncccn2)cc1)C(=O)O)c1c(Cl)cccc1Cl]

In the same manner as in Example 1,2-(2,6-dichlorobenzamido)pent-4-enoic acid methyl ester (72 mg) was reacted with N-(4-iodophenyl)-N-((pyridin-4-yl)methyl)pyrimidin-2-amine (93 mg) to obtain (E)-2-(2,6-dichlorobenzamido)-5-[4-(pyridin-4-ylmethyl-pyrimidin-2-ylamino)phenyl]pent-4-enoic acid methyl ester (99 mg). Column chromatography (silica gel, eluent: cyclohexane/ethyl acetate=1/2→1/3) was used for purification.

Example 59

(E)-2-(2,6-Dichlorobenzamido)-5-[4-(pyridin-4-ylmethyl-pyrimidin-2-ylamino)phenyl]pent-4-enoic acid

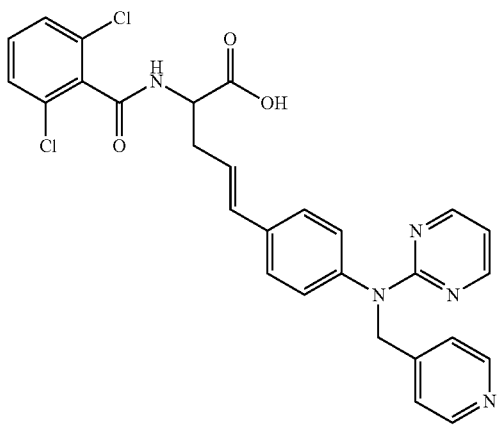

In the same manner as in Example 2, (E)-2-(2,6-dichlorobenzamido)-5-[4-(pyridin-4-ylmethyl-pyrimidin-2-ylamino)phenyl]pent-4-enoic acid methyl ester (99 mg) was hydrolyzed to obtain (E)-2-(2,6-dichlorobenzamido)-5-[4-(pyridin-4-ylmethyl-pyrimidin-2-ylamino)phenyl]pent-4-enoic acid (48 mg).

Example 60

(E)-2-(2,6-Dichlorobenzamido)-5-[4-(pyridin-2-ylmethyl-pyrimidin-2-ylamino)phenyl]pent-4-enoic acid methyl ester

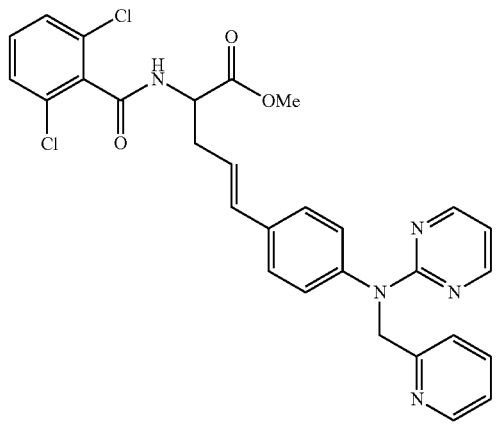

In the same manner as in Example 1,2-(2,6-dichlorobenzamido)pent-4-enoic acid methyl ester (124 mg) was reacted with N-(4-iodophenyl)-N-((pyridin-2-yl)methyl)pyrimidin-2-amine (159 mg) to obtain (E)-2-(2,6-dichlorobenzamido)-5-[4-(pyridin-2-ylmethyl-pyrimidin-2-ylamino)phenyl]pent-4-enoic acid methyl ester (208 mg). Column chromatography (silica gel, eluent: cyclohexane/ethyl acetate=1/1→1/2) was used for purification.

Example 61

(E)-2-(2,6-Dichlorobenzamido)-5-[4-(pyridin-2-ylmethyl-pyrimidin-2-ylamino)phenyl]pent-4-enoic acid

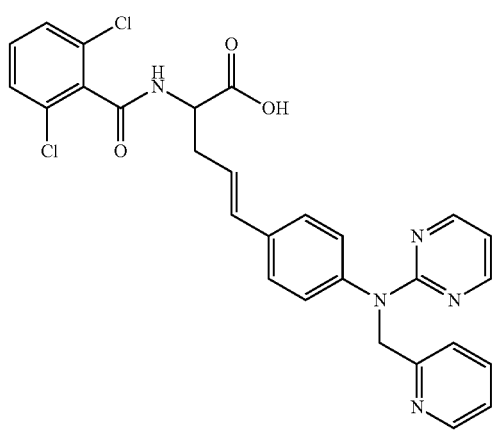 [SMILES: O=C(NC(C/C=C/c1ccc(N(Cc2ccccn2)c2ncccn2)cc1)C(=O)O)c1c(Cl)cccc1Cl]

In the same manner as in Example 2, (E)-2-(2,6-dichlorobenzamido)-5-[4-(pyridin-2-ylmethyl-pyrimidin-2-ylamino)phenyl]pent-4-enoic acid methyl ester (208 mg) was hydrolyzed to obtain (E)-2-(2,6-dichlorobenzamido)-5-[4-(pyridin-2-ylmethyl-pyrimidin-2-ylamino)phenyl]pent-4-enoic acid (123 mg).

Example 62

(E)-2-(2,6-Difluorobenzamido)-5-[4-(methyl-pyrimidin-2-ylamino)phenyl]pent-4-enoic acid methyl ester

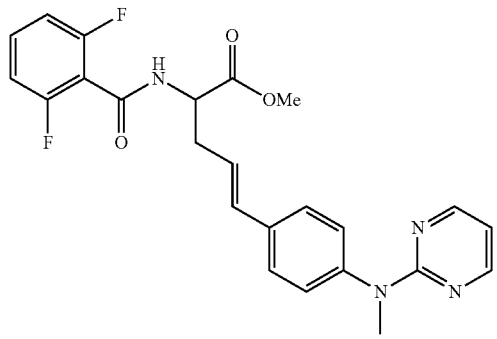 [SMILES: COC(=O)C(C/C=C/c1ccc(N(C)c2ncccn2)cc1)NC(=O)c1c(F)cccc1F]

Under an argon atmosphere, triethylamine (0.028 ml) and 2,6-difluorobenzoyl chloride (0.015 ml) were added to a solution of 2-amino-5-[4-(methyl-pyrimidin-2-ylamino)phenyl]pent-4-enoic acid methyl ester (31.7 mg) in dichloromethane (2 ml), and the resulting mixture was stirred at room temperature for 2 hours. Saturated aqueous sodium hydrogen carbonate solution was added to the reaction solution and the resulting mixture was extracted with ethyl acetate. Organic layer was washed twice with water and once with saturated brine, and dried over anhydrous sodium sulfate. After removing anhydrous sodium sulfate by filtration, the filtrate was concentrated. The residue was purified by thin layer chromatography (silica gel, mobile phase: cyclohexane/ethyl acetate=3/2) to obtain (E)-2-(2,6-difluorobenzamido)-5-[4-(methyl-pyrimidin-2-ylamino)phenyl]pent-4-enoic acid methyl ester (42 mg).

Example 63

(E)-2-(2,6-Difluorobenzamido)-5-[4-(methyl-pyrimidin-2-ylamino)phenyl]pent-4-enoic acid

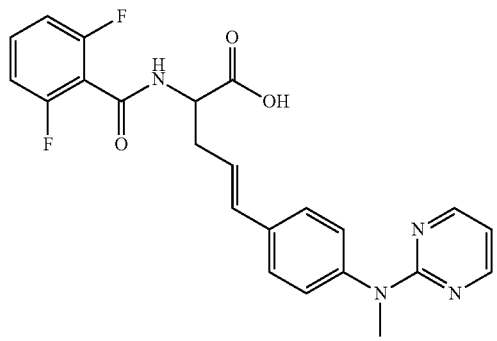 [SMILES: CN(c1ccc(/C=C/CC(NC(=O)c2c(F)cccc2F)C(=O)O)cc1)c1ncccn1]

In the same manner as in Example 2, (E)-2-(2,6-difluorobenzamido)-5-[4-(methyl-pyrimidin-2-ylamino)phenyl]pent-4-enoic acid methyl ester (42 mg) was hydrolyzed to obtain (E)-2-(2,6-difluorobenzamido)-5-[4-(methyl-pyrimidin-2-ylamino)phenyl]pent-4-enoic acid (29 mg).

Example 64

(E)-2-(2-Chloro-6-fluorobenzamido)-5-[4-(methyl-pyrimidin-2-ylamino)phenyl]pent-4-enoic acid methyl ester

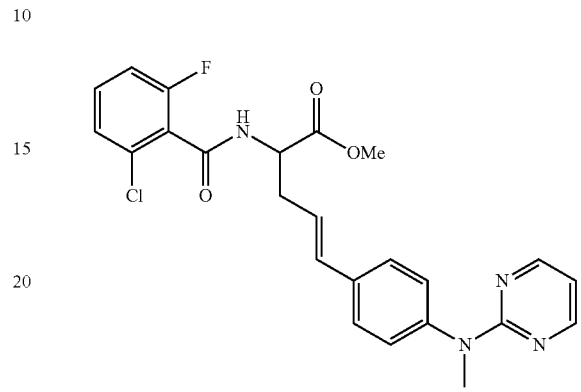

Under an argon atmosphere, EDC hydrochloride (39 mg) and HOBT (3 mg) were added to a solution of 2-amino-5-[4-(methyl-pyrimidin-2-ylamino)phenyl]pent-4-enoic acid methyl ester (51 mg) and 2-chloro-6-fluorobenzoic acid in dichloromethane (1.5 ml), and the resulting mixture was stirred at room temperature for 28 hours. To the reaction solution, 1N hydrochloric acid was added, and the resulting mixture was extracted with ethyl acetate. Organic layer was washed with saturated aqueous sodium hydrogen carbonate solution and dried over anhydrous sodium sulfate. After removing anhydrous sodium sulfate by filtration, the filtrate was concentrated. The residue was purified by thin layer chromatography (silica gel, mobile phase: hexane/ethyl acetate=1/2) to obtain (E)-2-(2-chloro-6-fluorobenzamido)-5-[4-(methyl-pyrimidin-2-ylamino)phenyl]pent-4-enoic acid methyl ester (39 mg).

Example 65

(E)-2-(2-Chloro-6-fluorobenzamido)-5-[4-(methyl-pyrimidin-2-ylamino)phenyl]pent-4-enoic acid

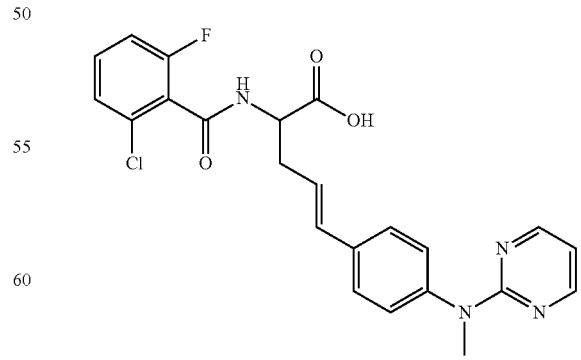

In the same manner as in Example 2, (E)-2-(2-chloro-6-fluorobenzamido)-5-[4-(methyl-pyrimidin-2-ylamino)phenyl]pent-4-enoic acid methyl ester (39 mg) was hydrolyzed to obtain (E)-2-(2-chloro-6-fluorobenzamido)-5-[4-(methyl-pyrimidin-2-ylamino)phenyl]pent-4-enoic acid (34 mg).

Example 66

(E)-2-(2-Chloro-6-methylbenzamido)-5-[4-(methyl-pyrimidin-2-ylamino)phenyl]pent-4-enoic acid methyl ester

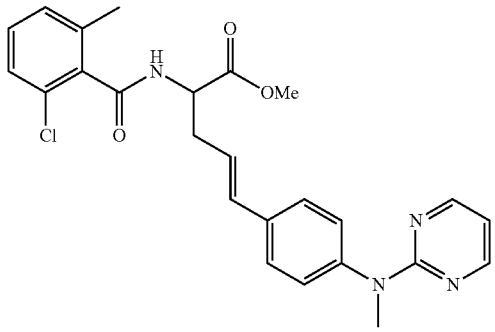 [SMILES: COC(=O)C(C/C=C/c1ccc(N(C)c2ncccn2)cc1)NC(=O)c1c(C)cccc1Cl]

Under an argon atmosphere, oxalyl dichloride (0.022 ml) and DMF (0.002 ml) were added to a solution of 2-chloro-6-methylbenzoic acid (29 mg) in dichloromethane (1.0 ml), and the resulting mixture was stirred at room temperature for 1 hour. The reaction solution was concentrated and the residue was dissolved in dichloromethane (1.0 ml). To the solution, 2-amino-5-[4-(methyl-pyrimidin-2-ylamino)phenyl]pent-4-enoic acid methyl ester (50 mg) and triethylamine (0.05 ml) were added, and the resulting mixture was stirred at room temperature for 2.5 hours. To the reaction solution, 1N hydrochloric acid was added, and the resulting solution was extracted with dichloromethane. Organic layer was washed with saturated aqueous sodium hydrogen carbonate solution and dried over anhydrous sodium sulfate. After removing anhydrous sodium sulfate by filtration, the filtrate was concentrated. The residue was purified by thin layer chromatography (silica gel, mobile phase: hexane/ethyl acetate=1/1) to obtain (E)-2-(2-chloro-6-methylbenzamido)-5-[4-(methyl-pyrimidin-2-ylamino)phenyl]pent-4-enoic acid methyl ester (63 mg).

Example 67

(E)-2-(2-Chloro-6-methylbenzamido)-5-[4-(methyl-pyrimidin-2-ylamino)phenyl]pent-4-enoic acid

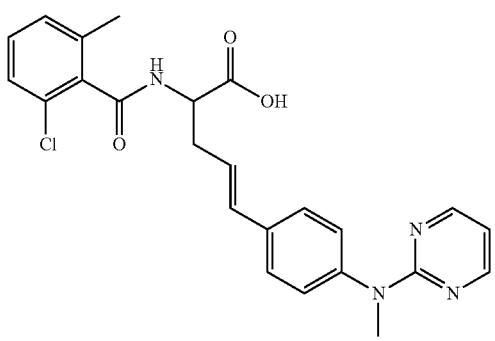 [SMILES: Cc1cccc(Cl)c1C(=O)NC(C/C=C/c1ccc(N(C)c2ncccn2)cc1)C(=O)O]

In the same manner as in Example 2, (E)-2-(2-chloro-6-methylbenzamido)-5-[4-(methyl-pyrimidin-2-ylamino)phenyl]pent-4-enoic acid methyl ester (63 mg) was hydrolyzed to obtain (E)-2-(2-chloro-6-methylbenzamido)-5-[4-(methyl-pyrimidin-2-ylamino)phenyl]pent-4-enoic acid (57 mg).

Example 68

(E)-2-(2,6-Dimethylbenzamido)-5-[4-(methyl-pyrimidin-2-ylamino)phenyl]pent-4-enoic acid methyl ester

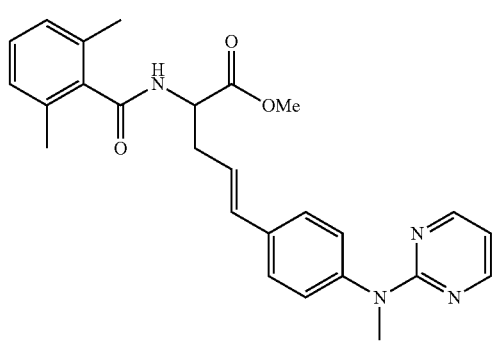 [SMILES: COC(=O)C(C/C=C/c1ccc(N(C)c2ncccn2)cc1)NC(=O)c1c(C)cccc1C]

Under an argon atmosphere, oxalyl dichloride (0.025 ml) and DMF (0.002 ml) were added to a solution of 2,6-dimethylbenzoic acid (24 mg) in dichloromethane (1.0 ml), and the resulting mixture was stirred at room temperature for 2 hours. The reaction solution was concentrated and the residue was dissolved in dichloromethane (1.0 ml). To the solution, 2-amino-5-[4-(methyl-pyrimidin-2-ylamino)phenyl]pent-4-enoic acid methyl ester (50 mg) and triethylamine (0.05 ml) were added, and the resulting mixture was stirred at room temperature for 3 hours. To the reaction solution, 1N hydrochloric acid was added, and the resulting solution was extracted with dichloromethane, followed by drying the organic layer over anhydrous sodium sulfate. After removing anhydrous sodium sulfate by filtration, the filtrate was concentrated. The residue was purified by thin layer chromatography (silica gel, mobile phase: hexane/ethyl acetate=3/2) to obtain (E)-2-(2,6-dimethylbenzamido)-5-[4-(methyl-pyrimidin-2-ylamino)phenyl]pent-4-enoic acid methyl ester (62 mg).

Example 69

(E)-2-(2,6-Dimethylbenzamido)-5-[4-(methyl-pyrimidin-2-ylamino)phenyl]pent-4-enoic acid

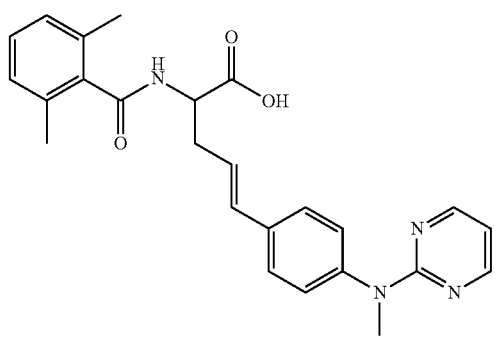 [SMILES: Cc1cccc(C)c1C(=O)NC(C/C=C/c1ccc(N(C)c2ncccn2)cc1)C(=O)O]

In the same manner as in Example 2, (E)-2-(2,6-dimethyl-benzamido)-5-[4-(methyl-pyrimidin-2-ylamino)phenyl]pent-4-enoic acid methyl ester (62 mg) was hydrolyzed to obtain (E)-2-(2,6-dimethylbenzamido)-5-[4-(methyl-pyrimidin-2-ylamino)phenyl]pent-4-enoic acid (47 mg).

Example 70

(E)-5-[4-((2-Cyano-ethyl)-pyrimidin-2-yl-amino)-phenyl]-2-(2,6-difluorobenzamido)-pent-4-enoic acid methyl ester

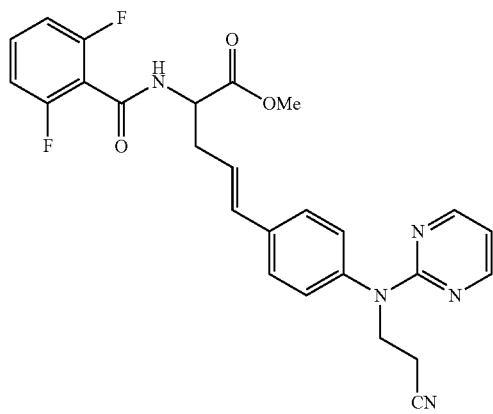 [SMILES: COC(=O)C(C/C=C/c1ccc(N(CCC#N)c2ncccn2)cc1)NC(=O)c1c(F)cccc1F]

In the same manner as in Example 1, 2-(2,6-difluorobenzamido)pent-4-enoic acid methyl ester (17 mg) was reacted with 3-(N-(4-iodophenyl)-N-(pyrimidin-2-yl)amino)propanenitrile (24 mg) to obtain ((E)-5-[4-((2-cyano-ethyl)-pyrimidin-2-yl-amino)-phenyl]-2-(2,6-difluorobenzamido)-pent-4-enoic acid methyl ester (18 mg). Column chromatography (silica gel, eluent: hexane/ethyl acetate=2/1) was used for purification.

Example 71

(E)-5-[4-((2-Cyano-ethyl)-pyrimidin-2-yl-amino)-phenyl]-2-(2,6-difluorobenzamido)-pent-4-enoic acid

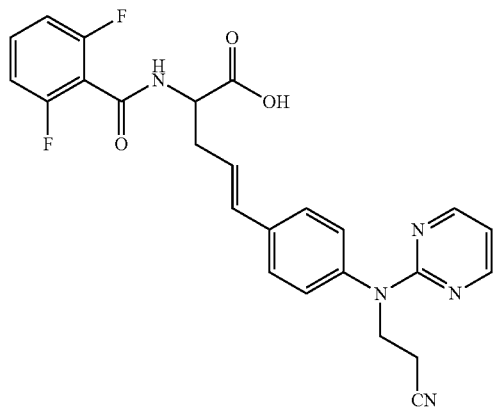 [SMILES: N#CCCN(c1ccc(/C=C/CC(NC(=O)c2c(F)cccc2F)C(=O)O)cc1)c1ncccn1]

In the same manner as in Example 2, (E)-5-[4-((2-cyano-ethyl)-pyrimidin-2-yl-amino)-phenyl]-2-(2,6-difluorobenzamido)-pent-4-enoic acid methyl ester (18 mg) was hydrolyzed to obtain (E)-5-[4-((2-cyano-ethyl)-pyrimidin-2-yl-amino)-phenyl]-2-(2,6-difluorobenzamido)-pent-4-enoic acid (10 mg).

Example 72

2-(2,6-Dichlorobenzamid)-5-[4-(pyrimidin-2-yloxy)phenyl]pent-4-ynoic acid methyl ester

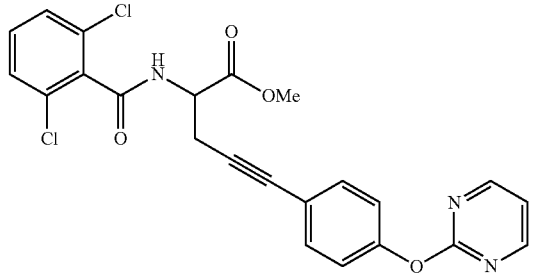

Under an argon atmosphere, copper iodide (2.8 mg) and dichlorobis(triphenylphosphine)palladium (5.2 mg) were added to a solution of 2-(2,6-dichlorobenzamido)pent-4-ynoic acid methyl ester (74 mg) and 2-(4-iodophenoxy)pyrimidine (81 mg) in THF/diisopropylamine (3/1) mixture (5 ml), and the resulting mixture was stirred at room temperature for 2 hours. The reaction solution was concentrated and ethyl acetate was added to the residue. The insoluble matter was removed by filtration, and the filtrate was washed once with water and once with saturated brine and dried over anhydrous sodium sulfate. After removing anhydrous sodium sulfate by filtration, the filtrate was concentrated. The residue was purified by column chromatography (silica gel, eluent: cyclohexane/chloroform=2/1→cyclohexane/chloroform=1/3) to obtain 2-(2,6-dichlorobenzamido)-5-[4-(pyrimidin-2-yloxy)phenyl]pent-4-ynoic acid methyl ester (100 mg).

Example 73

2-(2,6-Dichlorobenzamido)-5-[4-(pyrimidin-2-yloxy)phenyl]pent-4-ynoic acid sodium salt

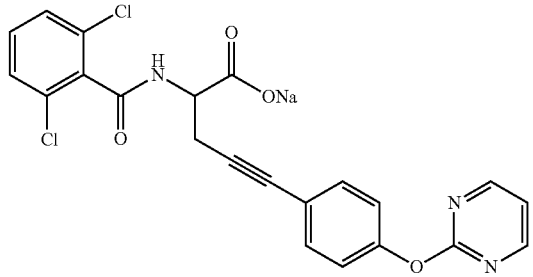

In the same manner as in Example 8, 2-(2,6-dichlorobenzamido)-5-[4-(pyrimidin-2-yloxy)phenyl]pent-4-ynoic acid methyl ester (100 mg) was hydrolyzed to obtain 2-(2,6- dichlorobenzamido)-5-[4-(pyrimidin-2-yloxy)phenyl]pent-4-ynoic acid sodium salt (85 mg).

Example 74

(E)-2-(2,6-Dichlorobenzamido)-5-[4-(pyrimidin-2-ylamino)phenyl]pent-4-ynoic acid methyl ester

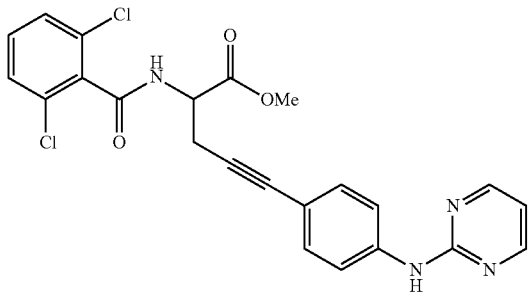 [SMILES: COC(=O)C(CC#Cc1ccc(Nc2ncccn2)cc1)NC(=O)c1c(Cl)cccc1Cl]

In the same manner as in Example 72, 2-(2,6-dichlorobenzamido)pent-4-ynoic acid methyl ester (50.0 mg) was reacted with N-(4-iodophenyl)pyrimidin-2-amine (49.5 mg) to obtain (E)-2-(2,6-dichlorobenzamido)-5-[4-(pyrimidin-2-ylamino)phenyl]pent-4-ynoic acid methyl ester (80.0 mg). Column chromatography (silica gel, eluent: chloroform/cyclohexane=3/1→chloroform/ethyl acetate=5/1) and thin layer chromatography (silica gel, mobile phase: chloroform/ethyl acetate=3/1) were used for purification.

Example 75

(E)-2-(2,6-Dichlorobenzamido)-5-[4-(pyrimidin-2-ylamino)phenyl]pent-4-ynoic acid sodium salt

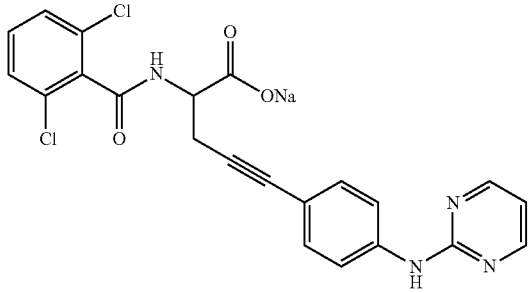

In the same manner as in Example 8, (E)-2-(2,6-dichlorobenzamido)-5-[4-(pyrimidin-2-ylamino)phenyl]pent-4-ynoic acid methyl ester (80.0 mg) was hydrolyzed to obtain (E)-2-(2,6-dichlorobenzamido)-5-[4-(pyrimidin-2-ylamino)phenyl]pent-4-ynoic acid sodium salt (62.3 mg).

Example 76

(S,E)-2-(2,6-Dichlorobenzamido)-5-[4-(4-methoxytetrahydropyran-4-yl)-phenyl]pent-4-enoic acid methyl ester

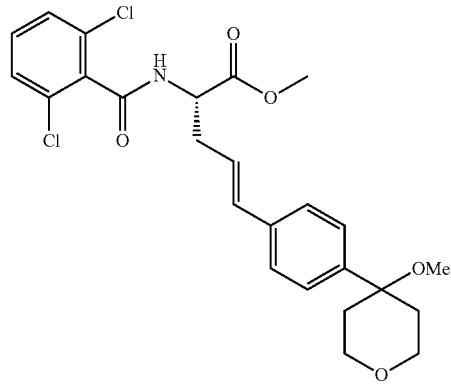 [SMILES: COC(=O)[C@H](C/C=C/c1ccc(C2(OC)CCOCC2)cc1)NC(=O)c1c(Cl)cccc1Cl]

Under an argon atmosphere, palladium acetate (295 mg) and tris(2-methylphenyl)phosphine (384 mg) were added to a suspension of (S)-2-(2,6-dichlorobenzamido)pent-4-enoic acid methyl ester (7.60 g), tetrahydro-4-(4-iodophenyl)-4-methoxy-2H-pyran (8.00 g) and potassium carbonate (5.21 g) in DMF (90 ml), and the resulting mixture was stirred at 80° C. for 2 hours. After cooling the reaction solution to room temperature, ethyl acetate was added thereto, and the resulting mixture was washed 3 times with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=2/1-1/4). The obtained crude product was further purified by column chromatography (silica gel, eluent: cyclohexane/ethyl acetate=4/1) to obtain (S,E)-2-(2,6-dichlorobenzamido)-5-[4-(4-methoxytetrahydropyran-4-yl)-phenyl]pent-4-enoic acid methyl ester (9.80 g).

Example 77

(S,E)-2-(2,6-Dichlorobenzamido)-5-[4-(4-methoxytetrahydropyran-4-yl)-phenyl]pent-4-enoic acid

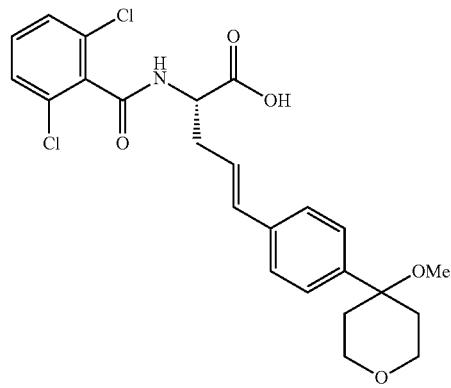 [SMILES: COC1(c2ccc(/C=C/C[C@H](NC(=O)c3c(Cl)cccc3Cl)C(=O)O)cc2)CCOCC1]

In a mixed solvent of THF (250 ml) and water (125 ml), (S,E)-2-(2,6-dichlorobenzamido)-5-[4-(4-methoxytetrahydropyran-4-yl)-phenyl]pent-4-enoic acid methyl ester (9.80 g) was dissolved, and the resulting mixture was cooled to 0° C. Barium hydroxide octahydrate (3.14 g) was added thereto and the resulting mixture was stirred at 0° C. for 8 hours. The reaction solution was concentrated to remove THF, and water (150 ml) was added thereto, followed by washing the resulting mixture with ether. Aqueous layer was acidified by adding 1N hydrochloric acid in small portions thereto and extracted 3 times with ethyl acetate. Organic layers were washed with saturated brine and dried over anhydrous sodium sulfate. After removing anhydrous sodium sulfate by filtration, the filtrate was concentrated. The residue was purified by column chromatography (silica gel, eluent: chloroform/methanol=10/1). The obtained crude product was further purified by column chromatography (silica gel, eluent: cyclohexane/ethyl acetate=1/1→ethyl acetate) to obtain (S,E)-2-(2,6-dichlorobenzamido)-5-[4-(4-methoxytetrahydropyran-4-yl)-phenyl]pent-4-enoic acid (6.15 g).

Example 78

(S,E)-2-(2,6-Dichlorobenzamido)-5-[4-(4-methoxytetrahydropyran-4-yl)-phenyl]pent-4-enoic acid sodium salt

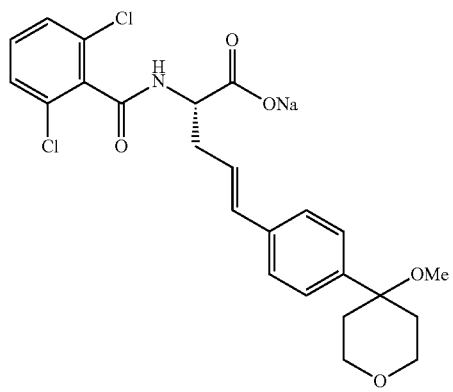

To (S,E)-2-(2,6-dichlorobenzamido)-5-[4-(4-methoxytetrahydropyran-4-yl)-phenyl]pent-4-enoic acid (4.24 g), THF (8.86 ml) and 1N aqueous sodium hydroxide solution (8.86 ml) were added, and the resulting mixture was stirred at room temperature for 5 minutes. The reaction solution was concentrated to dryness to obtain (S,E)-2-(2,6-dichlorobenzamido)-5-[4-(4-methoxytetrahydropyran-4-yl)-phenyl]pent-4-enoic acid sodium salt (4.30 g).

Example 79

(S,E)-2-(2,6-Dichlorobenzamido)-5-[4-(methyl-pyrimidin-2-ylamino)phenyl]pent-4-enoic acid methyl ester

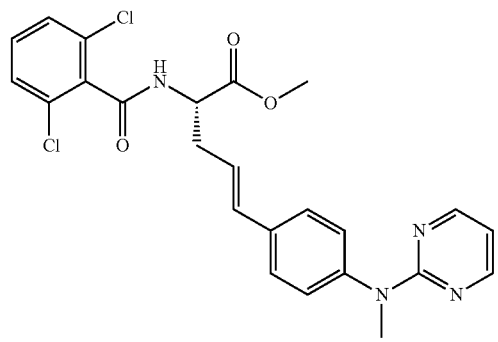 [SMILES: COC(=O)[C@H](C/C=C/c1ccc(N(C)c2ncccn2)cc1)NC(=O)c1c(Cl)cccc1Cl]

Under an argon atmosphere, palladium acetate (93.2 mg) and tris(2-methylphenyl)phosphine (121.2 mg) were added to a suspension of (S)-2-(2,6-dichlorobenzamido)pent-4-enoic acid methyl ester (1.20 g), N-(4-iodophenyl)-N-methylpyrimidin-2-amine (1.24 g) and potassium carbonate (824 mg) in DMF (20 ml), and the resulting mixture was stirred at 80° C. for 3 hours. After cooling the reaction solution to room temperature, ethyl acetate was added thereto, and the resulting mixture was washed twice with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=1/1→chloroform). The obtained crude product was purified again by column chromatography (silica gel, eluent: cyclohexane/ethyl acetate=4/1→2/1) to obtain (S,E)-2-(2,6-dichlorobenzamido)-5-[4-(methyl-pyrimidin-2-ylamino)phenyl]pent-4-enoic acid methyl ester (1.28 g).

Example 80

(S,E)-2-(2,6-Dichlorobenzamido)-5-[4-(methyl-pyrimidin-2-ylamino)phenyl]pent-4-enoic acid

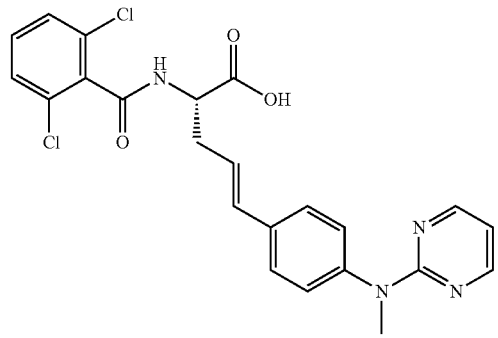 [SMILES: CN(c1ccc(/C=C/C[C@H](NC(=O)c2c(Cl)cccc2Cl)C(=O)O)cc1)c1ncccn1]

A solution of (S,E)-2-(2,6-dichlorobenzamido)-5-[4-(methyl-pyrimidin-2-ylamino)phenyl]pent-4-enoic acid methyl ester (1.28 g) in THF (45 ml) was cooled to 0° C. To the solution, 0.1N aqueous lithium hydroxide solution (40 ml) was added, and the resulting mixture was stirred at 0° C. for 40 minutes. Water (50 ml) was added to the reaction solution, and the resulting mixture was washed with ether. Aqueous layer Was acidified by adding 1N hydrochloric acid in small portions thereto, and extracted twice with ethyl acetate. Organic layers were washed with saturated brine and dried over anhydrous sodium sulfate. After removing anhydrous sodium sulfate by filtration, the filtrate was concentrated to dryness to obtain (S,E)-2-(2,6-dichlorobenzamido)-5-[4-(methyl-pyrimidin-2-ylamino)phenyl]pent-4-enoic acid (1.01 g).

Example 81

(S,E)-2-(2,6-Dichlorobenzamido)-5-[4-(methyl-pyrimidin-2-ylamino)phenyl]pent-4-enoic acid sodium salt

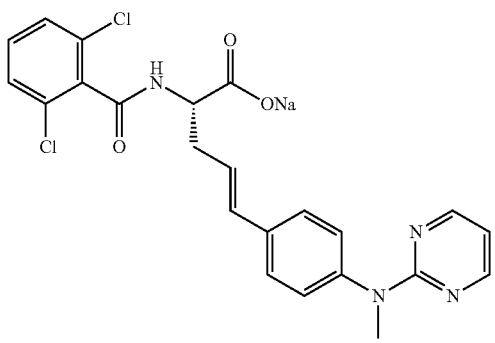

To a solution of (S,E)-2-(2,6-dichlorobenzamido)-5-[4-(methyl-pyrimidin-2-ylamino)phenyl]pent-4-enoic acid (10.60 g) in methanol (200 ml), 1N aqueous sodium hydroxide solution (22.5 ml) was added, and the resulting mixture was stirred at room temperature for 5 minutes. The reaction solution was concentrated to dryness to obtain (S,E)-2-(2,6-dichlorobenzamido)-5-[4-(methyl-pyrimidin-2-ylamino) phenyl]pent-4-enoic acid sodium salt (11.08 g). IR (KBr)cm$^{-1}$: 3385, 1584, 1552, 1486, 1431, 1397, 1315, 1195, 1112, 968, 799.

Example 82

(S,E)-2-(2,6-Dichlorobenzamido)-5-[4-(isopropyl-pyrimidin-2-ylamino)phenyl]pent-4-enoic acid methyl ester

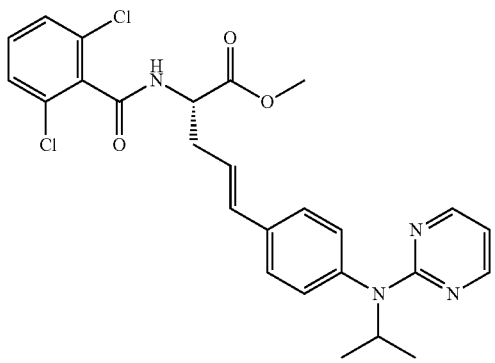 [SMILES: COC(=O)[C@H](C/C=C/c1ccc(N(c2ncccn2)C(C)C)cc1)NC(=O)c1c(Cl)cccc1Cl]

Under an argon atmosphere, palladium acetate (19.9 mg) and tris(2-methylphenyl)phosphine (25.9 mg) were added to a suspension of (S)-2-(2,6-dichlorobenzamido)pent-4-enoic acid methyl ester (514.4 mg), N-(4-iodophenyl)-N-isopropylpyrimidin-2-amine (577.4 mg) and potassium carbonate (352.9 mg) in DMF (6 ml), and the resulting mixture was stirred at 80° C. for 7 hours. After cooling the reaction solution to room temperature, ethyl acetate was added thereto, and the resulting mixture was washed twice with water and once with saturated brine, followed by drying the organic layer over anhydrous sodium sulfate. After removing anhydrous sodium sulfate by filtration, the filtrate was concentrated. The residue was purified by column chromatography (silica gel, eluent: cyclohexane/chloroform=2/1→1/1→1/3). The obtained crude product was purified again by column chromatography (silica gel, eluent: cyclohexane/ethyl acetate=6/1→4/1→2/1) to obtain (S,E)-2-(2,6-dichlorobenzamido)-5-[4-(isopropyl-pyrimidin-2-ylamino)phenyl]pent-4-enoic acid methyl ester (553.6 mg).

Example 83

(S,E)-2-(2,6-Dichlorobenzamido)-5-[4-(isopropyl-pyrimidin-2-ylamino)phenyl]pent-4-enoic acid

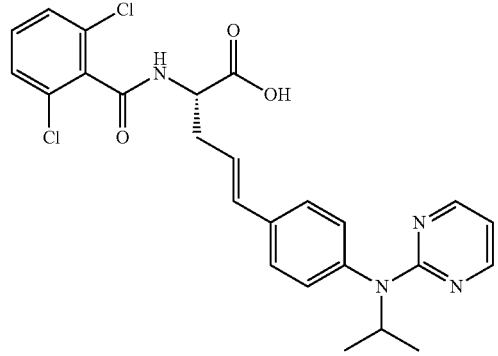

A solution of (S,E)-2-(2,6-dichlorobenzamido)-5-[4-(isopropyl-pyrimidin-2-ylamino)phenyl]pent-4-enoic acid methyl ester (526.2 g) in THF (15 ml) was cooled to 0° C. To the solution, 0.1N aqueous lithium hydroxide solution (15.4 ml) was added, and the resulting mixture was stirred at 0° C. for 40 minutes. Water (20 ml) was added to the reaction solution and the resulting mixture was washed with ether. Aqueous layer was acidified by adding 1N hydrochloric acid in small portions thereto, and extracted twice with ethyl acetate. Organic layers were washed with saturated brine and dried over anhydrous sodium sulfate. After removing anhydrous sodium sulfate by filtration, the filtrate was concentrated to dryness to obtain (S,E)-2-(2,6-dichlorobenzamido)-5-[4-(isopropyl-pyrimidin-2-ylamino)phenyl]pent-4-enoic acid (420.7 mg).

Example 84

(S,E)-2-(2,6-Dichlorobenzamido)-5-[4-(isopropyl-pyrimidin-2-ylamino)phenyl]pent-4-enoic acid sodium salt

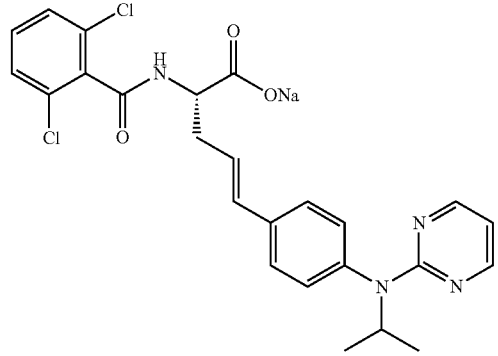

To a suspension of (S,E)-2-(2,6-dichlorobenzamido)-5-[4-(isopropyl-pyrimidin-2-ylamino)phenyl]pent-4-enoic acid (390.4 mg) in methanol (15 ml), 1N aqueous sodium hydroxide solution (0.782 ml) was added, and the resulting mixture was stirred at room temperature for 5 minutes. The reaction solution was concentrated to dryness to obtain (S,E)-2-(2,6-dichlorobenzamido)-5-[4-(isopropyl-pyrimidin-2-ylamino)phenyl]pent-4-enoic acid sodium salt (388.8 mg). IR (KBr) cm$^{-1}$: 3386, 2974, 1585, 1549, 1509, 1455, 1292, 1122, 968, 798, 780.

The spectral data of the compounds of Examples 1 to 84 are shown in Tables 8-16.

TABLE 8

| Ex No. | Y | M | ESI-MS | NMR (H1) chemical shift |
|---|---|---|---|---|
| 1 | 4-hydroxytetrahydropyran-4-yl | Me | 478 (M + H)$^+$ | CDCl$_3$, δ 1.62-1.67 (2H, m), 2.11-2.19 (2H, m), 2.79-2.97 (2H, m), 3.81 (3H, s), 3.84-3.95 (4H, m), 5.01-5.05 (1H, m), 6.13-6.17 (1H, m), 6.50-6.54 (2H, m), 7.24-7.34 (5H, m), 7.42 (2H, d, J = 8.1 Hz) |
| 2 | 4-hydroxytetrahydropyran-4-yl | H | 462 (M − H)$^-$ | CDCl$_3$, δ 1.66 (4H, m), 2.82 (1H, m), 2.98 (1H, m), 3.86 (4H, m), 4.95 (1H, m), 6.22 (1H, m), 6.56 (1H, m), 7.24-7.40 (7H, m) |
| 3 | 4-methoxytetrahydropyran-4-yl | Me | 492 (M + H)$^+$ | CDCl$_3$, δ 1.92 (4H, br), 2.77-2.84 (1H, m), 2.94-2.96 (4H, brm), 3.73-3.80 (7H, brm), 5.03 (1H, dd, J = 12.9, 5.6 Hz), 6.12-6.20 (1H, m), 6.52 (1H, d, J = 15.6 Hz), 6.73-6.75 (1H, br), 7.22-7.45 (7H, m) |
| 4 | 4-methoxytetrahydropyran-4-yl | H | 476 (M − H)$^-$ | dmso-d$^6$, δ 1.87-1.90 (4H, m), 2.56-2.63 (1H, m), 2.68-2.74 (1H, m), 2.84 (3H, s), 3.66-3.68 (4H, m), 4.55-4.58 (1H, brm), 6.30 (1H, td, J = 15.9, 7.1 Hz), 6.50 (1H, d, J = 15.9 Hz), 7.31-7.50 (7H, m), 9.10 (1H, brs), 12.77 (1H, brs) |
| 5 | 4-ethoxytetrahydropyran-4-yl | Me | 506 (M + H)$^+$ | CDCl$_3$, δ 1.14 (3H, t, J = 7.1 Hz), 1.92-2.04 (4H, m), 2.80-2.98 (2H, m), 3.05-3.11 (2H, dd, J = 14.2, 7.1 Hz), 3.81 (3H, s), 3.74-3.92 (4H, m), 5.02-5.06 (1H, m), 6.13-6.17 (1H, m), 6.48 (1H, d, J = 7.6 Hz), 6.52 (1H, d, J = 15.9 Hz), 7.25-7.34 (7H, m) |
| 6 | 4-ethoxytetrahydropyran-4-yl | H | 490 (M − H)$^-$ | CDCl$_3$, δ 1.13 (3H, t, J = 6.8 Hz), 1.95 (4H, m), 2.87 (1H, m), 3.04 (1H, m), 3.07 (2H, q, J = 7.1 Hz), 3.89 (4H, m), 5.03 (1H, m), 6.22 (1H, m), 6.57 (2H, m), 7.23-7.32 (7H, m) |
| 7 | 4-methoxymethyltetrahydropyran-4-yl | Me | 506 (M + H)$^+$ | |

TABLE 8-continued

| Ex No. | Y | M | ESI-MS | NMR (H1) chemical shift |
|---|---|---|---|---|
| 8 | (4-methoxymethyl-tetrahydropyran-4-yl)oxy | Na | 490 (M − Na)⁻ | dmso-d6, δ 1.80-1.86 (2H, m), 1.97-2.01 (2H, m), 2.59-2.66 (1H, m), 2.75-2.79 (1H, m), 3.11 (3H, s), 3.29-3.34 (4H, m), 3.64-3.67 (2H, m), 4.01 (1H, brd, J = 5.9 Hz), 6.19-6.27 (1H, m), 6.36 (1H, d, J = 16.1 Hz), 7.24-7.47 (7H, m), 7.69 (1H, d, J = 6.1 Hz) |
| 9 | (4-methoxy-oxepan-4-yl)oxy | Me | 506 (M + H)⁺ | |
| 10 | (4-methoxy-oxepan-4-yl)oxy | Na | 490 (M − Na)⁻ | dmso-d⁶, δ 1.85-1.94 (2H, m), 2.03-2.51 (4H, m), 2.59-2.66 (1H, m), 2.75-2.82 (1H, m), 2.88 (3H, s), 3.52-3.72 (4H, m), 3.99 (1H, dd, J = 11.0, 5.4 Hz), 6.21-6.28 (1H, m), 6.37 (1H, d, J = 15.9 Hz), 7.28 (4H, s), 7.34-7.43 (1H, m), 7.46 (2H, d, J = 7.1 Hz), 7.67 (1H, d, J = 5.6 Hz) |

TABLE 9

| Ex. No | Y | M | ESI-MS | NMR (H1) chemical shift |
|---|---|---|---|---|
| 11 | pyrimidin-2-yloxy | Me | 472 (M + H)⁺ | CDCl₃, δ 2.71-2.78 (1H, m), 2.86-2.92 (1H, m), 3.73 (3H, s), 4.93-4.98 (1H, m), 5.99-6.07 (1H, m), 6.45 (1H, d, J = 15.9 Hz), 6.52 (1H, br), 6.95 (1H, t, J = 4.9 Hz), 7.05 (2H, d, J = 8.5 Hz), 7.08-7.25 (3H, m), 7.30 (2H, d, J = 8.5 Hz), 8.47 (2H, d, J = 4.9 Hz) |
| 12 | pyrimidin-2-yloxy | H | 456 (M − H)⁻ | dmso-d⁶, δ 2.57-2.64 (1H, m), 2.71-2.76 (1H, m), 4.57-4.62 (1H, m), 6.24-6.31 (1H, m), 6.53 (1H, d, J = 15.9 Hz), 7.14 (2H, d, J = 8.5 Hz), 7.25 (1H, t, J = 4.9 Hz), 7.35-7.49 (5H, m), 8.63 (2H, d, J = 4.9 Hz), 9.14 (1H, d, J = 8.1 Hz), 12.78 (1H, brs) |
| 13 | (5-ethylpyrimidin-2-yl)oxy | Me | 500 (M + H)⁺ | |

TABLE 9-continued

| Ex. No | Y | M | ESI-MS | NMR (H1) chemical shift |
|---|---|---|---|---|
| 14 | 5-(ethyl)pyrimidin-2-yloxy | Na | 484 (M − Na)⁻ | CDCl₃, δ 1.25 (3H, t, J = 7.6 Hz), 2.62 (2H, dd, J = 7.6, 4.2 Hz), 2.86 (1H, m), 2.92 (1H, m), 4.96 (1H, m), 6.10 (1H, dt, J = 15.9, 7.6 Hz), 6.47 (1H, d, J = 15.9 Hz), 6.62 (1H, d, J = 7.3 Hz), 7.02 (2H, d, J = 8.6 Hz), 7.30 (5H, m), 8.42 (2H, s) |
| 15 | 4-methoxypyrimidin-2-yloxy | Me | 502 (M + H)⁺ | |
| 16 | 4-methoxypyrimidin-2-yloxy | H | 486 (M − H)⁻ | CDCl₃, δ 2.83 (1H, m), 2.98 (1H, m), 3.82 (3H, s), 5.04 (1H, dd, J = 5.4 and 13.0 Hz), 6.10 (1H, m), 6.45-6.55 (2H, m), 7.07-7.48 (7H, m), 8.17 (1H, d, J = 5.6 Hz) |
| 17 | 4,6-dimethoxypyrimidin-2-yloxy | Me | 532 (M + H)⁺ | |
| 18 | 4,6-dimethoxypyrimidin-2-yloxy | H | 516 (M − H)⁻ | CDCl₃, δ 2.80 (1H, m), 2.93 (1H, m), 3.81 (6H, s), 5.03 (1H, m), 5.97 (1H, m), 6.42-6.46 (2H, m), 6.84 (2H, d, J = 12.0 Hz), 7.24-7.38 (5H, m) |
| 19 | 4,6-dimethylpyrimidin-2-yloxy | Me | 502 (M + H)⁺ | |
| 20 | 4,6-dimethylpyrimidin-2-yloxy | H | 484 (M − H)⁻ | CDCl₃, δ 2.40 (6H, s), 2.84 (1H, m), 2.97 (1H, m), 5.05 (1H, m), 6.09 (1H, m), 6.46-6.55 (2H, m), 6.76 (2H, s), 7.07-7.35 (5H, m) |

TABLE 10

[Structure: 2,6-dichlorobenzamide linked to CH(CO₂M)-CH₂-CH=CH-C₆H₄-Y]

| Ex No. | Y | M | ESI-MS | NMR (H1) chemical shift |
|---|---|---|---|---|
| 21 | N-methyl-N-(pyrimidin-2-yl)amino | Me | 485 (M + H)⁺ | CDCl₃, δ 2.78-2.85 (1H, m), 2.91-2.98 (1H, m), 3.49 (3H, s), 3.79 (3H, s), 4.99-5.04 (1H, m), 6.04-6.12 (1H, m), 6.43 (1H, d, J = 7.8 Hz), 6.50 (1H, d, J = 15.9 Hz), 6.55 (1H, t, J = 4.6 Hz), 7.22-7.35 (7H, m), 8.31 (2H, d, J = 4.6 Hz) |
| 22 | N-methyl-N-(pyrimidin-2-yl)amino | H | 469 (M − H)⁻ | dmso-d⁶, δ 2.57-2.64 (1H, m), 2.69-2.73 (1H, m), 3.43 (3H, s), 4.58 (1H, dd, J = 13.4, 8.3 Hz), 6.27 (1H, td, J = 16.1, 7.3 Hz), 6.51 (1H, d, J = 16.1 Hz), 6.72 (1H, t, J = 4.9 Hz), 7.27 (2H, d, J = 8.3 Hz), 7.35 (2H, d, J = 8.5Hz), 7.39-7.49 (3H, m), 8.34-8.36 (2H, m), 9.14 (1H, d, J = 8.3 Hz), 12.76 (1H, s) |
| 23 | N-ethyl-N-(pyrimidin-2-yl)amino | Me | 499 (M + H)⁺ | CDCl₃, δ 1.23 (3H, t, J = 6.8 Hz), 2.81-3.00 (2H, m), 3.82 (3H, s), 4.01 (2H, q, J = 6.8 Hz), 5.04 (1H, dt, J = 5.1, 7.8 Hz), 6.11 (1H, dt, J = 7.8, 15.4 Hz), 6.45 (1H, d, J = 7.8 Hz), 6.53 (1H, t, J = 4.9 Hz), 6.45 (1H, d, J = 15.4 Hz), 7.19-7.38 (7H, m), 8.31 (2H, d, J = 4.9 Hz). |
| 24 | N-ethyl-N-(pyrimidin-2-yl)amino | H | 483 (M − H)⁻ | dmso-d⁶, δ 1.12 (3H, t, J = 6.8 Hz), 2.57-2.75 (2H, m), 3.95 (2H, q, J = 6.8 Hz), 4.58 (1H, dt, J = 5.1, 8.3 Hz), 6.28 (1H, dt, J = 7.1, 15.6 Hz), 6.52 (1H, d, J = 15.6 Hz), 6.68 (1H, t, J = 4.9 Hz), 7.19-7.49 (7H, m), 8.32 (2H, d, J = 4.9 Hz), 9.13 (1H, d, J = 8.3 Hz). |
| 25 | N-(2-methoxyethyl)-N-(pyrimidin-2-yl)amino | Me | 529 (M + H)⁺ | CDCl₃, δ 2.81-3.00 (2H, m), 3.32 (3H, s), 3.63 (2H, t, J = 5.9 Hz), 3.82 (3H, s), 4.15 (2H, t, J = 5.9 Hz), 5.04 (1H, dt, J = 5.1, 7.8 Hz), 6.11 (1H, dt, J = 7.3, 15.4 Hz), 6.45 (1H, d, J = 7.8 Hz), 6.53 (1H, d, J = 15.4 Hz), 6.55 (1H, t, J = 4.9 Hz), 7.24-7.37 (7H, m), 8.31 (2H, d, J = 4.9 Hz). |
| 26 | N-(2-methoxyethyl)-N-(pyrimidin-2-yl)amino | Na | 513 (M − Na)⁻ | dmso-d⁶, δ 2.60-2.82 (2H, m), 3.19 (3H, s), 3.51 (2H, t, J = 6.1 Hz), 4.01-4.06 (3H, m), 6.23 (1H, dt, J = 7.1, 15.6 Hz), 6.38 (1H, d, J = 15.6 Hz), 6.69 (1H, t, J = 4.9 Hz), 7.18-7.46 (7H, m), 7.70-7.72 (1H, m), 8.32 (2H, d, J = 4.9 Hz) |
| 27 | N-isopropyl-N-(pyrimidin-2-yl)amino | Me | 513 (M + H)⁺ | CDCl₃, δ 1.15 (6H, d, J = 6.8 Hz), 2.82-3.01 (2H, m), 3.83 (3H, s), 5.05 (1H, dt, J = 5.1, 7.6 Hz), 5.15 (1H, dq, J = 6.6, 6.8 Hz), 6.14 (1H, dt, J = 7.6, 15.9 Hz), 6.47 (1H, d, J = 7.6 Hz), 6.48 (1H, t, J = 4.9 Hz), 6.55 (1H, d, J = 15.9 Hz), 7.06-7.40 (7H, m), 8.28 (2H, d, J = 4.9 Hz). |

TABLE 10-continued

Structure: 2,6-dichlorobenzamide with α-amino acid CO₂M, side chain = CH₂-CH=CH-(4-Y-phenyl)

| Ex No. | Y | M | ESI-MS | NMR (H1) chemical shift |
|---|---|---|---|---|
| 28 | ![N(iPr)-pyrimidin-2-yl] (N-isopropyl-N-(pyrimidin-2-yl)amino) | H | 497 (M − H)⁻ | dmso-d$^6$, δ 1.06 (3H, s), 1.08 (3H, s), 2.59-2.66 (1H, m), 2.70-2.76 (1H, m), 4.60 (1H, td, J = 8.3, 5.1 Hz), 5.06 (1H, td, J = 13.4, 6.6 Hz), 6.31 (1H, td, J = 14.9, 7.1 Hz), 6.54 (1H, d, J = 15.9 Hz), 6.62 (1H, t, J = 4.9 Hz), 7.05 (2H, d, J = 8.3 Hz), 7.38-7.43 (3H, m), 7.48 (2H, d, J = 8.5 Hz), 8.34-8.36 (2H, m), 9.15 (1H, d, J = 8.3 Hz), 12.77(1H, s) |
| 29 | N-(4-hydroxybenzyl)-N-(pyrimidin-2-yl)amino | H | 561 (M − H)⁻ | CDCl$_3$, δ 2.62 (2H, m), 4.74 (1H, dd, J = 7.6, 4.6 Hz), 5.01 (1H, brs), 5.08 (1H, dd, J = 25.9, 15.4 Hz), 5.84 (1H, dt, J = 15.9, 8.1 Hz), 6.16 (1H, d, J = 15.9 Hz), 6.35 (1H, d, J = 7.3 Hz), 6.66 (3H, m), 6.98 (1H, brs), 7.05 (4H, m), 7.25 (5H, m), 8.41 (2H, d, J = 4.9 Hz) |
| 30 | N-(2-cyanoethyl)-N-(pyrimidin-2-yl)amino | Me | 524 (M + H)⁺ | CDCl$_3$, δ 2.81 (2H, t, J = 6.8 Hz), 2.81-3.02 (2H, m), 3.82 (3H, s), 4.25 (2H, t, J = 6.8 Hz), 5.04 (1H, dt, J = 5.4, 7.8 Hz), 6.14 (1H, dt, J = 7.6, 15.6 Hz), 6.48 (1H, d, J = 7.8 Hz), 6.53 (1H, d, J = 15.6 Hz), 6.65 (1H, t, J = 4.9 Hz), 7.22-7.41 (7H, m), 8.34 (2H, d, J = 4.9 Hz). |

TABLE 11

Structure: 2,6-dichlorobenzamide with α-amino acid CO₂M, side chain = CH₂-CH₂-CH=CH-(4-Y-phenyl)

| Ex No. | Y | M | ESI-MS | NMR (H1) chemical shift |
|---|---|---|---|---|
| 31 | N-(2-cyanoethyl)-N-(pyrimidin-2-yl)amino | Na | 508 (M − Na)⁻ | dmso-d$^6$, δ 2.60-2.82 (2H, m), 2.83 (2H, t, J = 6.8 Hz), 4.00-4.06 (1H, m), 4.17 (2H, t, J = 6.8 Hz), 6.25 (1H, dt, J = 7.1, 15.6 Hz), 6.40 (1H, d, J = 15.6 Hz), 6.76 (1H, t, J = 4.9 Hz), 7.21-7.46 (7H, m), 7.66-7.73 (1H, m), 8.37 (2H, d, J = 4.9 Hz) |

TABLE 11-continued

| Ex No. | Y | M | ESI-MS | NMR (H1) chemical shift |
|---|---|---|---|---|
| 32 | N-benzyl-N-(pyrimidin-2-yl)amino | Me | 561 (M + H)+ | |
| 33 | N-benzyl-N-(pyrimidin-2-yl)amino | Na | 545 (M − Na)− | CD$_3$OD, δ 2.73 (1H, m), 2.91 (1H, m), 4.58 (1H, dd, J = 6.6, 4.9 Hz), 5.22 (2H, brs), 6.31 (1H, dt, J = 15.6, 7.1 Hz), 6.49 (1H, d, J = 15.6 Hz), 6.69 (1H, t, J = 4.9 Hz), 7.09 (2H, d, J = 8.5 Hz), 7.19 (6H, m), 7.34 (5H, m), 8.30 (2H, d, J = 4.9 Hz) |
| 34 | N-(4-methoxybenzyl)-N-(pyrimidin-2-yl)amino | Me | 591 (M + H)+ | |
| 35 | N-(4-methoxybenzyl)-N-(pyrimidin-2-yl)amino | Na | 575 (M − Na)− | CD$_3$OD, δ 2.73 (1H, m), 2.90 (1H, m), 3.72 (3H, s), 4.60 (1H, m), 5.14 (2H, brs), 6.32 (1H, dt, J = 15.9, 7.3 Hz), 6.49 (1H, d, J = 15.9 Hz), 6.67 (1H, t, J = 4.9 Hz), 6.77 (2H, d, J = 8.8 Hz), 7.04 (2H, d, J = 8.3 Hz), 7.12 (2H, d, J = 8.8 Hz), 7.35 (5H, m), 8.29 (2H, d, J = 4.9 Hz) |
| 36 | N-butyl-N-(pyrimidin-2-yl)amino | Me | 527 (M + H)+ | |

TABLE 11-continued

[Structure: 2,6-dichlorobenzamide linked via NH to CH(CO₂M)-CH₂-CH=CH-(4-Y-phenyl)]

| Ex No. | Y | M | ESI-MS | NMR (H1) chemical shift |
|---|---|---|---|---|
| 37 | —N(n-butyl)(pyrimidin-2-yl) | Na | 511 (M − Na)⁻ | CD₃OD, δ 0.91 (3H, t, J = 7.3 Hz), 1.31 (2H, m), 1.58 (2H, td, J = 7.3, 4.9 Hz), 2.75 (1H, m), 2.92 (1H, m), 3.94 (2H, t, J = 7.3 Hz), 4.60 (1H, dd, J = 7.6, 4.9 Hz), 6.35 (1H, dt, J = 15.6, 7.3 Hz), 6.54 (1H, d, J = 15.6 Hz), 6.62 (1H, t, J = 4.9 Hz), 7.14 (2H, d, J = 8.6 Hz), 7.37 (5H, m), 8.25 (1H, d, J = 4.9 Hz) |
| 38 | —N(pyridin-3-ylmethyl)(pyrimidin-2-yl) | Me | 562 (M + H)⁺ | |
| 39 | —N(pyridin-3-ylmethyl)(pyrimidin-2-yl) | Na | 546 (M − Na)⁻ | CD₃OD, δ 2.73 (1H, m), 2.91 (1H, m), 4.58 (1H, dd, J = 6.6, 4.9 Hz), 5.27 (2H, s), 6.31 (1H, dt, J = 15.6, 7.3 Hz), 6.50 (1H, d, J = 15.6 Hz), 6.73 (1H, t, J = 4.9 Hz), 7.12 (2H, d, J = 8.3 Hz), 7.35 (6H, m), 7.73 (1H, d, J = 7.8 Hz), 8.31 (2H, d, J = 4.9 Hz), 8.36 (1H, d, J = 4.4 Hz), 8.50 (1H, brs) |
| 40 | —N(thiazol-4-ylmethyl)(pyrimidin-2-yl) | Me | 568 (M + H)⁺ | |

TABLE 12

| Ex No. | Y | M | ESI-MS | NMR (H1) chemical shift |
|---|---|---|---|---|
| 41 | (N-pyrimidin-2-yl, N-(thiazol-4-ylmethyl)amino) | Na | 552 (M − Na)⁻ | CD₃OD, δ 2.64 (1H, m), 2.82 (1H, m), 4.48 (1H, dd, J = 6.6, 4.6 Hz), 5.28 (2H, brs), 6.23 (1H, dt, J = 15.9, 6.9 Hz), 6.40 (1H, d, J = 15.9 Hz), 6.62 (1H, 1, J = 4.9 Hz), 7.10 (2H, d, J = 8.6 Hz), 7.29 (7H, m), 8.21 (2H, d, J = 4.9 Hz), 8.81 (1H, d, J = 2.0 Hz) |
| 42 | (N-methyl-N-(4-methoxypyrimidin-2-yl)amino) | Me | 515 (M + H)⁺ | |
| 43 | (N-methyl-N-(4-methoxypyrimidin-2-yl)amino) | H | 499 (M − H)⁻ | CDCl₃, δ 2.83 (1H, m), 2.97 (1H, m), 3.52 (3H, s), 3.82 (3H, s), 5.04 (1H, m), 6.10 (1H, m), 6.44-6.54 (2H, m), 7.07-7.35 (7H, m), 8.07 (1H, d, J = 5.6 Hz). |
| 44 | (N-methyl-N-(4,6-dimethoxypyrimidin-2-yl)amino) | Me | 545 (M + H)⁺ | |
| 45 | (N-methyl-N-(4,6-dimethoxypyrimidin-2-yl)amino) | H | 529 (M − H)⁻ | CDCl₃, δ 2.82 (1H, m), 2.97 (1H, m), 3.52 (3H, s), 3.79 (6H, s), 5.05 (1H, dd, J = 5.6 and 13.4 Hz), 6.11 (1H, m), 6.49 (2H, m), 7.24-7.34 (7H, m). |
| 46 | (N-phenyl-N-(pyrimidin-2-yl)amino) | Me | 547 (M + H)⁺ | |

TABLE 12-continued

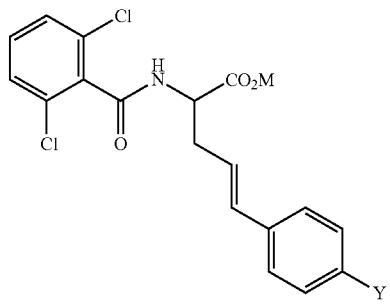

| Ex No. | Y | M | ESI-MS | NMR (H1) chemical shift |
|---|---|---|---|---|
| 47 | *N*-phenyl-*N*-(pyrimidin-2-yl)amino | Na | 531 (M − Na)⁻ | CD₃OD, δ 2.73 (1H, m), 2.92 (1H, m), 4.60 (1H, dd, J = 6.4, 4.6 Hz), 6.32 (1H, dt, J = 15.9, 7.3 Hz), 6.50 (1H, d, J = 15.9 Hz), 6.81 (1H, t, J = 4.9 Hz), 7.12 (2H, d, J = 8.6 Hz), 7.20 (3H, m), 7.36 (8H, m), 8.30 (2H, d, J = 4.9 Hz) |
| 48 | *N*-(tetrahydropyran-4-yl)-*N*-(pyrimidin-2-yl)amino | Me | 555 (M + H)⁺ | |
| 49 | *N*-(tetrahydropyran-4-yl)-*N*-(pyrimidin-2-yl)amino | Na | 539 (M − Na)⁻ | CD₃OD, δ 1.48 (1H, dd, J = 12.5, 4.6 Hz), 1.54 (1H, dd, J = 12.5, 4.6 Hz), 1.83 (2H, m), 2.75 (1H, m), 2.93 (1H, m), 3.52 (2H, m), 4.00 (2H, m), 4.61 (1H, dd, J = 6.6, 4.9 Hz), 4.53-4.97 (1H, m), 6.38 (1H, dt, J = 15.6, 7.1 Hz), 6.57 (1H, d, J = 15.6 Hz), 6.61 (1H, t, J = 4.9 Hz), 7.02 (2H, d, J = 8.3 Hz), 7.38 (3H, m), 7.45 (2H, d, J = 15.6 Hz), 8.23 (2H, d, J = 4.9 Hz) |
| 50 | *N*-(3-methylbut-2-en-1-yl)-*N*-(pyrimidin-2-yl)amino | Me | 539 (M + H)⁺ | |
| 51 | *N*-(3-methylbut-2-en-1-yl)-*N*-(pyrimidin-2-yl)amino | Na | 523 (M − Na)⁻ | dmso-d⁶, δ 1.52 (3H, s), 1.63 (3H, s), 2.60-2.68 (1H, m), 2.76-2.83 (1H, m), 4.04-4.10 (1H, m), 4.51-4.53 (2H, m), 5.26-5.34 (1H, m), 6.20-6.27 (1H, m), 6.39 (1H, d, J = 15.9 Hz), 6.68 (1H, t, J = 4.6 Hz), 7.15-7.75 (7H, m), 8.32-8.45 (3H, m) |

TABLE 13

[Structure: 2,6-dichlorobenzoyl-NH-CH(CO₂M)-CH₂-CH=CH-(4-Y-phenyl)]

| Ex No. | Y | M | ESI-MS | NMR (H1) chemical shift |
|---|---|---|---|---|
| 52 | N-(pyrimidin-2-yl)-N-(cyclopropylmethyl)amino | Me | 525 (M + H)⁺ | |
| 53 | N-(pyrimidin-2-yl)-N-(cyclopropylmethyl)amino | Na | 509 (M − Na)⁻ | dmso-d⁶, δ 0.08-0.16 (2H, m), 0.35-0.41 (2H, m), 1.04-1.12 (1H, m), 2.62-2.68 (1H, m), 2.77-2.84 (1H, m), 3.80 (2H, d, J = 6.8 Hz), 4.11 (1H, dd, J = 11.2, 5.4 Hz), 6.22-6.29 (1H, m), 6.41 (1H, d, J = 15.9 Hz), 6.67 (1H, t, J = 4.6 Hz), 7.18-7.46 (7H, m), 7.78 (1H, d, J = 6.4 Hz), 8.30 (2H, d, J = 4.6 Hz) |
| 54 | N-(pyrimidin-2-yl)-N-(isobutyl)amino | Me | 527 (M + H)⁺ | |
| 55 | N-(pyrimidin-2-yl)-N-(isobutyl)amino | Na | 511 (M − Na)⁻ | dmso-d⁶, δ 0.85 (6H, d, J = 6.8 Hz), 1.83-1.92 (1H, m), 2.60-2.67 (1H, m), 2.76-2.83 (1H, m), 3.83 (2H, d, J = 7.3 Hz), 4.02 (1H, dd, J = 11.2, 5.1 Hz), 6.20-6.27 (1H, m), 6.39 (1H, d, J = 15.6 Hz), 6.66 (1H, t, J = 4.6 Hz), 7.19-7.47 (7H, m), 7.70 (1H, d, J = 6.1 Hz), 8.30 (2H, d, J = 4.6 Hz) |
| 56 | N-(pyrimidin-2-yl)-N-(n-propyl)amino | Me | 525 (M + H)⁺ | CDCl₃, δ 0.91 (3H, t, J = 7.6 Hz), 1.66 (2H, dd, J = 15.4, 7.6 Hz), 2.49-2.87 (1H, m), 2.93-2.98 (1H, m), 3.82 (3H, s), 3.91 (2H, t, J = 7.6 Hz), 5.04 (1H, td, J = 7.8, 5.1 Hz), 6.07-6.14 (1H, m), 6.46 (1H, d, J = 7.6 Hz), 6.52 (1H, t, J = 4.6 Hz), 6.53 (1H, d, J = 15.9 Hz), 7.16-7.37 (7H, m), 8.29 (2H, d, J = 4.6 Hz) |
| 57 | N-(pyrimidin-2-yl)-N-(n-propyl)amino | H | 509 (M − H)⁻ | CDCl₃, δ 0.91 (3H, t, J = 7.3 Hz), 1.66 (2H, s, J = 7.6 Hz), 2.66 (2H, brm), 3.81~3.97 (2H, m), 4.75 (1H, dt, J = 7.3, 5.1 Hz), 5.92 (1H, ddd, J = 15.1, 7.6, 7.6 Hz), 6.21 (1H, d, J = 15.9 Hz), 6.29 (1H, d, J = 7.3 Hz), 6.62 (1H, t, J = 4.9 Hz), 7.20 (2H, d, J = 8.3 Hz), 7.28~7.37 (5H, m), 8.41 (2H, d, J = 4.9 Hz) |

TABLE 13-continued

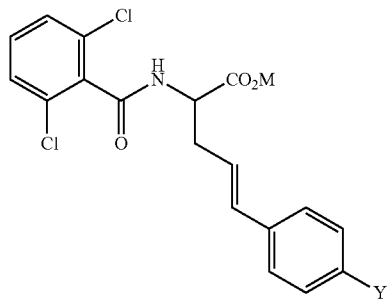

| Ex No. | Y | M | ESI-MS | NMR (H1) chemical shift |
|---|---|---|---|---|
| 58 | N-pyrimidin-2-yl, N-(pyridin-4-ylmethyl)amino | Me | 562 (M + H)+ | CDCl$_3$, δ 2.80-2.98 (2H, m), 3.81 (3H, s), 5.00-5.04 (1H, m), 5.23 (2H, s), 6.08-6.12 (1H, m), 6.45 (1H, d, J = 7.6 Hz), 6.49 (1H, d, J = 15.4 Hz), 6.64 (1H, t, J = 4.6 Hz), 7.20 (2H, d, J = 7.1 Hz), 7.25-7.38 (7H, m), 8.34 (2H, d, J = 4.9 Hz), 8.50 (2H, d, J = 4.6 Hz) |
| 59 | N-pyrimidin-2-yl, N-(pyridin-4-ylmethyl)amino | H | 546 (M − H)− | CDCl$_3$, δ 2.90~3.07 (2H, m), 4.92 (1H, brdd), 5.26 (2H, dd, J = 18.8, 16.8 Hz), 6.12 (1H, ddd, J = 15.3, 7.6, 7.6 Hz), 6.49 (1H, d, J = 15.6 Hz), 6.66~6.70 (2H, m), 7.12 (2H, d, J = 8.3 Hz), 7.22~7.34 (7H, m), 8.35 (2H, d, J = 4.9 Hz), 8.51 (2H, d, J = 5.6 Hz) |
| 60 | N-pyrimidin-2-yl, N-(pyridin-2-ylmethyl)amino | Me | 562 (M + H)+ | CDCl$_3$, δ 2.80-2.96 (2H, m), 3.80 (3H, s), 5.00-5.04 (1H, s), 5.37 (2H, s), 6.03-6.10 (1H, m), 6.44 (1H, d, J = 8.1 Hz), 6.49 (1H, d, J = 5.9 Hz), 6.62 (1H, t, J = 4.6 Hz), 7.13 (1H, dd, J = 6.6, 4.6 Hz), 7.24-7.36 (8H, m), 7.57-7.61 (1H, m), 8.34 (2H, d, J = 4.9 Hz), 8.53 (1H, d, J = 3.9 Hz) |
| 61 | N-pyrimidin-2-yl, N-(pyridin-2-ylmethyl)amino | H | 546 (M − H)− | CDCl$_3$, δ 2.71~2.81 (2H, m), 4.83 (1H, ddd, J = 6.3, 4.8, 4.8 Hz), 5.38 (2H, d, J = 4.3 Hz), 6.02 (1H, ddd, J = 15.3, 7.6, 7.6 Hz), 6.32 (1H, d, J = 15.9 Hz), 6.51 (1H, d, J = 7.3 Hz), 6.65 (1H, dd, J = 4.8, 4.8 Hz), 7.43~7.15 (9H, m), 7.69 (1H, ddd, J = 7.8, 7.8, 1.7 Hz), 8.37 (2H, d, J = 4.9 Hz), 8.56(1H, d, J = 4.2 Hz) |

TABLE 14

| Ex No. | ESI-MS | NMR (H1) chemical shift |
| --- | --- | --- |
| 62 | 453 (M + H)+ | |
| 63 | 437 (M − H)− | dmso-d6, δ 2.56-2.63 (1H, m), 2.68-2.73 (1H, m), 3.43 (3H, s), 4.52-4.57 (1H, m), 6.23 (1H, td, J = 15.6, 7.3 Hz), 6.50 (1H, d, J = 16.1 Hz), 6.72 (1H, t, J = 5.1 Hz), 7.14 (2H, t, J = 8.1 Hz), 7.27 (2H, d, J = 8.1 Hz), 7.35 (2H, d, J = 8.3 Hz), 7.50 (1H, t, J = 7.8 Hz), 8.34 (2H, d, J = 4.9 Hz), 9.12 (1H, d, J = 8.1 Hz), 12.80 (1H, brs) |
| 64 | 469 (M + H)+ | |
| 65 | 453 (M − H)− | dmso-d6, δ 2.60 (1H, m), 2.70 (1H, m), 3.44 (3H, s), 4.57 (1H, m), 6.26 (1H, td, J = 7.1, 15.6 Hz), 6.51 (1H, d, J = 15.6 Hz), 6.74 (1H, t, J = 4.6 Hz), 7.27-7.37 (6H, m), 7.47 (1H, td, J = 8.0, 6.1 Hz), 8.36 (2H, d, J = 4.6 Hz), 9.16 (1H, d, J = 8.0 Hz) |

TABLE 14-continued

| Ex No. | | ESI-MS | NMR (H1) chemical shift |
|---|---|---|---|
| 66 | [structure] | 465 (M + H)+ | |
| 67 | [structure] | 449 (M − H)− | dmso-d6, δ 2.28 (3H, s), 2.61 (1H, m), 2.71 (1H, m), 3.44 (3H, s), 4.55 (1H, m), 6.30 (1H, td, J = 7.5, 15.9 Hz), 6.51 (1H, d, J = 15.9 Hz), 6.74 (1H, t, J = 4.4 Hz), 7.20-7.37 (7H, m), 8.36 (2H, d, J = 4.4 Hz), 8.93 (1H, d, J = 7.5 Hz) |
| 68 | [structure] | 445 (M + H)+ | |

TABLE 15

| Ex No. | | ESI-MS | NMR (H1) chemical shift |
|---|---|---|---|
| 69 | [structure] | 429 (M − H)− | dmso-d6, δ 2.21 (6H, s), 2.59 (1H, m), 2.72 (1H, m), 3.44 (3H, s), 4.55 (1H, m), 6.28 (1H, td, J = 7.1, 15.6 Hz), 6.50 (1H, d, J = 15.6 Hz), 6.74 (1H, t, J = 4.9 Hz), 7.01 (2H, d, J = 7.5 Hz), 7.15 (1H, t, J = 7.5 Hz), 7.28 (2H, d, J = 8.5 Hz), 7.36 (2H, d, J = 8.5 Hz), 8.36 (2H, d, J = 4.9 Hz), 8.70 (1H, d, J = 8.0 Hz), 12.7 (1H, s) |

TABLE 15-continued

| Ex No. | | ESI-MS | NMR (H1) chemical shift |
|---|---|---|---|
| 70 | [structure] | 492 (M + H)+ | |
| 71 | [structure] | 476 (M − H)− | CDCl₃, δ 2.82 (1H, m), 2.22-2.99 (3H, m), 3.64 (2H, t, J = 4.0 Hz), 5.01 (1H, m), 6.10 (1H, m), 6.53 (1H, d, J = 16.0 Hz), 6.63 (1H, d, J = 8.0 Hz), 6.96 (2H, t, J = 8.0 Hz), 7.22-7.41 (5H, m), 8.12 (1H, d, J = 4.0 Hz), 8.61 (1H, d, J = 2.2 Hz). |
| 72 | [structure] | 472 (M + H)+ | CDCl₃, δ 3.10 (1H, dd, J = 4.6, 17.1 Hz), 3.25 (1H, dd, J = 4.6, 17.1 Hz), 3.86 (3H, s), 5.06 (1H, dt, J = 4.6, 7.8 Hz), 6.72-6.74 (1H, m), 7.05 (1H, t, J = 4.6 Hz), 7.10-7.43 (7H, m), 8.56 (2H, d, J = 4.6 Hz). |
| 73 | [structure] | 454 (M − Na)− | dmso-d⁶, δ 2.86 (1H, dd, J = 4.9, 16.6 Hz), 3.10 (1H, dd, J = 4.9, 16.6 Hz), 4.01-4.08 (1H, m), 7.14-7.48 (8H, m), 7.85-7.90 (1H, m), 8.63 (2H, d, J = 4.6 Hz) |

US 9,162,988 B2
115                                                                 116
TABLE 15-continued
| Ex No. | | ESI-MS | NMR (H1) chemical shift |
|---|---|---|---|
| 74 | 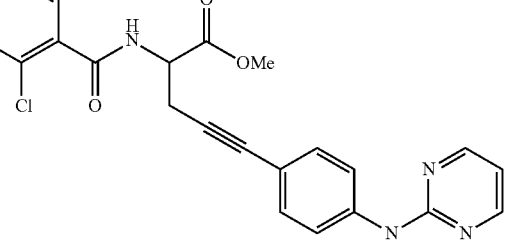 | 467 (M + H)+ | |
| 75 | 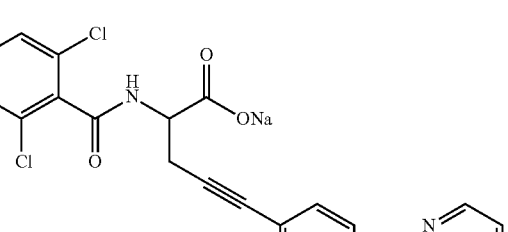 | 453 (M − Na)− | dmso-d6, δ 2.85 (1H, dd, J = 16.9, 4.4 Hz), 3.09 (1H, dd, J = 16.9, 4.8 Hz), 3.98 (1H, m), 6.84 (1H, t, J = 4.6 Hz), 7.21 (2H, d, J = 8.6 Hz), 7.39 (1H, t, J = 6.8 Hz), 7.46 (2H, d, J = 6.8 Hz), 7.71 (2H, d, J = 8.6 Hz), 7.81 (1H, brs), 8.48 (2H, d, J = 4.6 Hz), 9.75 (1H, brs) |
| 76 | 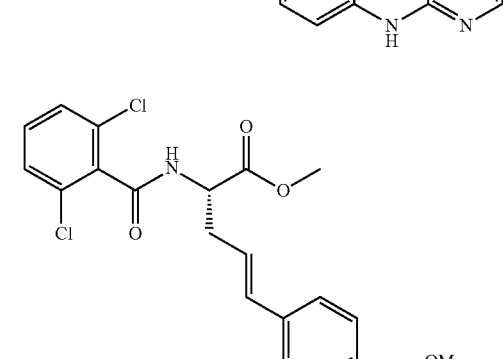 | 492 (M + H)+ | CDCl3, δ 1.92 (4H, br), 2.77-2.84 (1H, m), 2.94-2.96 (4H, brm), 3.73-3.80 (7H, brm), 5.03 (1H, dd, J = 12.9, 5.6 Hz), 6.12-6.20 (1H, m), 6.52 (1H, d, J = 15.6 Hz), 6.73-6.75 (1H, br), 7.22-7.45 (7H, m) |
TABLE 16
| Ex No. | | ESI-MS | NMR (H1) chemical shift |
|---|---|---|---|
| 77 | | 476 (M − H)− | dmso-d6, δ 1.88-1.90 (4H, m), 2.56-2.63 (1H, m), 2.68-2.74 (1H, m), 2.84 (3H, s), 3.66-3.68 (4H, m), 4.55-4.60 (1H, brm), 6.30 (1H, td, J = 15.9, 7.1 Hz), 6.50 (1H, d, J = 15.9 Hz), 7.31-7.48 (7H, m), 9.12 (1H, brs), 12.77 (1H, brs) |

TABLE 16-continued

| Ex No. | | ESI-MS | NMR (H1) chemical shift |
|---|---|---|---|
| 78 | (structure) | 476 (M − Na)⁻ | dmso-d⁶, δ 1.87-1.89 (4H, m), 2.61-2.66 (1H, m), 2.75-2.82 (1H, m), 2.84 (3H, s), 3.65-3.67 (4H, m), 4.07 (1H, dd, J = 11.5, 5.4 Hz), 6.22-6.30 (1H, m), 6.38 (1H, d, J = 15.9 Hz), 7.30 (4H, s), 7.32-7.45 (3H, m), 7.76 (1H, d, J = 6.6 Hz) |
| 79 | (structure) | 485 (M + H)⁺ | CDCl₃, δ 2.80-2.87 (1H, m), 2.93-3.00 (1H, m), 3.51 (3H, s), 3.81 (3H, s), 5.01-5.06 (1H, m), 6.06-6.14 (1H, m), 6.47 (1H, d, J = 7.8 Hz), 6.52 (1H, d, J = 15.6 Hz), 6.58 (1H, t, J = 4.9 Hz), 7.24-7.37 (7H, m), 8.34 (2H, d, J = 4.9 Hz) |
| 80 | (structure) | 469 (M − H)⁻ | CDCl3, δ 2.60-2.64 (1H, m), 2.74-2.81 (1H, m), 3.51 (3H, s), 4.69-4.73 (1H, m), 5.94 (1H, dd, J = 15.6, 6.1 Hz), 6.35 (1H, d, J = 15.6 Hz), 6.45 (1H, d, J = 7.3 Hz), 6.65 (1H, t, J = 4.9 Hz), 7.23-7.27 (3H, m), 7.30 (1H, s), 7.32 (1H, d, J = 2.2 Hz), 7.38 (2H, d, J = 8.3 Hz), 8.42 (2H, d, J = 4.9 Hz) |
| 81 | (structure) | 469 (M − Na)⁻ | dmso-d⁶, δ 2.60-2.66 (1H, m), 2.76-2.82 (1H, m), 3.42 (3H, s), 4.04 (1H, dd, J = 11.0, 5.1 Hz), 6.22 (1H, td, J = 15.9, 7.1 Hz), 6.38 (1H, d, J = 15.9 Hz), 6.71 (1H, t, J = 4.6 Hz), 7.23 (2H, d, J = 8.5 Hz), 7.29 (2H, d, J = 8.5 Hz), 7.37 (1H, dd, J = 9.3, 6.8 Hz), 7.44 (2H, d, J = 7.6 Hz), 7.72 (1H, d, J = 6.1 Hz), 8.34 (2H, d, J = 4.6 Hz) |

TABLE 16-continued

| Ex No. | ESI-MS | NMR (H1) chemical shift |
|---|---|---|
| 82 | 513 (M + H)+ | CDCl3, δ 1.12 (3H, s), 1.14 (3H, s), 2.81-2.88 (1H, m), 2.94-3.01 (1H, m), 3.82 (3H, s), 5.05 (1H, td, J = 7.8, 5.4 Hz), 5.12-5.18 (1H, m), 6.10-6.18 (1H, m), 6.47-6.50 (2H, m), 6.55 (1H, d, J = 15.6 Hz), 7.07 (2H, d, J = 8.3 Hz), 7.25-7.34 (3H, m), 7.39 (2H, d, J = 8.3 Hz), 8.27 (2H, d, J = 4.6 Hz) |
| 83 | 497 (M − H)− | CDCl3, δ 1.13 (3H, s), 1.16 (3H, s), 2.60-2.64 (1H, m), 2.71-2.78 (1H, m), 4.68 (1H, td, J = 7.3, 4.6 Hz), 5.20 (1H, td, J = 13.7, 6.6 Hz), 5.97 (1H, dd, J = 15.9, 6.1 Hz), 6.35 (1H, d, J = 15.9 Hz), 6.45 (1H, d, J = 7.3 Hz), 6.60 (1H, t, J = 4.9 Hz), 7.12 (2H, d, J = 8.5 Hz), 7.24-7.33 (3H, m), 7.41 (2H, d, J = 8.3 Hz), 8.38 (2H, d, J = 4.9 Hz) |
| 84 | 497 (M − Na)− | dmso-d6, δ 1.07 (3H, s), 1.09 (3H, s), 2.63-2.67 (1H, brm), 2.78-2.80 (1H, brm), 4.04 (1H, brm), 5.04-5.08 (1H, m), 6.25-6.29 (1H, m), 6.42 (1H, d, J = 15.9 Hz), 6.61 (1H, t, J = 4.6 Hz), 7.02 (2H, d, J = 8.1 Hz), 7.33 (2H, d, J = 8.1 Hz), 7.37-7.41 (1H, m), 7.46 (2H, d, J = 7.6 Hz), 7.72 (1H, brs), 8.27 (2H, d, J = 4.4 Hz) |

Example 85

Pharmacokinetic Evaluation in Rats

Each compound was dissolved in PBS or PBS containing 10% PEG, thereby preparing 0.5 mg/mL dosing solution. The compound was administered orally or intravenously to male SD rats (7 to 9 weeks old). Blood was collected with time from the tail vein at time points up to 8 hours after the administration, and obtained blood was centrifuged to collect blood plasma. The blood plasma was pretreated by using the solid-phase extraction method, and the concentration of the compound was analyzed with LC/MS/MS (ESI negative mode).

The obtained pharmacokinetic parameters are summarized in Table 17. As the Comparative Compound, 2-[4-((3,5-dichlorobenzensulfonylamino)methyl)benzoylamino]-5-(4-(methyl-pyrimidin-2-ylamino)phenyl)pent-4-enoic acid (XXI) described in WO 99/26923 was used.

TABLE 17

| Example No. | BA(%) | $CL_{tot}$ (ml/hr/kg) |
|---|---|---|
| 4 | 55.0 | 607 |
| 6 | 68.5 | 1185 |
| 22 | 61.7 | 306 |
| 24 | 42.3 | 756 |
| 28 | 80.6 | 895 |
| 70 | 63.4 | 532 |
| 77 | 20.0 | 962 |
| 78 | 26.1 | 996 |
| 80 | 47.6 | 906 |
| 81 | 50.9 | 966 |
| 83 | 40.0 | 1087 |
| 84 | 58.5 | 1178 |
| Comparative Compound | 1.7 | 1284 |

["BA" in Table 17 means bioavailability, and "$CL_{tot}$" means total clearance.]

(XXI)

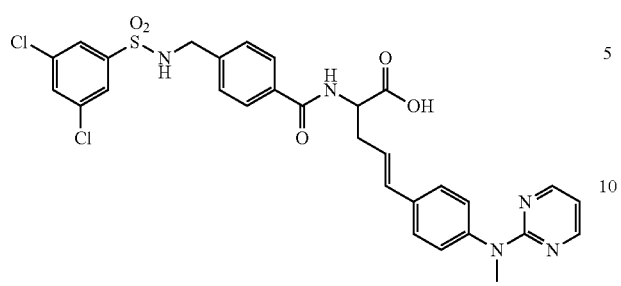

As is apparent from Table 17, the therapeutic or prophylactic agents for allergic dermatitis according to the present invention showed excellent bioavailabilities and low total clearance values compared to the Comparative Compound. Therefore, the agents have the excellent effects when they are administered orally, and the effects are sustained because of their excellent in vivo stability.

Example 86

Measurement of Inhibitory Effect on Leukocyte Functions

Jurkat cells which are a cell line originated from human acute T cell lymphoma were allowed to react with BCECF-AM at 37° C. for 20 minutes to fluorescently label the cells. The fluorescently labelled Jurkat cells were allowed to react with ligand-expressing cells or with a ligand-immobilized plate at 37° C. for 30 minutes. After removing non-adherent cells by washing, 1% NP40 was added to lyse the adherent cells, and fluorescence intensity was measured with Cytofluor 2300 (Millipore). From the obtained fluorescence intensity, the number of adherent cells was calculated. Each test compound was reacted with the Jurkat cells before the beginning of the adhesion reaction. In Table 18, the $IC_{50}$ of each compound (i.e. the concentration at which the number of adherent cells is reduced by 50%) is shown.

TABLE 18

| Example No. | $IC_{50}$ (μM) |
| --- | --- |
| 4 | 0.247 |
| 5 | 0.100 |
| 8 | 0.069 |
| 10 | 0.220 |
| 12 | 0.220 |
| 22 | 0.160 |
| 24 | 0.220 |
| 26 | 0.036 |
| 28 | 0.056 |
| 29 | 0.041 |
| 31 | 0.041 |
| 35 | 0.088 |
| 37 | 0.160 |
| 39 | 0.071 |
| 41 | 0.950 |

TABLE 18-continued

| Example No. | $IC_{50}$ (μM) |
| --- | --- |
| 45 | 0.890 |
| 47 | 0.930 |
| 49 | 0.079 |
| 51 | 0.100 |
| 53 | 0.120 |
| 55 | 0.420 |
| 57 | 0.110 |
| 59 | 0.043 |
| 61 | 0.033 |
| 67 | 0.280 |
| 69 | 0.530 |
| 77 | 0.049 |
| 78 | 0.054 |
| 80 | 0.095 |
| 81 | 0.082 |
| 83 | 0.017 |
| 84 | 0.030 |

As is apparent from Table 18, the therapeutic or prophylactic agents of the present invention clearly inhibit functions of leukocytes involved in the development of allergic dermatitis, so that they exhibit therapeutic and/or prophylactic actions against allergic dermatitis.

Example 87

Measurement of Inhibitory Effect on Inflammatory Mediator Production by Leukocytes A mixture of human peripheral blood and physiological saline containing 3% dextran was left to stand for 30 minutes and then the upper layer was recovered. The upper layer was overlaid on Histopaque 1077 (SIGMA), and the resultant was centrifuged at 1400 rpm for 30 minutes. The supernatant was removed by aspiration and a buffer was added to the precipitate to prepare a neutrophil suspension ($4 \times 10^5$ cells/mL). To the neutrophil suspension, ionomycin was added and the mixture was incubated at 37° C. for 30 minutes, followed by quantification of leukotriene B4 by EIA (Amersham, Biotrak EIA system). Each test compound was added to the neutrophil suspension before adding ionomycin. In Table 19, the $IC_{50}$ of each compound (i.e. the concentration at which the production of Leukotriene B4 is inhibited by 50%) is shown.

TABLE 19

| Example No. | $IC_{50}$ (μM) |
| --- | --- |
| 4 | 52.3 |
| 6 | 5.63 |
| 22 | 176 |
| 28 | 7.40 |
| 33 | 16.3 |
| 67 | 30.0 |

As is apparent from Table 19, the therapeutic or prophylactic agents of the present invention inhibit production of inflammatory mediators by leukocytes involved in the development of allergic dermatitis, so that they exhibit therapeutic and/or prophylactic actions against allergic dermatitis.

Example 88

Inhibitory Effect on Skin Swelling Response in Mouse Allergic Dermatitis Model This method was carried out in accordance with the literature "Inflamm. Res., 47, 506-511 (1998)".
To each BLAB/c mouse (female, 7 weeks old, JAPAN CHARLES RIVER), mouse IgE anti-DNP antibody (2.5 mg/kg, SEIKAGAKU CORPORATION) was intravenously administered to passively sensitize the mouse. Twenty four hours later, 20 μL of 0.38% 2,4-dinitrofluorobenzene (DNFB, SIGMA) dissolved in acetone:olive oil (4:1) was applied to the auricle of the sensitized mouse to induce inflammation. The thickness of the auricle was measured with time till 24 hours after the induction with Digimatic Indicator (Mitutoyo), and the ear swelling ratio was calculated according to the following equation:

Ear Swelling Ratio (%)=$(A-B)/B \times 100$

A: Thickness of the right auricle after the induction
B: Thickness of the right auricle before the induction Each test compound was dissolved in phosphate buffered saline and orally administered at a dose of 50 mg/kg before the induction.

As a result, the compounds described in Example 4, Example 6, Example 22, Example 28, Example 77, Example 78, Example 80, Example 81, Example 83, and Example 84 inhibited the swelling response of the auricle induced by applying the antigen for 24 hours after administration when they were orally administered (Inhibition ratio: 79.8%, 91.2%, 84.7%, 98.5%, 85.8%, 62.5%, 86.3%, 97.9%, 57.4%, 66.9%).

As the Comparative Compound, (E)-2-(4-((3,5-dichlorophenyl sulfonamide)methyl)benzamide)-5-(4-(2-methoxyethoxy)phenyl)pent-4-enoic acid sodium salt (XXII) described in WO 99/26923 was used. In case of the Comparative Compound, the inhibition ratio of the ear swelling measured at 24 hours after oral administration was 2.3%.

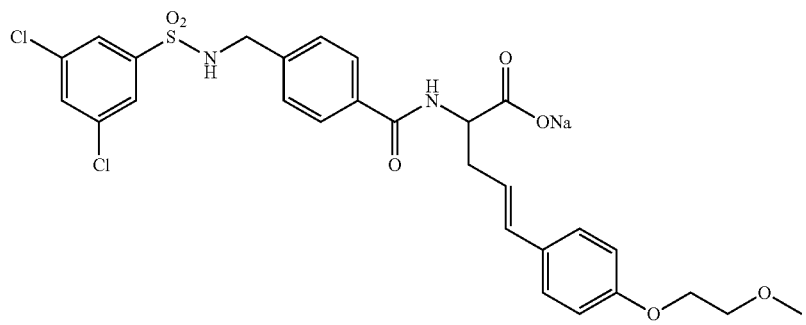

(XXII)

As is apparent from the results, the therapeutic or prophylactic agents of the present invention have an excellent and sustained inhibitory effect on allergic dermatitis when orally administered.

INDUSTRIAL APPLICABILITY

The glycine derivatives or pharmaceutically acceptable salts thereof can be used as therapeutic or prophylactic agents for allergic dermatitis.

What is claimed:

1. A method for treating allergic dermatitis, comprising administering to a patient an effective amount of a therapeutic agent comprising as an effective ingredient (a) compound of Formula (I):

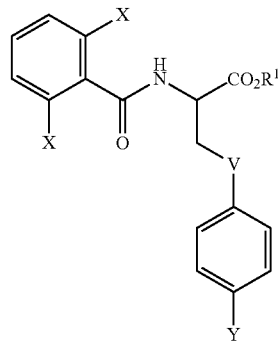

(I)

wherein
$R^1$ represents hydrogen or $C_1$-$C_5$ alkyl;
X independently represents fluoro, chloro, bromo, iodo or $C_1$-$C_3$ alkyl;
V represents —CH=CH— or —C≡C—;
Y represents Formula (II) or Formula (III):

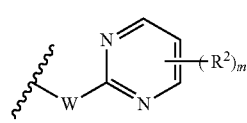

(II)

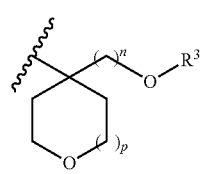

(III)

wherein
$R^2$ represents $C_1$-$C_5$ alkyl or $C_1$-$C_3$ alkoxy;
$R^3$ represents hydrogen or $C_1$-$C_5$ alkyl;
m represents an integer of 0 to 3;
n represents 0 or 1;
p represents an integer of 0 to 2;
W represents —O— or —N($R^4$)—
wherein
$R^4$ represents hydrogen, $C_1$-$C_5$ alkyl, $C_3$-$C_6$ alkenyl, phenyl, benzyl, benzyl substituted with one or two $R^5$s, tetrahydropyranyl, $(CH_2)_q$—O—$CH_3$, pyridylmethyl, —$(CH_2)_q$—CN, $C_4$-$C_7$ cycloalkylmethyl or thiazol-4-ylmethyl;

$R^5$ represents hydroxy or $C_1$-$C_3$ alkoxy; and q represents an integer of 1 to 3;

or (b) a pharmaceutically acceptable salt of the compound of said Formula (I).

2. The therapeutic method for allergic dermatitis of claim 1, wherein, in said Formula (I), V is —CH=CH—, and when Y is represented by the Formula (II), m is 0; or when Y is represented by the Formula (III), p is 1.

3. The therapeutic method for allergic dermatitis of claim 1, wherein in said Formula (I), $R^1$ is hydrogen; and when Y is represented by the Formula (II), W is —N($R^4$)— and $R^4$ is $C_1$-$C_3$ alkyl, cyanoethyl, tetrahydropyranyl or phenyl; or when Y is represented by the Formula (III), n is 0 and $R^3$ is $C_1$-$C_3$ alkyl.

4. The therapeutic method for allergic dermatitis of claim 1, wherein, in said Formula (I), X is independently chloro or methyl;

V is trans —CH=CH—; and when Y is represented by the Formula (II), W is —N($R^4$)— and $R^4$ is methyl or isopropyl; or when Y is represented by the Formula (III), $R^3$ is methyl.

* * * * *

UNITED STATES PATENT AND TRADEMARK OFFICE
CERTIFICATE OF CORRECTION

PATENT NO. : 9,162,988 B2  
APPLICATION NO. : 13/711783  
DATED : October 20, 2015  
INVENTOR(S) : Mie Kaino et al.

Page 1 of 1

It is certified that error appears in the above-identified patent and that said Letters Patent is hereby corrected as shown below:

On Title Page, before Item (51), insert  
--(30) Foreign Application Priority Data June 14, 2006 (JP)................2006-164520--

Signed and Sealed this  
Fifth Day of April, 2016

Michelle K. Lee  
*Director of the United States Patent and Trademark Office*